US006051559A

United States Patent [19]
Tully et al.

[11] Patent Number: 6,051,559
[45] Date of Patent: Apr. 18, 2000

[54] CLONING AND CHARACTERIZING OF GENES ASSOCIATED WITH LONG-TERM MEMORY

[75] Inventors: Timothy P. Tully, Cold Spring Harbor; Jerry Chi-Ping Yin, Huntington, both of N.Y.

[73] Assignee: Cold Spring Harbor Laboratory, Cold Spring Harbor, N.Y.

[21] Appl. No.: 08/361,063

[22] Filed: Dec. 21, 1994

Related U.S. Application Data

[63] Continuation-in-part of application No. 08/319,866, Oct. 7, 1994.
[51] Int. Cl.[7] .................. A61K 39/395; A01N 37/18; A01N 43/04
[52] U.S. Cl. ................. 514/44; 514/2; 424/130.1
[58] Field of Search .............................. 536/23.1; 514/44, 514/2; 424/93.1, 130.1

[56] References Cited

PUBLICATIONS

Drain, Peter et al., "cAMP–Dependent Protein Kinase and the Disruption of Learning in Transgenic Flies," *Neuron*, 6:71–82 (1991).

Skoulakis, Efthimios M.C. et al., "Preferential Expression in Mushroom Bodies of the Catalytic Subunit of Protein Kinase A and Its Role in Learning and Memory," *Neuron*, 11:197–208 (1993).

Davis, Hasker P. and Squire, Larry R., "Protein Synthesis and Memory: A Review," *Psychological Bulletin*, 96(3):518–559 (1984).

Orkin et al. Report and Recomendations . . . Gene Therapy. NIHPress. Dec. 7, 1995. pp. 1–40.

Miller et al. FASEB. vol. 9:190–199, Feb. 1995.

Marshall. Science.269:1050–1055, Aug. 1995.

Culver et al. TIG. 10(5):174–178, May 1994.

Hodgson. Exp Opin Ther. Patents. 5(5):459–468, 1995.

Smolik, S.M., et al., "A Cyclic AMP–Responsive Element–Binding Transcriptional Activator in *Drosophila Melanogaster*, dCREB–A, Is a Member of the Leucine Zipper Family," *Molecular and Cellular Biology*, 12(9):4123–4131 (1992).

Muller, U., "$Ca^{2+}$/Calmodulin–dependent Nitric Oxide Synthase in *Apis mellifera* and *Drosophila melangaster*," *European Journal of Neuroscience*, 6:1362–1370 (1994).

Tully, T., et al., "Independent Memories in Drosophila after Pavlovian Conditioning," Abstract presented at the 23rd Annual Meeting of the Society for Neuroscience in Washington, D.C., USA, Nov. 7–12, 1993. Society for Neuroscience. Abstracts 19 (1–3), Abstract No. 440.8 (1993).

Yin, J.C.P., et al., "Induction of a Dominant Negative CREB Transgene Specifically Blocks Long–Term Memory In Drosophila," *Cell*, 79:49–58 (1994).

Yin, J.C.P., et al., "CREB as a Memory Modulator: Induced Expression of a dCREB2 Activator Isoform Enhances Long-–Term Memory in Drosophila," *Cell*, 81:107–115 (1995).

Yin, J.C.P., et al., "A Drosophila CREB/CREM Homolog Encodes Multiple Isoforms, Including a Cyclic AMP–Dependent Protein Kinase–Responsive Transcriptional Activator and Antagonist," *Molecular and Cellular Biology*, 15(9):5123–5130 (1995).

Regulski, M., and Tully, T., "Molecular and biochemical characterization of dNOS: A Drosophila $Ca^{2+}$/calmodulin–dependent nitric oxide synthase," *Proc. Natl. Acad. Sci. USA*, 92:9072–9076 (1995).

Gerber, Hans–Peter et al., "Transcriptional Activation Modulated by Homopolymeric Glutamine and Proline Stretches," *Science*, 263:808–811 (1994).

Grove, J. Russell et al., "Recombinant Fragment of Protein Kinase Inhibitor Blocks Cyclic AMP–Dependent Gene Transcription," *Science*, 238:530–533 (1987).

Foulkes, Nicholas S. and Sassone–Corsi, Paolo, "More is Better" Activators and Repressors from the Same Gene, *Cell*, 68:411–414 (1992).

Foulkes, Nicholas S. et al., "Developmental switch of CREM function during spermatogenesis: from antagonist to activator," *Nature*, 355:80–84 (1992).

Foulkes, Nicholas S. et al., "CREM Gene: Use of Alternative DNA–Binding Domains Generates Multiple Antagonists of cAMP–Induced Transcription," *Cell*, 64:739–749 (1991).

de Groot, Rolf P. and Sassone–Corsi Paolo, "Hormonal Control of Gene Expression: Multiplicity and Versatility of Cyclic Adenosine 3',5'–Monosphate–Responsive Nuclear Regulators," *Molecular Endocrinology*, 7(2(:145–153 (1993).

Habener, Joel F., "Cyclic AMP Response Element Binding Proteins: A Cornucopia of Transcription Factors," *Molecular Endocrinology*, 4(8):1087–1094 (1990).

Huang, Yan–You and kandel, Eric R., "Recruitment of Long–lasting and Protein Kinase A–dependent Long–term Potentiation in the CA1 Region of Hippocampus Requires Repeated Tetanization," *Learning & Memory*, 1:74–82 (1994).

Frey, U. et al., "Effects of cAMP Simulate a Late Stage of LTP in Hippocampal CA1 Neurons," *Science*, 260:1661–1664 ((1993).

(List continued on next page.)

*Primary Examiner*—Brian R. Stanton
*Assistant Examiner*—Deborah J. R. Clark
*Attorney, Agent, or Firm*—Hamilton, Brook, Smith & Reynolds, P.C.

[57] ABSTRACT

A method of regulating long term memory is disclosed. Also disclosed is isolated DNA encoding a cyclic 3',5'-adenosine monophosphate responsive transcriptional activator, isolated DNA encoding an antagonist of cyclic 3',5'-adenosine monophosphate-inducible transcription, isolated DNA encoding an enhancer-specific activator, and isolated DNA encoding a nitric oxide synthase. A method for assessing the effect of a drug on long term memory formation is also disclosed.

17 Claims, 23 Drawing Sheets

OTHER PUBLICATIONS

Kaang, Bong–Kiun et al., "Activation of cAMP–Responsive Genes by Stimuli That Produce Long–Term Facilitation in Aplysia Sensory Neurons," *Neuron*, 10:427–435 (1993).

Dash, Pramod K. et al., "Injection of thr cAMP–responsive element into the nucleus of Aplysia sensory neurons blocks long–term facilitation," *Nature*, 345:718–721 (1990).

Alberini, Cristina, M. et al., "C/EBP Is an Immediate–Early Gene Required for the Consolidation of Long–Term Facilitation in Aplysia," *Cell*, 76:1099–1114 (1994).

Schacher, S. et al., "cAMP Evokes Long–Term Facilitation in Aplysia Sensory Neurons That Requires New Protein Synthesis," *Science*, 240:1667–1669 (1988).

Montarolo, P.G. et al., "A Critical Period for Macromolecular Synthesis in Long–Term Heterosynaptic Facilitation in Aplysia," *Science*, 234:1249–1254 (1986).

Chrivia, John C. et al., "Phosphorylated CREB binds specifically to the nuclear protein CBP," *Nautre*, 365:855–859 (1993).

Mellon, Pamela L. et al., "Regulation of transcription by cyclic AMP–dependent protein kinase," *Proc. Natl. Acad. Sci. USA*, 86:4887–4891 (1989).

Delmas, Véronique et al., "Alternative usage of initiation condons in mRNA encoding the cAMP–responsive–element modulator generates regulators with opposite functions," *Proc. Natl. Acad. Sci. Usa*, 89:4226–4230 (1992).

Ruppert, Siegfried et al., "Multiple mRNA isoforms of the transcription activator protein CREB: generation by alternative splicing and specific expression in primary spermatocytes," *The EMBO Journal*, 11(4):1503–1512 (1992).

Rehfuss, Robert P. et al., "The cAMP–regulated Enhancer–binding Protein ATF–1 Activates Transcription in Response to cAMP–dependent Protein Kinase A," *J. Biol. Chem.*, 266(28):18431–18434 (1991).

Liu, Fang et al., "Activating Transcription Factor–1 Can Mediate $Ca^{2+}$–and cAMP–inducible Transcriptional Activation," *J. Biol Chem.*, 268(9):6714–6720 (1993).

Deutsch, Paul J. et al., "Structural Determinants for Transcriptional Activation by cAMP–responsive DNA Elements," *J. Biol. Chem.*, 263(34):18466–18472 (1988).

Gonzalez, G.A. et al., "Characterization of Motifs Which Are Critical for Activity of the Cyclic AMP–Responsive Transcription Factor CREB," *Mol. Cell. Biol.*, 11(3):1306–1312 (1991).

Meinkoth, Judy L. et al., "Induction of a Cyclic AMP–Responsive Gene in Living Cells Requires the Nuclear Factor CREB," *Mol. Cell. Biol.*, 11(3):1759–1764 (1991).

Huang, Paul L. et al., "Targeted Disruption of the Neuronal Nitric Oxide Synthase Gene," *Cell*, 75:1273–1286 (1993).

Schuman, Erin M. and Madison, Daniel V., "A Requirement for the Intercellular Messenger Nitric Oxide in Long–Term Potentiation," *Science*, 254:1503–1506 (1991).

Xie, Qiano–wen et al., "Cloning and Characterization of Inducible Nitric Oxide Synthase from Mouse Macrophages," *Science*, 256:225–228 (1992).

Bredt, David S. et al., "Cloned and expressed nitric oxide synthase structurally resembles cytochrome P–450 reductase," *Nature*, 351:714–718 (1991).

O'Dell, Thomas J. et al., "Endothelial NOS and the Blockade of LTP by NOS Inhibitors in Mice Lacking Neuronal NOS," *Science*, 265:542–546 (1994).

Rickard, Nikki S. etg al., "A Nitric Oxide Agonist Stimulates Consolidation of Long–Term Memory in the 1–Day Old Chick," *Behavioral Neuroscience*, 108(3):640–644 (1994).

Hölscher, Christian and Rose, Steven P,R. "An inhibitor of nitric oxide synthesis prevents memory formation in the chick," *Neuroscience Letters*, 145:165–167 (1992).

Böhme, Georg Andrees et al., "Altered synaptic plasticity and memory formation in nitric oxide synthase inhibitor–treated rats," *Proc. Natl. Acad. Sci. USA*, 90:9191–9194 (1993).

Haley, Jane E. et al., "The Role of Nitric Oxide in Hippocampal Long–Term Potentiation," *Neuron*, 8:211–216 (1992).

Chapman, Paul F. et al., "Inhibition of nitric oxide synthesis impairs two different forms of learning," *NeuroReport*, 3(7):567–570 (1992).

Edelman, G.M. and Gally, J.A., "Nitric oxide: Linking space and time in the brain," *Proc. Natl. Acad. Sci. USA*, 89:11651–11652 (1992).

Bredt, David S. and Snyder, Solomon H., "Isolation of nitric oxide synthetase, a calmodulin–requiring enzyme," *Proc. Natl. Acad. Sci. USA*, 87:682–685 (1990).

Rees, D.D. et al., "Characterization of three inhibitors of endothelial nitric oxide synthase in vitro and in vivo," *Br. J. Pharmacol.*, 101:746–752 (1990).

Tully, Tim and Quinn, Williams G., "Classical conditioning and retention in normal and mutant *Drosophila melanogaster*," *J Comp Physiol A* 157:263:277 (1985).

Rosenzweig, Mark R. and Bennett, Edward L. "Basic Processes and Modulatory Influences in the Stages of Memory Formation," *Neurobiology of Learning and Memory*, G. Lynch, J.L. McGaugh, and N. M. Weinberger eds. The Guilford Press, New York pp. 263–288 (1984).

Tully, T. et al., "Genetic Dissection of Memory Formation in *Drosophila melanogaster*," *Cold Spring Harbor Symposia on Quantitative Biology*, vol. LV:203–211, Cold Spring Harbor Laboratory Press (1990).

Yin, J. et al., "Expression of a Dominant Negative Form of CREB Interferes with Long–Term Memory," Abstracts presented at the 1993 meeting on Neurobiology of *Drosophila*, Cold Spring Harbor Laboratory (1993).

Regulski, Michael and Tully, Tim "Cloning of a *Drosophila* Nitric Oxide Synthase," Abstracts presented at the 1993 meeting on Neurobiology of *Drosophila*, Cold Spring Harbor Laboratory (1993).

Regulski, Michael and Tully, Tim "Cloning of a *Drosophila* head–specific nitric oxide synthase," Abstracts presented at the 35th Annual *Drosophila* Research Conference in Chicago, Apr. 20–24, 1994.

Huang, Yan–You et al., "cAMP Contributes to Mossy Fiber LTP by Initiating Both a Covalently Mediated Early Phase and Macromolecular Synthesis–Dependent late Phase," *Cell* 79:69–79 (1994).

Tully, T. et al., "Genetic Dissection of Consolidated memory in Drosophila," *Cell* 79:35–47 (1994).

Yamamoto, K.K. et al., "Phosphorylation–induced binding and transcriptional efficacy of nuclear factor CREB," *Nature* 334:494–498 (1988).

Bacskai, Brian J. et al., "Spatially Resolved Dynamics of cAMP and Protein Kinase A Subunits in Aplysia Sensory Neurons," *Science* 260:222–226 (1993).

Frank, David A. and Greenberg, Michael E., "CREB: A Mediator of Long–Term Memory from Mollusks to Mammals," *Cell* 79:5–8 (1994).

Meyer, Terry E. et al., "The Promoter of the Gene Encoding 3',5'–Cyclic Adenosine Monophosphate (cAMP) Response Element Binding Protein Contains cAMP Response Elements: Evidence for Positive Autoregulation of Gene Transcription," *Endocrinology* 132 (2):770–780 (1993).

Bourtchuladze, Roussoudan et al., "Deficient Long–Term Memory in Mice with a Targeted Mutation of the cAMP––Responsive Element–Binding Protein," *Cell* 79:59–68 (1994).

Dash, P.K. et al., "cAMP response element–binding protein is activated by $Ca^{2+}$/calmodulin–as well as cAMP–dependent protein kinase," *Proc. Natl. Acad. Sci. USA* 88:5061–5065 (1991).

Ginty, David D. et al., "Regulation of CREB Phosphorylation in the Suprachiasmatic Nucleus by Light and a Circadian Clock," *Science* 260:238–241 (1993).

Livingstone, Margaret S. et al., "Loss of Calcium/Calmodulin Responsiveness in Adenylate Cyclase of rutabaga, a Drosophila Learning Mutant," *Cell* 37:205–215 (1984).

Levin, Lonny R. et al., "The Drosophila Learning and Memory Gene rutabaga Encodes a $Ca^{2+}$/Calmodulin–Responsive Adenylyl Cyclase," *Cell* 68:479–489 (1992).

Qui, Yuhong and Davis, Ronald L. "Genetic dissection of the learning/memory gene *dunce of Drosophila melanogaster*," *Genes & Development* 7:1447–1458 (1993).

Usui, Takeshi et al., "Isolation of Drosophila CREB–B: A Novel CRE–Binding Protein," *DNA and Cell Biology* 12(7): 589–595 (1993).

```
  1  ATGGACAACAGCATCGTCGAGGAGAACGGCAACTCGTCGGCGGCATCGGGCTCCAATGAC
  1   M  D  N  S  I  V  E  E  N  G  N  S  S  A  A  S  G  S  N  D

61  GTGGTCGATGTCGTTGCCCAACAGGCGGCGGCAGCGGTGGGCGGCGGCGGTGGAGGAGGA
 21   V  V  D  V  V  A  Q  Q  A  A  A  A  V  G  G  G  G  G  G  G

121  GGAGGCGGCGGCGGTGGTGGTAACCCCCAGCAGCAGCAACAGAACCCACAAAGTACAACG
 41   G  G  G  G  G  G  N  P  Q  Q  Q  Q  Q  N  P  Q  S  T  T

181  GCCGGCGGTCCAACGGGTGCGACGAACAACGCCCAGGGAGGCGGAGTGTCCTCCGTGCTG
 61   A  G  G  P  T  G  A  T  N  N  A  Q  G  G  G  V  S  S  V  L

241  ACCACCACCGCCAACTGCAACATACAATACCCCATCCAGACGCTGGCGCAGCACGGACTG
 81   T  T  T  A  N  C  N  I  Q  Y  P  I  Q  T  L  A  Q  H  G  L

301  CAGGTGAGCATTTGGGGACCGGGTGCTTGGTGTCAACTGTCGAGTGTCAGGTGTTACGGA
101   Q  V  S  I  W  G  P  G  A  W  C  Q  L  S  S  V  R  C  Y  G
                      Exon 2

361  TCCCAGCCAGAAGTGGCTACCAAGGATGTGCAGTCCGTGATACAGGCCAATCCCTCGGGA
121   S  Q  P  E  V  A  T  K  D  V  Q  S  V  I  Q  A  N  P  S  G

421  GTCATACAGACAGCAGCTGGAACCCAGCAGCAGCAACAGGCGCTGGCCGCCGCCACAGCG
141   V  I  Q  T  A  A  G  T  Q  Q  Q  Q  Q  A  L  A  A  A  T  A

481  ATGCAGAAGGTGGTCTACGTGGCCAAGCCGCCGAACTCGACGGTCATCCACACGACGCCT
161   M  Q  K  V  V  Y  V  A  K  P  P  N  S  T  V  I  H  T  T  P

541  GGCAATGCAGTGCAAGTGCGTAACAAAATCCCTCCAACCTTTCCATGTAAGATCAAGCCC
181   G  N  A  V  Q  V  R  N  K  I  P  P  T  F  P  C  K  I  K  P
                      Exon 4

601  GAACCGAACACGCAGCACCCGGAGGACAGCGACGAGAGTCTGTCGGACGACGATTCCCAG
201   E  P  N  T  Q  H  P  E  D  S  D  E  S  L  S  D  D  D  S  Q

661  CACCACGCAGCGAGCTGACGCGACGGCCGTCGTACAATAAGATCTTCACCGAGATCAGC
221   H  H  A  S  E  L  T  R  R  P  S  Y  N  K  I  F  T  E  I  S
                       P-box 721  GGTCCGGACATGAGCGGCGCATCGCTTCCCATGTCCGACGGCGTGCTCAATTCCCAGCTG
241   G  P  D  M  S  G  A  S  L  P  M  S  D  G  V  L  N  S  Q  L
                            Exon 6

781  GTGGGGACCGGAGCGGGGGGCAATGCGGCGAACAGCTCCCTGATGCAATTGGATCCCACG
261   V  G  T  G  A  G  G  N  A  A  N  S  S  L  M  Q  L  D  P  T

841  TACTACCTGTCCAATCGGATGTCCTACAACACCAACAACAGCGGGATAGCGGAGGATCAG
281   Y  Y  L  S  N  R  M  S  Y  N  T  N  N  S  G  I  A  E  D  Q

901  ACCCGTAAGCGCGAGATCCGGCTGCAGAAGAACAGGGAGGCGGCGCGTGAGTGCCGGCGC
301   T  R  K  R  E  I  R  L  Q  K  N  R  E  A  A  R  E  C  R  R
         Basic region 961  AAGAAGAAGGAGTACATCAAGTGCCTGGAGAATCGAGTGGCGGTGCTAGAGAACCAAAAC
321   K  K  K  E  Y  I  K  C  L  E  N  R  V  A  V  L  E  N  Q  N
                                Leucine zipper 1021 AAAGCGCTCATCGAGGAGCTGAAGTCGCTCAAGGAGCTCTATTGTCAGACCAAGAACGAT
341   K  A  L  I  E  E  L  K  S  L  K  E  L  Y  C  Q  T  K  N  D

1081 TGA
361  END
```

FIG. 1A dCREB2  RKRE[I]RL[Q]KNREAAARECRRKKKEY[I]KCLENRVAVLENQNK[A]LIEELKS[L]KE[L]YC
CREB    RKREVRLMKNREAAARECRRKKKEYVKCLENRVAVLENQNKTLIEELKALKDLYC
CREM 1  RKRELRLMKNREAAARECRRKKKEYVKCLENRVAVLENQNKTLIEELKALKDLYC
ATF-1   LKREIRLMKNREAAARECRRKKKEYVKCLENRVAVLENQNKTLIEELKTLKDLYS

FIG. 1B

```
  1  ATGTTACTCGGAGAAAATATGTTTTCTACTTTCACATCGTTAGATGCTGCTACCGCTACA
  1  M  L  L  G  E  N  M  F  S  T  F  T  S  L  D  A  A  T  A  T

61  ACCAACACCGGTGAATTCTTAATGAATGAATCTCCAAGGCAAGAAGCCGGTGACTTAATG
 21  T  N  T  G  E  F  L  M  N  E  S ⟨P⟩ R  Q  E  A  G  D  L  M

121  TTGGATAGTCTGGATTTCAACATTATGGGCGAAAACCTGGCAGATGATTTCCAGACCTCG
 41  L  D  S  L  D  F  N  I  M  G  E  N  L  A  D  D  F  Q  T  S

181  GCTTCACCAGCTTCGGAGGACAAGATGACTCCTTTCGTTGTTGATACCAATGTTTTTGAA
 61  A  S  P  A  S  E  D  K  M  T ⟨P⟩ F  V  V  D  T  N  V  F  E

241  TCCGTCTTCAAGAACACCGAAGATACCCTTCTAGGAGATATCGACAATGTTGGTATTGTT
 81  S  V  F  K  N  T  E  D  T  L  L  G  D  I  D  N  V  G  I  V

301  GACACGGAGTTGAAGGAGATGTTCGATTTGGTTGACTCGGAAATCAATAACGGCACTCCT
101  D  T  E  L  K  E  M  F  D  L  V  D  S  E  I  N  N  G  T ⟨P⟩

361  ATCAAGCAGGAAGAAAAGGATGATTTGGAATTTACTTCAAGATCCCAGTCCACCTCAGCT
121  I  K  Q  E  E  K  D  D  L  E  F  T  S  R  S  Q  S  T  S  A

421  CTCTTGTCGTCGAAATCGACTTCTGCTTCTCCAGCTGATGCTGCCGCTGCATGTGCAAGT
141  L  L  S  S  K  S  T  S  A  S ⟨P⟩ A  D  A  A  A  A  C  A  S

481  CCTTCGTCATCGTCTTGTAAAAGATCCTATTCTTCTGCTCAGCTAGAAACTACGGGTTCG
161  P  S  S  S  S  C  K  R  S  Y  S  S  A  Q  L  E  T  T  G  S

541  GATGCTCCAAAGAAAGATAAGCTGGGCTGCACCCCTTACACTAGAAAACAGAGAAACAAT
181  D  A  P  K  K  D  K  L  G  C  T  P  Y  T  R  K  Q  R  N  N

601  CCATTACCTCCGGTCATTCCAAAGGGTCAGGATGTTGCTTCTATGAAAAGGGCAAGAAAC
201  P  L  P  P  V  I  P  K  G  Q  D  V  A  S  M (K)(R) A (R) N
                                                  ━━━━━━━━━━━━━━━
                                                  Basic region →

661  ACTGAGGCCGCAAGAAGATCAAGAGCCAGAAAAATGGAAAGAATGTCCCAACTTGAAGAA
221  T  E  A  A (R)(R) S (R) A (R)(K) M  E (R) M  S  Q [L] E  E
     ━━━━━━━━━━━━━━━━━━━━━━━━━━━━━━━━━━━━━━━━━━━━━━━━━━━
                                                      Leucine 721  AAGTGTCAAAGCTTGTTGAAGGAAAACGACGACTTGAAAGCTCAAGTTCAAGCTTTGAAG
241  K  C  Q  S [L] L  K  E  N  D  D [L] K  A  Q  V  Q  A [L] K
                                                      zipper →

781  AAATTACTTGGACAACAA
261  K  L  L  G  Q  Q
```

FIG. 5

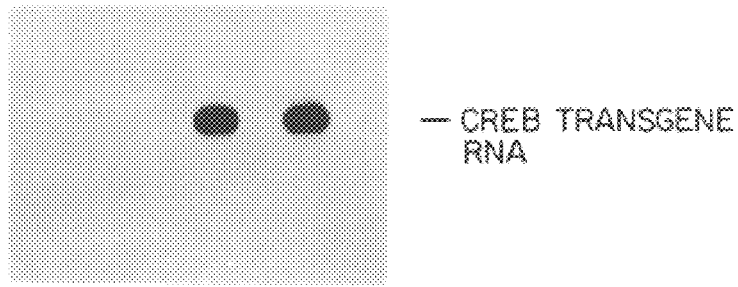
FIG. 7A — CREB TRANSGENE RNA
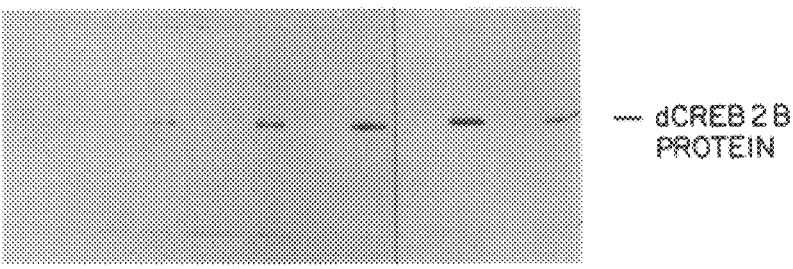
FIG. 7B — dCREB2B PROTEIN
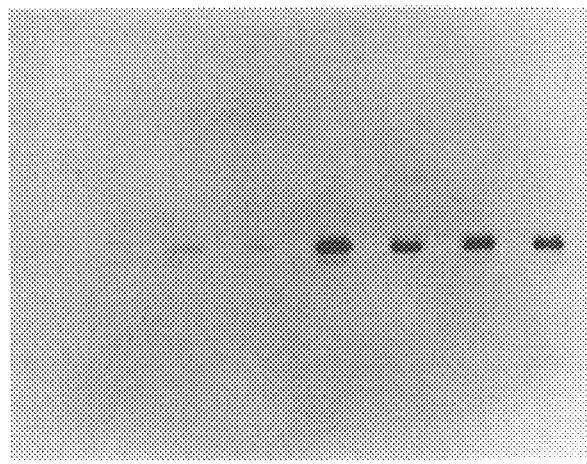
FIG. 7C

```
DNOS    MSQ------H FTSIFENLRF VTIKRATNAQ QQQQQQQQQQ L---------    35
BENOS   MGN------- ---------L --KSVG---- --QE--PGPP ----------    14
RNNOS   MEENTFGVQQ IQPNVISVRL FKRKVGGLGF LVKERVSKPP VIISDLIRGG    50
MMNOS   MAC------- -----PWKFL FKVKSY---- --QSDLKEEK ----------    22

DNOS    QQQQQQLQQQ ---------- -----KAQTQ QQNSRKIKTQ ATPTLNGNGL    70
BENOS   ----CGL--- ---------- ---------G L----GLG-- ----LGLCGK    28
RNNOS   AAEQSGLIQA GDIILAVNDR PLVDLSYDSA LEVLRGIASE THVVLILRGP   100
MMNOS   -----DI--- ---------- ---------N N----NVK-- ----KTPCAV    35

DNOS    LS-GNPNGGG GDSSPSHEVD HPGGAQGAQ- ---------- -------AAG   101
BENOS   QG-------- -PASPAPEPS RAPAPATP-- ---------- ----------    47
RNNOS   EGFTTHLETT FTGDGTPKTI RVTQPLGPPT KAVDLSHQPS ASKDQSLAVD   150
MMNOS   LS-------- PTIQDDPKSH QNGSPQLL-- ---------- ----------    55

DNOS    GLPSLSGTPL RHH------- ---KRASIST ASPPIRERRG ----------   131
BENOS   ------HAPD HS-------- ---------- -PAPNS---- ----------    58
RNNOS   RVTGLGNGPQ HAQGHGQGAG SVSQANGVAI DPTMKSTKAN LQDIGEHDEL   200
MMNOS   ------TGTA QN-------- ---------- --VPESL--- ----------    66

DNOS    --TNTSIVVE LDGSGSGSGS GG-------- ---------- GGVGVGQGAG CPPSGSCTAS   171
BENOS   -----PTLT- ---------- ---------- -----R---- ------PPEG    67
RNNOS   LKEIEPVLSI LNSGSKATNR GGPAKAEMKD TGIQVDRDLD GKSHKAPPLG   250
MMNOS   -----DKLHV ---------- ---------- ---------- ------TSTR    75

DNOS    GKSSRELSPS PKNQQQPRKM SQDYRSR--- -AGSFMHLDD EGRSLLMRKP   217
BENOS   ---------- ---------- ---------- ---------- -------PKF    70
RNNOS   GDNDRVFNDL WGKDNVPVIL NNPYSEKEQS PTSGKQSPTK NGSPSRCPRF   300
MMNOS   ---------- ---------- ---------- ---------- -------PQY    78

DNOS    MRLKNIEGRP EVYDTLHCKG REILSCSKAT CTSSIMN--- -IGNAAVEAR   263
BENOS   PRVKNWELGS ITYDTLCAQS QQDGPCTPRR CLGSLVLPRK LQTRPSPGPP   120
RNNOS   LKVKNWETDV VLTDTLHLKS TLETGCTEHI CMGSIMLPSQ -HTRKPEDVR   349
MMNOS   VRIKNWGSGE ILHDTLHHKA TSDFTCKSKS CLGSIMNPKS LTRGPRDKPT   128

DNOS    KSDLILEHAK DFLEQYFTSI KRTSCTAHET RWKQVRQSIE TTGHYQLTET   313
BENOS   PAEQLLSQAR DFINQYYSSI KRSGSQAHEE RLQEVEAEVA STGTIHLRES   170
RNNOS   TKDQLFPLAK EFLDQYYSSI KRFGSKAHMD RLEEVNKEIE STSTYQLKDT   399
MMNOS   PLEELLPHAI EFINQYYGSF KEAKIEEHLA RLEAVTKEIE TTGTYQLTLD   178

------Heme------
DNOS    ELIYGAKLAW RNSSRCIGRI QWSKLQVFDC RYVTTTSGMF EAICNHIKYA   363
BENOS   ELVFGAKQAW RNAPRCVGRI QWGKLQVFDA RDCSSAQEMF TYICNHIKYA   220
RNNOS   ELIYGAKHAW RNASRCVGRI QWSKLQVFDA RDCTTAHGMF NYICNHVKYA   449
MMNOS   ELIFATKMAW RNAPRCIGRI QWSNLQVFDA RNCSTAQEMF QHICRHILYA   228

DNOS    TNKGNLRSAI TIFPQRTDAK HDYRIWNNQL ISYAGYKQAD GKIIGDPMNV   413
BENOS   TNRGNLRSAI TVFPQRAPGR GDFRIWNSQL VRYAGYRQQD GSVRGDPANV   270
RNNOS   TNKGNLRSAI TIFPQRTDGK HDFRVWNSQL IRYAGYKQPD GSTLGDPANV   499
MMNOS   TNNGNIRSAI TVFPQRSDGK HDFRLWNSQL IRYAGYQMPD GTIRGDAATL   278

DNOS    EFTEVCTKLG WKSKGSEWDI LPLVVSANGH DPDYFDYPPE LILEVPLTHP   463
BENOS   EITELCIQHG WTPGNGRFDV LPLLLQAPDE APELFVLPPE LVLEVPLGAP   320
RNNOS   QFTEICIQQG WKAPRGRFDV LPLLLQANGN DPELFQIPPE LVLEVPIRHP   549
MMNOS   EFTQLCIDLG WKPRYGRFDV LPLVLQADGQ DPEVFEIPPD LVLEVTMEHP   328

DNOS    KFEWFSDLGL RWYALPAVSS MLFDVGGIQF TATTFSGWYM STEIGSRNLC   513
BENOS   HTGVVRGPGL RWYALPAVSN MLLEIGGLEF SAAPFSGWYM STEIGTRNLC   370
RNNOS   KFDWFKDLGL KWYGLPAVSN MLLEIGGLEF SACPFSGWYM GTEIGVRDYC   599
MMNOS   KYEWFQELGL KWYALPAVAN MLLEVGGLEF PACPFNGWYM GTEIGVRDFC   378
```

FIG. 16A

| | | | | |
|---|---|---|---|---|
| DNOS | DTNRRNMLET VALKMQLDTR TPTSLWKDKA VVEMNIAVLH SYQSRNVTIV | 563 |
| BENOS | DPHRYNILED VAVCMDLDTR TTSSLWKDKA AVEINLAVLH SFQLAKVTIV | 420 |
| RNNOS | DNSRYNILEE VAKKMDLDMR KTSSLWKDQA LVEINIAVLY SFQSDKVTIV | 649 |
| MMNOS | DTQRYNILEE VGRRMGLETH TLASLWKDRA VTEINVAVLH SFQKQNVTIM | 428 |

| | | |
|---|---|---|
| DNOS | DHHTASESFM KHFENESKLR NGCPADWIWI VPPLSGSITP VFHQEMALYY | 613 |
| BENOS | DHHAATVSFM KHLDNEQKAR GGCPADWAWI VPPIYGSLPP VFHQEMVNYI | 470 |
| RNNOS | DHHSATESFI KHMENEYRCR GGCPADWVWI VPPMSGSITP VFHQEMLNYR | 699 |
| MMNOS | DHHTASESFM KHMQNEYRAR GGCPADWIWL VPPVSGSITP VFHQEMLNYV | 478 |

————CaM————

| | | |
|---|---|---|
| DNOS | LKPSFEYQDP AWRTHVWKKG RGESKGKKPR RKFNFKQIAR AVKFTSKLFG | 663 |
| BENOS | LSPAFRYQPD PWKG---SAT KGAG---ITR KK-TFKEVAN AVKISASLMG | 513 |
| RNNOS | LTPSFEYQPD PWNTHVWKGT NGTP---TKR RAIGFKKLAE AVKFSAKLMG | 746 |
| MMNOS | LSPFYYYQIE PWKTHIWQNE KLRP----RR REIRFRVLVK VVFFASMLMR | 524 |

| | | |
|---|---|---|
| DNOS | RALSKRIKAT VLYATETGKS EQYAKQLCEL LGHAFNAQIY CMSDYDISSI | 713 |
| BENOS | TLMAKRVKAT ILYASETGRA QSYAQQLGRL FRKAFDPRVL CMDEYDVVSL | 563 |
| RNNOS | QAMAKRVKAT ILYATETGKS QAYAKTLCEI FKHAFDAKAM SMEEYDIVHL | 796 |
| MMNOS | KVMASRVRAT VLFATETGKS EALARDLATL FSYAFNTKVV CMDQYKASTL | 574 |

| | | |
|---|---|---|
| DNOS | EHEALLIVVA STFGNGDPPE NGELFSQELY AMRVQESSEH GLQDSSIGSS | 763 |
| BENOS | EHEALVLVVT STFGNGDPPE NGESFAAALM EMSGPYNS-- ---SPRPEQH | 608 |
| RNNOS | EHEALVLVVT STFGNGDPPE NGEKFGCALM EMRHP----- ---NSVQEER | 838 |
| MMNOS | EEEQLLLVVT STFGNGDCPS NGQTLKKSL- ---------- ---------- | 603 |

| | | |
|---|---|---|
| DNOS | KSFMKASSRQ EFMKLPLQQV KRIDRWDSLR GSTSDTFTEE TFGPLSNVRF | 813 |
| BENOS | KSYK---IR- -FNSVS-CSD PLVSSWRRKR KESSNT---D SAGALGTLRF | 649 |
| RNNOS | KSYK---VR- -FNSVS-SYS DSRKSSGDGP DLRDNF---E STGPLANVRF | 879 |
| MMNOS | --FM---LR- ---------- ---------- ELNH------ ------TFRY | 615 |

————FMN————

| | | |
|---|---|---|
| DNOS | AVFALGSSAY PNFCAFGQYV DNILGELGGE RLLRVAYGDE MCGQEQSFRK | 863 |
| BENOS | CVFGLGSRAY PHFCAFARAV DTRLEELGGE RLLQLGQGDE LCGQEEAFRG | 699 |
| RNNOS | SVFGLGSRAY PHFCAFGHAV DTLLEELGGE RILKMREGDE LCGQEEAFRT | 929 |
| MMNOS | AVFGLGSSMY PQFCAFAHDI DQKLSHLGAS QLAPTGEGDE LSGQEDAFRS | 665 |

| | | |
|---|---|---|
| DNOS | WAPEVFKLAC ETFCLDPEES --LSDASLAL QNDSLTVNTV RLVPSANKGS | 911 |
| BENOS | WAKAAFQASC ETFCVGEEAK --AAAQDIFS PKRSWKRQRY RLSAQAEGLQ | 747 |
| RNNOS | WAKKVFKAAC DVFCVGDDVN IEKPNNSLIS NDRSWKRNKF RLTYVAEAPD | 979 |
| MMNOS | WAVQTFRAAC ETFDVRSKHH --IQIPKRFT SNATWEPQQY RLIQSPEPLD | 713 |

| | | |
|---|---|---|
| DNOS | LDSSLSKYHN KKVHCCKAKA KPH-NLTRLS EGAKTTMLLE ICAPGLEYEP | 960 |
| BENOS | LLPGLIHVHR RKMFQATVLS VENLQSSKST RATILVRLDT AGQEGLQYQP | 797 |
| RNNOS | LTQGLSNVHK KRVSAARLLS RQNLQSPKFS RSTIFVRLHT NGNQELQYQP | 1029 |
| MMNOS | LNRALSSIHA KNVFTMRLKS QQNLQSEKSS RTTLLVQLTF EGSRGPSYLP | 763 |

—FAD·PPi——

| | | |
|---|---|---|
| DNOS | GDHVGIFPAN RTELVDGLLN RLVGVDNPDE VLQLQLLKEK QTSNGIFKCW | 1010 |
| BENOS | GDHIGISAPN RPGLVEALLS RVEDPPPPTE SVAVEQL-EK GSPGGPPPSW | 846 |
| RNNOS | GDHLGVFPGN HEDLVNALIE RLEDAPPANH VVKVEMLEER NTALGVISNW | 1079 |
| MMNOS | GEHLGIFPGN QTALVQGILE RVVDCPTPHQ TVCLEVLDES G------SYW | 807 |

| | | |
|---|---|---|
| DNOS | EPHDKIPPDT LRNLLARFFD LTTPPSRQLL TLLAGFCEDT ADKERLELLV | 1060 |
| BENOS | VRDPRLPPCT VRQALTFFLD ITSPPSPRLL RLLSTLAEEP SEQQELETLS | 896 |
| RNNOS | KDESRLPPCT IFQAFKYYLD ITTPPTPLQL QQFASLATNE KEKQRLLVLS | 1129 |
| MMNOS | VKDKRLPPCS LSQALTYFLD ITTPPTQLQL HKLARFATDE TDRQRLEALQ | 857 |

—FAD-ISO—

| | | |
|---|---|---|
| DNOS | NDSSAYEDWR HWRLPHLLDV LEEFPSCRPP APLLLAQLTP LQPRFYSISS | 1110 |
| BENOS | QDPRRYEEWK LVRCPTLLEV LEQFPSVALP APLLLTQLPL LQPRYYSVSS | 946 |
| RNNOS | KGLQEYEEWK WGKNPTMVEV LEEFPSIQMP ATLLLTQLSL LQPRYYSISS | 1179 |
| MMNOS | Q-PSEYNDWK FSNNPTFLEV LEEFPSLHVP AAFLLSQLPI LKPRYYSISS | 906 |

FIG. 16B

| | | | | | | |
|---|---|---|---|---|---|---|
| DNOS | SPRRVSDEIH | LTVAIVKYRC | EDGQGDERYG | VCSNYLSGLR | ADDELFMFVR | 1160 |
| BENOS | APNAHPGEVH | LTVAVLAYRT | QDGLGPLHYG | VCSTWLSQLK | TGDPVPCFIR | 996 |
| RNNOS | SPDMYPDEVH | LTVAIVSYHT | RDGEGPVHHG | VCSSWLNRIQ | ADDVVPCFVR | 1229 |
| MMNOS | SQDHTPSEVH | LTVAVVTYRT | RDGQGPLHHG | VCSTWIRNLK | PQDPVPCFVR | 956 |

————NADPH·Ribose————

| | | | | | | |
|---|---|---|---|---|---|---|
| DNOS | SALGFHLPSD | RSRPIILIGP | GTGIAPFRSF | WQEFQVLRDL | DPTAKLPKMW | 1210 |
| BENOS | GAPSFRLPPD | PYVPCILVGP | GTGIAPFRGF | WQE-RLHDIE | SKGLQPHPMT | 1045 |
| RNNOS | GAPSFHLPRN | PQVPCILVGP | GTGIAPFRSF | WQQ-RQFDIQ | HKGMNPCPMV | 1278 |
| MMNOS | SVSGFQLPED | PSQPCILIGP | GTGIAPFRSF | WQQ-RLHDSQ | HKGLKGGRMS | 1005 |

| | | | | | | |
|---|---|---|---|---|---|---|
| DNOS | LFFGCRNRDV | D-LYAEEKAE | LQKDQILDRV | FLALSREQAI | PKTYVQDLIE | 1259 |
| BENOS | LVFGCRCSQL | DHLYRDEVQD | AQERGVFGRV | LTAFSREPDS | PKTYVQDILR | 1095 |
| RNNOS | LVFGCRQSKI | DHIYREETLQ | AKNKGVFREL | YTAYSREPDR | PKKYVQDVLQ | 1328 |
| MMNOS | LVFGCRHPEE | DHLYQEEMQE | MVRKRVLFQV | HTGYSRLPGK | PKVYVQDILQ | 1055 |

————NADPH·Ade————

| | | | | | | |
|---|---|---|---|---|---|---|
| DNOS | QEF-DSLYQL | IVQERGHIYV | CGDVTMAEHV | YQTIRKCIAG | KEQKSEAEVE | 1308 |
| BENOS | TELAAEVHRV | LCLERGHMFV | CGDVTMATSV | LQTVQRILAT | EGDMELDEAG | 1145 |
| RNNOS | EQLAESVYRA | LKEQGGHIYV | CGDVTMAADV | LKAIQRIMTQ | QGKLSEEDAG | 1378 |
| MMNOS | KQLANEVLSV | LHGEQGHLYI | CGDVRMARDV | ATTLKKLVAT | KLNLSEEQVE | 1105 |

| | | | | | | |
|---|---|---|---|---|---|---|
| DNOS | TFLLTLRDES | RYHEDIFGIT | LRTAEI---- | --HTKSRATA | RIRMAS---- | 1348 |
| BENOS | DVIGVLRDQQ | RYHEDIFGLT | LRTQEVTSRI | RTQSFSLQER | HLRGAVPWAF | 1195 |
| RNNOS | VFISRLRDDN | RYHEDIFGVT | LRTYEVTNRL | RSESIAFIEE | SKKDADE-VF | 1427 |
| MMNOS | DYFFQLKSQK | RYHEDIFGAV | F-SYGA---- | -KKGSALEEP | --KAT----- | 1142 |

| | | |
|---|---|---|
| DNOS | --------QP | 1350 |
| BENOS | DPPGPDTPGP | 1205 |
| RNNOS | --------SS | 1429 |
| MMNOS | --------RL | 1144 |

FIG. 16C

CLONING AND CHARACTERIZING OF GENES ASSOCIATED WITH LONG-TERM MEMORY

RELATED APPLICATIONS

This application is a continuation-in-part of U.S. Ser. No. 08/319,866, filed Oct. 7, 1994, which is incorporated herein by reference.

GOVERNMENT SUPPORT

This invention was made with government support under Grant No. 1RO1 HD32245-01 awarded by the National Institutes of Health. The United States government has certain rights in this invention.

BACKGROUND OF THE INVENTION

Activation of the cyclic 3',5'-adenosine monophosphate (cAMP) signal transduction pathway can have long-lasting global consequences through its influence on the expression of specific genes. This is true for simple organisms as well as mammals, where many of the known cAMP-responsive genes can have important neural and endocrine roles. Additional information regarding activation of this pathway would be useful, particularly as this activation pertains to the ability of animals to remember activities or events.

SUMMARY OF THE INVENTION

The present invention is based on Applicants' discovery of the dCREB1 and dCREB2 genes. The present invention is further based on Applicants' discovery that the Drosophila CREB2 gene codes for proteins of opposite functions. One isoform (e.g., dCREB2-a) encodes a cyclic 3',5'-adenosine monophosphate (cAMP)-responsive transcriptional activator. Another isoform (e.g., dCREB2-b) codes for an antagonist which blocks the activity of the activator.

When the blocking form is placed under the control of the heat-shock promoter, and transgenic flies are made, a brief shift in temperature induces the synthesis of the blocker in the transgenic fly. This induction of the blocker (also referred to herein as the repressor) specifically disrupts long-term, protein synthesis dependent memory of an odor-avoidance behavioral paradigm.

As a result of Applicants' discovery, a method is herein provided to regulate long term memory in an animal. The method of regulating long term memory described herein comprises inducing expression of a dCREB2 gene or a fragment thereof in the animal.

The dCREB2 gene encodes several isoforms. Examples of an isoform encoded by the dCREB2 gene are dCREB2-a, dCREB2-b, dCREB2-c, dCREB2-d, dCREB2-q, dCREB2-r and dCREB2-s.

The isoforms encoded by the dCREB2 gene include cAMP-responsive activator isoforms and antagonistic blocker (or repressor) isoforms of the activator isoforms. Cyclic AMP responsive activator isoforms can function as a cAMP-responsive activator of transcription. Antagonistic repressors can act as a blocker of activators. An example of a cAMP-responsive activator isoform is dCREB2-a. An example of an antagonistic repressor (or blocker) isoform is dCREB2-b. The terms blocker and repressor are used interchangeably herein.

In one embodiment of the invention, the dCREB-2 gene encodes a cAMP-responsive activator isoform and inducing said gene results in the potentiation of long term memory.

Alternatively, inducing the dCREB2 gene encoding a cAMP-responsive activator isoform activates the production of a protein which is necessary for the formation of long term memory.

In another embodiment of the invention, the dCREB2 gene encodes a repressor isoform and inducing said gene results in the blocking of long term memory.

A further embodiment of the invention relates to a method of regulating long term memory in an animal comprising inducing repressor and activator isoforms of dCREB2 wherein long term memory is potentiated in the animal when the net amount of functional activator ($\Delta C$) is greater than zero.

The invention also relates to a method of identifying a substance capable of affecting long term memory in an animal comprising the determination that said substance alters the induction or activity of repressor and activator isoforms of dCREB2 from normal in the animal.

As referred to herein, an activator isoform includes dCREB2-a and functional fragments thereof and a repressor isoform includes dCREB2-b and functional fragments thereof.

Other embodiments of the invention relate to a method of enhancing long term memory formation in an animal comprising increasing the level of activator homodimer from normal, decreasing the level of activator-repressor heterodimer from normal, or decreasing the level of repressor homodimer from normal in the animal.

Still another embodiment of the invention relates to a method of identifying a substance capable of affecting long term memory in an animal comprising the determination that said substance alters activator homodimer, activator-repressor heterodimer and/or repressor homodimer formation from normal in the animal.

As referred to herein, an activator homodimer includes the dCREB2a homodimer, an activator-repressor heterodimer includes the dCREB2a-dCREB2b heterodimer, and a repressor homodimer includes the dCREB2b homodimer.

A further embodiment of the invention relates to isolated DNA encoding a cAMP responsive transcriptional activator. Such a cAMP responsive transcriptional activator can be encoded by a Drosophila dCREB2 gene or by homologues or functional fragments thereof. For example, a cAMP responsive transcriptional activator can be encoded by the dCREB2 gene which codes for dCREB2-a or by a gene encoded by the sequences presented herein.

Still another embodiment of the invention relates to isolated DNA encoding an antagonist of cAMP-inducible transcription. Such an antagonist of cAMP-inducible transcription can be encoded by a Drosophila dCREB2 gene or by homologues or functional fragments thereof. For example, an antagonist of cAMP-inducible transcription can be encoded by the dCREB2 gene which codes for dCREB2-b.

Another embodiment of the invention relates to isolated DNA which encodes a Drosophila dCREB2 gene or functional fragments thereof.

A further embodiment of the invention relates to isolated DNA encoding an enhancer-specific activator. Such an enhancer-specific activator can be encoded by a Drosophila dCREB1 gene or by homologues or functional fragments thereof.

Another embodiment of the invention relates to isolated DNA encoding a nitric oxide synthase of Drosophila (DNOS). Such DNA can encode a DNOS of neuronal locus.

The DNOS encoded can contain, for example, putative heme, calmodulin, flavin mononucleotide (FMN), flavin adenine dinucleotide (FAD) and nicotinamide adenine dinucleotide phosphate, in its reduced form, (NADPH) binding site domains.

A further embodiment of the invention relates to a method for assessing the effect of a drug on long term memory formation comprising administering the drug to Drosophila, subjecting the Drosophila to classical conditioning to at least one odorant and electrical shock, and assessing the performance index of the classical conditioning, wherein the effect of the drug occurs when it alters the performance index from normal. The drug can affect long term memory formation by, for example, altering the induction or activity of repressor and activator isoforms of dCREB2.

BRIEF DESCRIPTION OF THE DRAWINGS

FIG. 1A depicts the DNA sequence (SEQ ID NO.: 1) and predicted amino acid sequence (SEQ ID NO.: 2) of the dCREB2-a coding region. The basic region and leucine zipper domains are indicated by solid and broken bold underlining, respectively; positively-charged residues in the basic region are circled; periodic leucines in the zipper motif are boxed; glutamines in the activation domain are underlined; the short amino acid motif with target sites for kinases, starting at residue 227, is indicated by a bold outline; and sequences specified by alternatively-spliced exons 2, 4 and 6 are shaded.

FIG. 1B depicts the amino acid sequences of the bZIP domains of dCREB2 (SEQ ID NO.: 3), mammalian CREB (SEQ ID NO.: 4), CREM (SEQ ID NO.: 5) and ATF-1 (SEQ ID NO.: 6). Differences between dCREB2 and CREB are boxed.

FIG. 5 depicts the DNA sequence (SEQ ID NO.: 7) and predicted amino acid sequence (SEQ ID NO.: 8) of the dCREB1 coding region. The basic region and leucine zipper domains are indicated by solid and broken bold underlining, respectively; positively-charged residues in the basic region are circled; periodic leucines of the zipper motif are boxed; and in the acid-rich region of the activation domain, negatively-charged amino acids are underlined and proline residues are indicated by diamonds.

FIG. 7A is a photomicrograph of a Northern blot depicting the effect of heat shock induction on dCREB2-b expression: wt=wildtype flies; CREB=17-2 transgenic flies; lanes 1–2: no heat shock; lanes 2–3: immediately after heat shock; lanes 5–6: three hours after heat shock.

FIG. 7B is a photograph of a Western blot depicting the effect of heat shock induction on dCREB2-b protein production: wt=wildtype flies; CREB=17-2 transgenic flies; lanes 1–2: no heat shock; lanes 2–3: immediately after heat shock; lanes 5–6: one hour after heat shock; lanes 7–8: three hours after heat shock; lanes 9–10: 9 hours after heat shock; lanes 11–12: 24 hours after heat shock.

FIG. 7C is a photograph of a Western blot depicting the effect of heat shock induction on dCREB2 and dCREB2-mLZ (a mutated dCREB2-b) protein production: wt=17-2 transgenic flies (expressing wildtype blocker, dCREB2-b); m=A2-2 transgenic flies (expressing mutant blocker, dCREB2-mLZ); lanes 1–2: no heat shock; lanes 3–4: immediately after heat shock; lanes 5–6: three hours after heat shock; lanes 7–8: six hours after heat shock.

FIGS. 16A–16C depict the deduced amino acid sequences of DNOS and mammalian NOSs with amino acid numbering starting at the first methionine in each open reading frame (ORF), putative binding domains for cofactors (overlined) demarcated as in previously published reports on mammalian NOSs, and amino acids which have been proposed as contacts with FAD and NADPH based on crystal structure of the ferrodoxin NADP+reductase (40) conserved at equivalent positions (bullet points): DNOS, Drosophila NOS (SEQ ID NO.: 9); RNNOS, rat neuronal NOS (SEQ ID NO.: 10); BENOS, bovine endothelial NOS (SEQ ID NO.: 11); MMNOS, mouse macrophage NOS (SEQ ID NO.: 12). Sequence alignment and secondary structure predictions were performed by Geneworks 2.3 (IntelliGenetics).

DETAILED DESCRIPTION OF THE INVENTION

Figure 2:
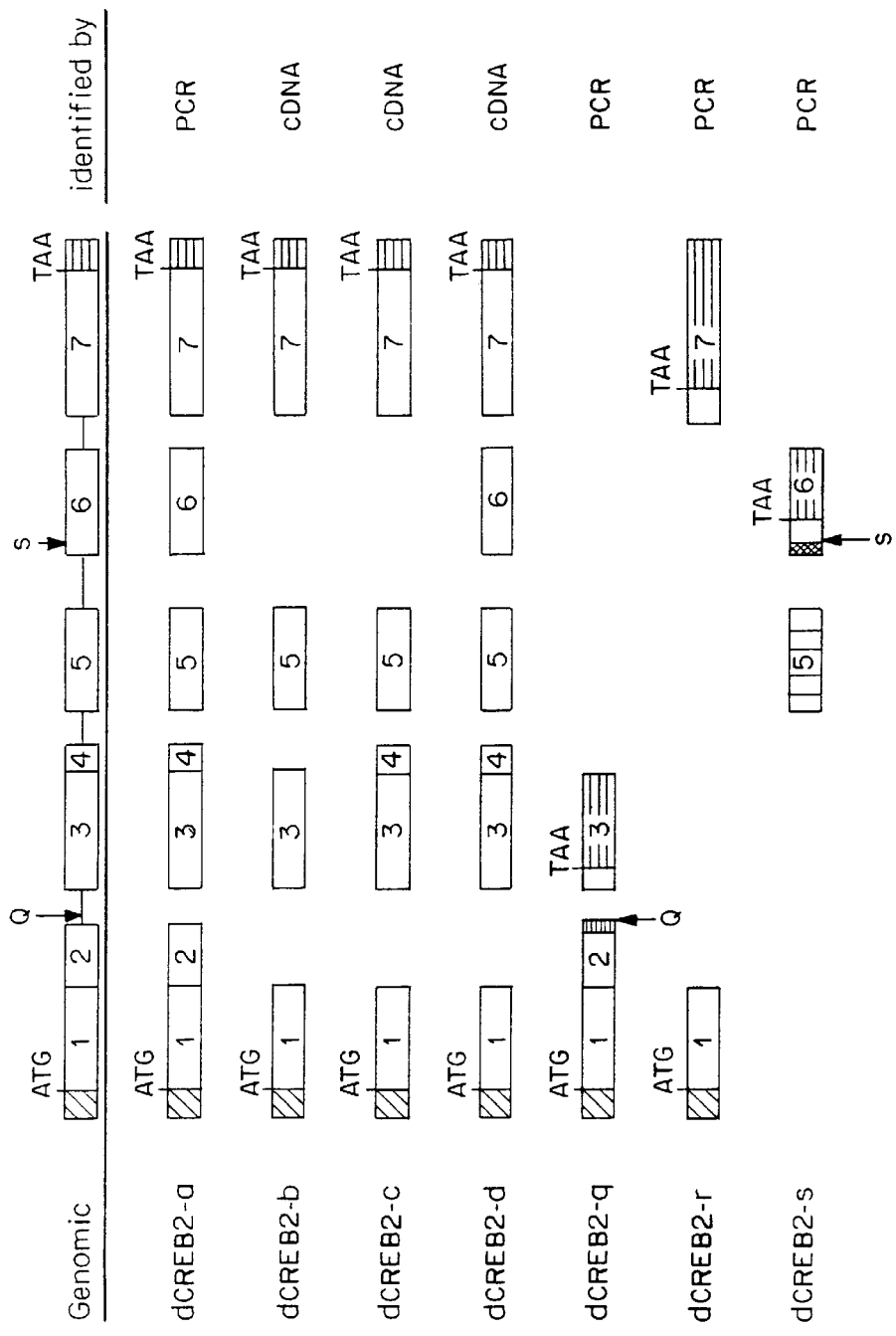
FIG. 2 is a schematic diagram of dCREB2 isoforms with the exon boundaries defined with respect to dCREB2-a. Diagram is not drawn to scale.

Applicants have cloned and characterized two genes, designated dCREB2 and dCREB1, isolated through a DNA-binding expression screen of a Drosophila head cDNA library in which a probe containing three cAMP-responsive element (CRE) sites was used.

The dCREB2 gene codes for the first known cAMP-dependent protein kinase (PKA) responsive CREB/ATF transcriptional activator in Drosophila. A protein data base search showed mammalian CREB, CREM and ATF-1 gene products as homologous to dCREB2. For these reasons, dCREB2 is considered to be a member, not only of the CREB/ATF family, but of the specific cAMP-responsive CREB/CREM/ATF-1 subfamily. It is reasonable to expect that dCREB2 is involved in Drosophila processes which are analogous to those which are thought to depend on cAMP-responsive transcriptional activation in other animal systems.

Applicants have shown that the dCREB2 transcript undergoes alternative splicing. Splice products of dCREB2 were found to fall into two broad categories: one class of transcripts (dCREB2-a, -b, -c, -d) which employs alternative splicing of exons 2, 4 and 6 to produce isoforms whose protein products all have the bZIP domains attached to different versions of the activation domain and a second class of transcripts (dCREB2-q, -r, -s) which have splice sites which result in in-frame stop codons at various positions upstream of the bZIP domain. These all predict truncated activation domains without dimerization or DNA binary activity.

dCREB2-a,-b,-c and -d are splice forms that predict variants of the activation domain attached to a common basic region-leucine zipper. These alternative splice forms result in seemingly minor changes in the size and spacing of parts of the activation domain. Nevertheless, alternative splicing of the activation domain has profound effects on the functional properties of dCREB2 products. Isoform dCREB2-a produces a PKA-responsive transcriptional activator in cell culture, whereas dCREB2-b, lacking exons 2 and 6, produces a specific antagonist. This dCREB2 splicing pattern (and its functional consequences) is virtually identical to that seen in the CREM gene. Similarly located, alternatively-spliced exons in the CREM gene determine whether a particular isoform is an activator or an antagonist (14, 26).

The ability of the phosphorylation domain (KID domain) to activate in trans other constitutive transcription factors which are bound nearby could potentially transform a CREM antagonist (which contains the KID domain but is lacking an exon needed for activation) into a cAMP-responsive activator. Since the modular organization of these molecules has been conserved, dCREB2-d could have this property.

In contrast to the dCREB2 splicing variants that encode isoforms with a basic region-leucine zipper domain, the dCREB2-q, -r and -s splice forms incorporate in-frame stop codons whose predicted protein products are truncated before the bZIP region. Isoforms of this type have been identified among the products of the CREB gene (14, 64), but not the CREM gene. The function of these truncated CREB molecules is not known, but at least one such CREB mRNA is cyclically regulated in rat spermatogenesis (73).

So far, dCREB2 is the only cAMP-responsive CREB transcription factor isolated from Drosophila. Other Drosophila CREB molecules, BBF-2/dCREB-A (1,67) and dCREB1, have less homology to mammalian CREB and CREM. It may be that dCREB2 subsumes functions of both the CREB and CREM genes in Drosophila. The mammalian CREB and CREM genes are remarkably similar to one another in several respects. It has been suggested that CREB and CREM are the product of a gene duplication event (46, 62). dCREB2 has a striking degree of amino acid sequence similarity to the CREB and CREM genes in the bZIP domain. Moreover, comparison of alternative splicing patterns among CREB, CREM and dCREB2 indicates that dCREB2 generates mRNA splicing isoforms similar to exclusive products of both CREB and CREM. Taken together, the sequence information and the splicing organization suggest that dCREB2 is an ancestor of both the mammalian CREB and CREM genes.

As discussed further herein, one phenomenon in which dCREB2 might act with enduring consequences is in long-term memory. This possibility is a particularly tempting one because recent work in Aplysia indicates that a CREB factor is likely to function in long-term facilitation by inducing an "immediate early" gene (2, 13). Recent experiments with a conditionally-expressed dCREB2-b transgene indicate that it has specific effects on long-term memory in Drosophila.

The product of the second gene described herein, dCREB1, also appears to be a member of the CREB/ATF family. Gel-retardation assays indicate that it binds specifically to CREs. It has a basic region and an adjacent leucine zipper at its carboxyl end, but this domain shows limited amino acid sequence similarity to other CREB/ATF genes. The presumed transcriptional activation domain of dCREB1 is of the acid-rich variety. Furthermore, it has no consensus phosphorylation site for PKA. dCREB1 can mediate transcriptional activation from CRE-containing reporters in the Drosophila L2 cell line, but this activation is not dependent or PKA.

A recurrent finding from work on the biology of learning and memory is the central involvement of the cAMP signal transduction pathway. In Aplysia, the cAMP second-messenger system is critically involved in neural events underlying both associative and non-associative modulation of a behavioral reflex (Kandel and Schwartz, 1982; Kandel et al., 1987; Byrne et al., 1993). In Drosophila, two mutants, dunce and rutabaga, were isolated in a behavioral screen for defects in associative learning and are lesioned in genes directly involved in cAMP metabolism (Quinn, et al., 1974; Dudai et al., 1976; Byers et al., 1981; Livingstone et al., 1984; Chen et al., 1986; Levin et al., 1992). These latter observations were extended with a reverse-genetic approach using inducible transgenes expressing peptide inhibitors of cAMP-dependent protein kinase (PKA) and with analyses of mutants in the PKA catalytic subunit (Drain et al., Skoulakis et al., 1993). Recent work on mammalian long-term potentiation (LTP) also has indicated a role for cAMP in synaptic plasticity (Frey et al., 1993; Huang and Kandel, 1994; Bourtchuladze et al., 1994).

The formation of long-lasting memory in animals and of long-term facilitation in Aplysia can be disrupted by drugs that interfere with transcription or translation (Agranoff et al., 1966; Barondes and Cohen, 1968; Davis and Squire, 1984; Rosenzweig and Bennett, 1984; Montarolo et al., 1986). This suggests that memory consolidation requires de novo gene expression. Considered along with the involvement of the cAMP second-messenger pathway, this requirement for newly synthesized gene products suggests a role for cAMP-dependent gene expression in long-term memory (LTM) formation.

In mammals, a subset of genes from the CREB/ATF family are known to mediate cAMP-responsive transcription (Habener, 1990; deGroot and Sassone-Corsi, 1993). CREBs are members of the basic region-leucine zipper transcription factor superfamily (Landschulz et al., 1988). The leucine zipper domain mediates selective homo- and hetero-dimer formation among family members (Hai et al., 1989; Hai and Curran, 1991). CREB dimers bind to a conserved enhancer element (CRE) found in the upstream control region of many cAMP-responsive mammalian genes (Yamamoto et al., 1988). Some CREBs become transcriptional activators when specifically phosphorylated by PKA (Gonzalez and Montminy, 1989, Foulkes et al., 1992), while others, isoforms from the CREM gene, are functional antagonists of these PKA-responsive activators (Foulkes et al., 1991; Foulkes and Sassone-Corsi, 1992).

Work in Aplysia has shown that cAMP-responsive transcription is involved in long-term synaptic plasticity (Schacher et al., 1988; Dash et al, 1990). A primary neuronal co-culture system has been used to study facilitation of synaptic transmission between sensory and motor neurons comprising the monosynaptic component of the Aplysia gill-withdrawal reflex. Injection of oligonucleotides containing CRE sites into the nucleus of the sensory neuron specifically blocked long-term facilitation (Dash et al., 1990). This result suggests that titration of CREB activity might disrupt long-term synaptic plasticity.

Described herein is the cloning and characterization of a Drosophila CREB gene, dCREB2. This gene produces several isoforms that share overall structural homology and nearly complete amino acid identity in the basic region-leucine zipper with mammalian CREBs. The dCREB2-a isoform is a PKA-responsive transcriptional activator whereas the dCREB2-b product blocks PKA-responsive transcription by dCREB2-a in cell culture. These molecules with opposing activities are similar in function to isoforms of the mammalian CREM gene (Foulkes et al., 1991; Foulkes and Sassone-Corsi, 1992; Foulkes et al., 1992). The numerous similarities in sequence and function between dCREB2 and mammalian CREBs suggest that cAMP-responsive transcription is evolutionarily conserved.

Genetic studies of memory formation in Drosophila have revealed that the formation of a protein synthesis-dependent long-term memory (LTM) requires multiple training sessions with a rest interval between them (Tully et al. 1994). As discussed further herein, this LTM is blocked specifically by induced expression of a repressor isoform of the cAMP-responsive transcription factor CREB. Also as discussed further herein, LTM information is enhanced after induced expression of an activator form of CREB. Maximum LTM is achieved after just one training session.

To investigate the role of CREBs in long-term memory (LTM) formation in Drosophila, dominant-negative transgenic lines which express dCREB2-b under the control of a heat-shock promoter (hs-dCREB2-b) were generated. Groups of flies, which had been heat-shock induced or left uninduced, were tested for memory retention after Pavlovian olfactory learning. This acute induction regimen minimized potential complications from inappropriate expression of dCREB2-b during development and allowed a clear assessment of the effect of hs-dCREB2-b induction on memory formation.

In Drosophila, consolidated memory after olfactory learning is composed of two genetically distinct components: anesthesia-resistant memory (ARM) and long-term memory (LTM) (Tully et al., 1994). ARM decays to zero within four days after training, and formation of ARM is insensitive to the protein synthesis inhibitor cycloheximide (CXM) but is disrupted by the radish mutation (Folkers et al., 1993). In contrast, LTM shows essentially no decay over at least seven days, its formation is cycloheximide-sensitive and it is not disrupted by radish. Tully et al. (1994) employed two different training protocols involving massed and spaced sessions (Ebbinghaus, 1885; Baddeley, 1976) to dissect memory formation. The massed training procedure consists of ten consecutive training cycles with no rest interval between them, while the spaced training protocol consists of the same number of sessions but with a 15-minute rest between each. Their genetic dissection revealed that the massed protocol produced only ARM, while the spaced protocol produced memory retention composed of both ARM and LTM.

The behavioral results show that formation of LTM is completely blocked by induced expression of hs-dCREB2-b. This effect is remarkable in its behavioral specificity. ARM, a form of consolidated memory genetically distinguishable from LTM, but co-existing with it one-day after spaced training, was not affected. Learning and peripheral behaviors likewise were normal. Thus, the effect of the induced hs-dCREB2-b transgene is specific to LTM.

Induction of the mutant blocker did not affect LTM. This result, together with the molecular data which showed that induction of the wild-type blocker did not have widespread effects on transcription, suggests that the blocker is reasonably specific at the molecular level when it specifically blocks LTM. The wild-type blocker may disrupt cAMP-dependent transcription in vivo, since it can block cAMP-responsive transcription in cell culture. It is reasonable to infer that dimerization is necessary for blocker function and that the wild-type blocker could interfere with cAMP-responsive transcription either by forming heterodimers with dCREB2-a, the activator, or by forming homodimers and competing for DNA binding with homodimers of dCREB2-a. Thus, activators and repressors may form homodimers or heterodimers. It is reasonable to infer that long term memory is enhanced when the level of activator homodimer is increased from normal and/or when the level of activator-repressor heterodimer is decreased from normal and/or when the level of repressor homodimer is decreased from normal. In any case, the molecular target(s) of dCREB2-b are likely to be interesting because of the behavioral specificity of the block of LTM.

In Drosophila, consolidation of memory into long-lasting forms is subject to disruption by various agents. Tully et al. (1994) used a single-gene mutation radish and the pharmacological agent CXM to show that long-lasting memory in flies is dissectable into two components, a CXM-insensitive ARM, which is disrupted by radish, and a CXM-sensitive LTM, which is normal in radish mutants. As described herein, CREB-family members are likely to be involved in the CXM-sensitve, LTM branch of memory consolidation. The results described herein, taken together with the showing that long-term memory is dissectable into a CXM-insentive ARM and a CXM-sensitive LTM (Tully et al., 1994), show that only one functional component of consolidated memory after olfactory learning lasts longer than four days, requires de novo protein synthesis and involves CREB-family members.

Based on work in Aplysia, a model has been proposed to describe the molecular mechanism(s) underlying the transition from short-term, protein synthesis-independent to long-term, protein synthesis-dependent synaptic plasticity (Alberini et al., 1994). The present work in Drosophila on long-term memory extends this model to the whole organism. Important molecular aspects of this transition seem to involve migration of the catalytic subunit of PKA into the nucleus (Backsai et al., 1993) and subsequent phosphorylation and activation of CREB-family members (Dash et al., 1990; Kaang et al., 1992). In flies, it is likely that the endogenous dCREB2-a isoform is one of these nuclear targets. Activated dCREB2-a molecules then might transcribe other target genes, including the immediate early genes—as is apparently the case in Aplysia. (Alberini et al., 1994).

It is remarkable that the cAMP signal transduction pathway, including its nuclear components, seem to be required for memory-related functions in each of these species and behavioral tasks. Taken together with cellular analyses of a long-lasting form of LTP in hippocampal slices (Frey et al., 1993; Huang and Kandel, 1994), the emerging picture is that cAMP-responsive transcription is a conserved molecular switch involved in the consolidation of short-term memory to long-term memory. Thus, it is reasonable to infer that differential regulation of CREB isoforms serves as a molecular switch for the formation of long term memory.

A universal property of memory formation is that spaced training (repeated training sessions with a rest interval between them) produces stronger, longer-lasting memory than massed training (the same number of training sessions with no rest interval) (Ebbinghaus 1885; Hintzman 1974; Carew et al. 1972; Frost et al. 1985). This phenomenon also exists in fruit flies for a conditioned odor avoidance response (Tully et al. 1994, Tully & Quinn 1985). Genetic dissection of this long-lasting memory has revealed, however, an important difference between massed and spaced training (Tully et al. 1994). Spaced training produces two functionally independent forms of consolidated memory, ARM and LTM, while massed training produces only ARM.

As described herein, ARM and LTM differ primarily in their requirement for protein synthesis during induction (see also Tully et al. 1994). ARM is not affected when flies are fed the protein synthesis inhibitor cycloheximide (CXM) immediately before or after training, while LTM is completely blocked under the same feeding conditions. ARM in normal flies also decays away within four days after training, while LTM shows no decay for at least seven days. Thus, protein synthesis is required to induce LTM, but LTM is maintained indefinitely once formed. These latter properties of LTM have been observed throughout the animal kingdom (Davis and Squire 1984; Castellucci et al. 1989; Erber 1976; Jaffe 1980). The emerging neurobiological interpretation is that formation of LTM involves protein synthesis-dependent structural changes at relevant synapses (Greenough 1984; Buonomano and Byrne 1990; Nazif et al. 1991; Stewart 1991; Bailey and Kandel 1994). The modern molecular view is that regulation of gene expression underlies this protein synthesis-dependent effect (Goelet et al. 1986; Gall and Lauterborn 1991; Armstrong and Montminy 1993).

Why is spaced training required to induce LTM? The massed and spaced procedures both entail ten training sessions; consequently, flies receive equivalent exposure to the relevant stimuli (one odor temporally paired with electric shock and a second odor presented without shock). The only procedural difference between massed and spaced training is the rest interval between each training session. The absence of a rest interval between sessions during massed training does not appear to disrupt the memory formation process (Tully et al. 1994). The level of initial learning assayed immediately after massed training is similar to that after spaced training. In addition, ARM levels are similar after both training procedures. Thus, the presence of a rest interval during spaced training seems crucial to the induction of LTM.

To investigate the temporal kinetics of this rest interval in relation to the formation of LTM (FIGS. 13A and 13B), it was first established that the usual ten sessions of spaced training produced maximal 7-day memory retention (7-day retention is composed solely of LTM, since ARM decays to zero within four days; Tully et al. 1994).

Figure 13A:
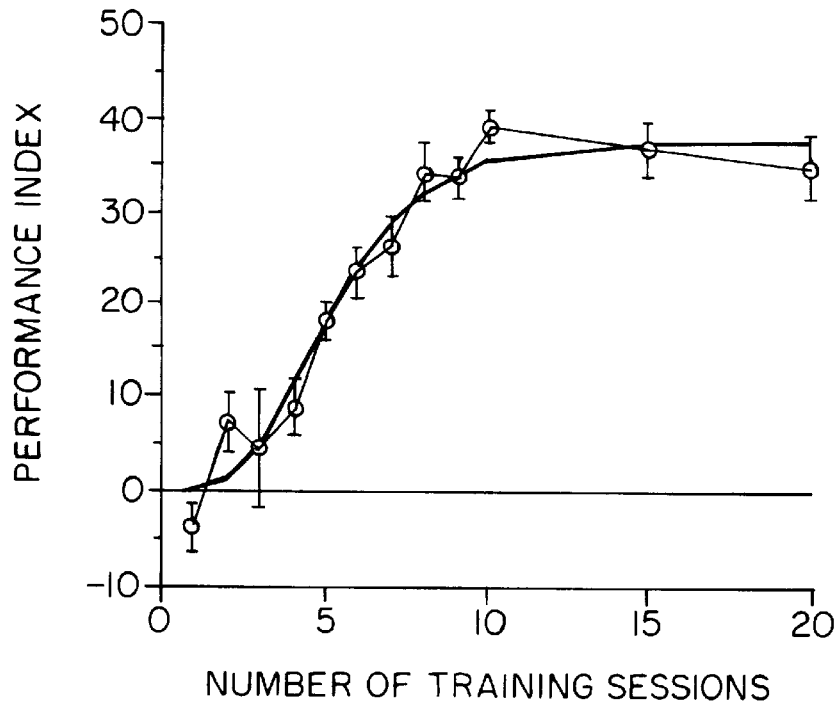
FIG. 13A is a graphic representation of results showing the effect of repeated training sessions on seven-day memory retention (long term memory) in wildtype (Can-S) flies with long term memory as a function of the number of training sessions indicated by open circles and a negative accelerating exponential Gompertz (growth) function fit to the individual performance indexes (PIs) using a nonlinear iterative Least squares method indicated by the solid line.

FIG. 13A shows that 15 or 20 training sessions did not improve memory retention. Thus, ten spaced training sessions produces maximal, asymptotic levels of LTM.

Figure 13B:
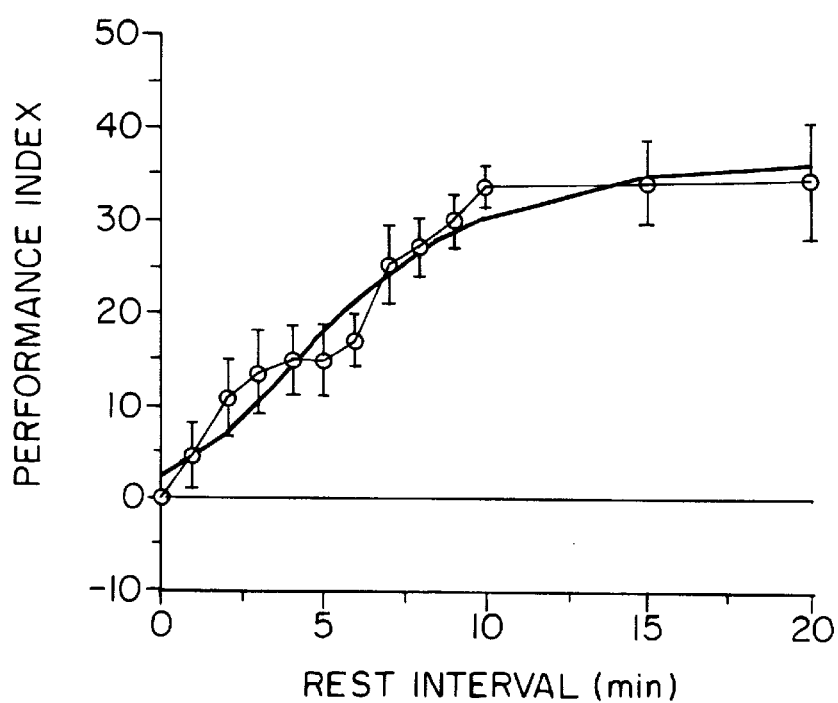
FIG. 13B is a graphic representation of results showing the effect of the rest interval between each training session on seven-day memory retention (long term memory) in wildtype (Can-S) flies with long term memory as a function of the rest interval indicated by open circles and a negative accelerating exponential Gompertz (growth) function fit to the individual performance indexes (PIs) using a nonlinear iterative least squares method indicated by the solid line.

LTM as a function of the length of the rest interval between 10 spaced training sessions was then assessed. FIG. 13B reveals a continuous increase in LTM from a 0-min rest interval (massed training) to a 10-min rest interval, at which time LTM levels reach maximum. Longer rest intervals yielded similar memory scores. These observations of LTM formation suggest an underlying biological process, which changes quantitatively during the rest interval between sessions and which accumulates over repeated training sessions.

In transgenic flies, the formation of LTM, but not ARM or any other aspect of learning or memory, is disrupted by induced expression of a repressor form of the cAMP-responsive transcription factor CREB (Example 4). Mutating two amino acids in the "leucine zipper" dimerization domain of this CREB repressor was sufficient to prevent the dominant-negative effect on LTM. Thus, indication of LTM is not only protein synthesis-dependent but also is CREB-dependent. Stated more generally, CREB function is involved specifically in a form of a memory that is induced only by spaced training. This observation was particularly intriguing in light of the molecular nature of CREB.

In Drosophila, transcriptional and/or post-translational regulation of dCREB2 yields several mRNA isoforms. Transient transfection assays in mammalian F9 cells have demonstrated that one of these isoforms (CREB2-a) functions as a cAMP-responsive activator of transcription, while a second isoform (CREB2-b) acts as an antagonistic repressor of the activator (Example 1; cf. Habener 1990; Foulkes and Sassone-Corsi 1992). (This repressor isoform was used previously to generate the inducible transgene mentioned above.) The existence of different CREB isoforms with opposing functions suggested an explanation for the requirement of multiple training sessions with a rest interval between them for the formation of LTM.

Figure 14:
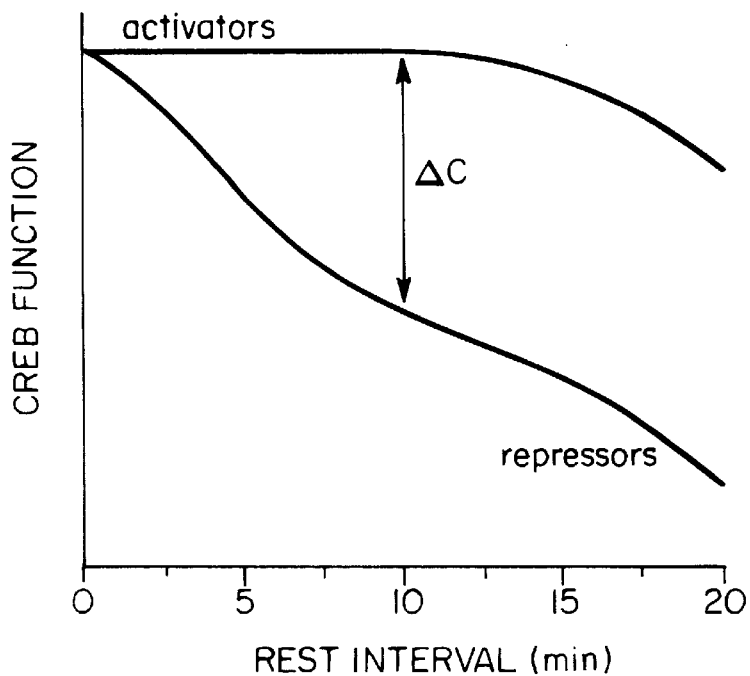
FIG. 14 depicts a conceptual model of a molecular switch for the formation of long term memory based on differential regulation of CREB isoforms with opposing functions with ΔC indicating the net effect of CREB activators.

In its simplest form, this model (Example 7; FIG. 14) supposes that cAMP-dependent protein kinase (PKA), activated during training, induces the synthesis and/or function of both CREB activator and repressor isoforms (cf. Yamamoto et al. 1988; Backsai et al. 1993). Immediately after training, enough CREB repressor exists to block the ability of CREB activator to induce downstream events. Then, CREB repressor isoforms are inactivated faster than CREB activator isoforms. In this manner, the net amount of functional activator ($\Delta C$=CREB2a-CREB2b) increases during a rest interval and then accumulates over repeated training sessions (with a rest interval) to induce further the downstream targets involved with the formation of LTM (Montarolo et al. 1986; Kaang et al. 1993).

Figure 15A:
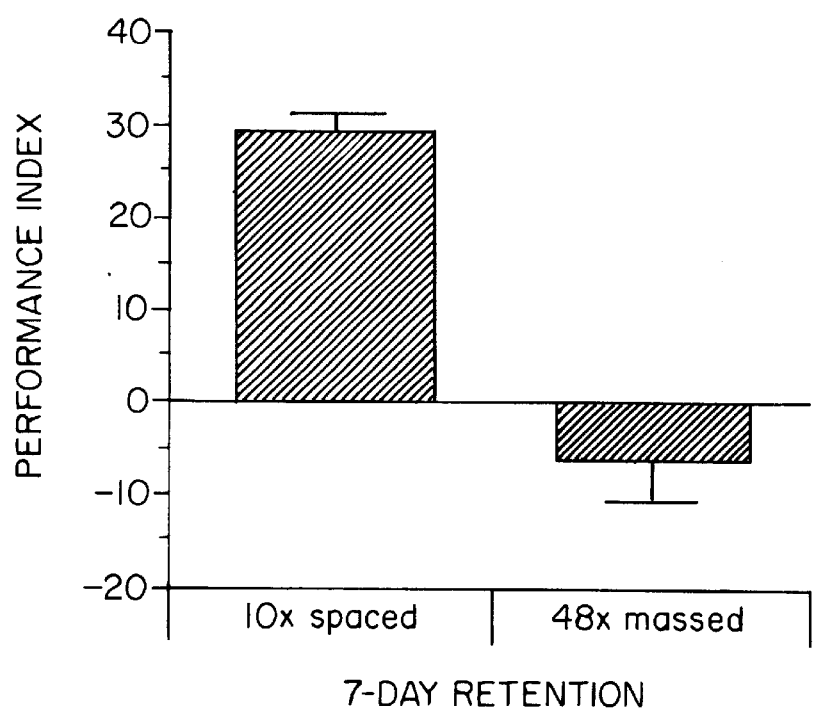
FIG. 15A is a bar graph representation of results showing the effect of 48 massed training sessions (48× massed) or 10 spaced training sessions with a 15-minute rest interval (10× spaced) on seven-day memory retention in wildtype (Can-S) flies.
Figure 15B:
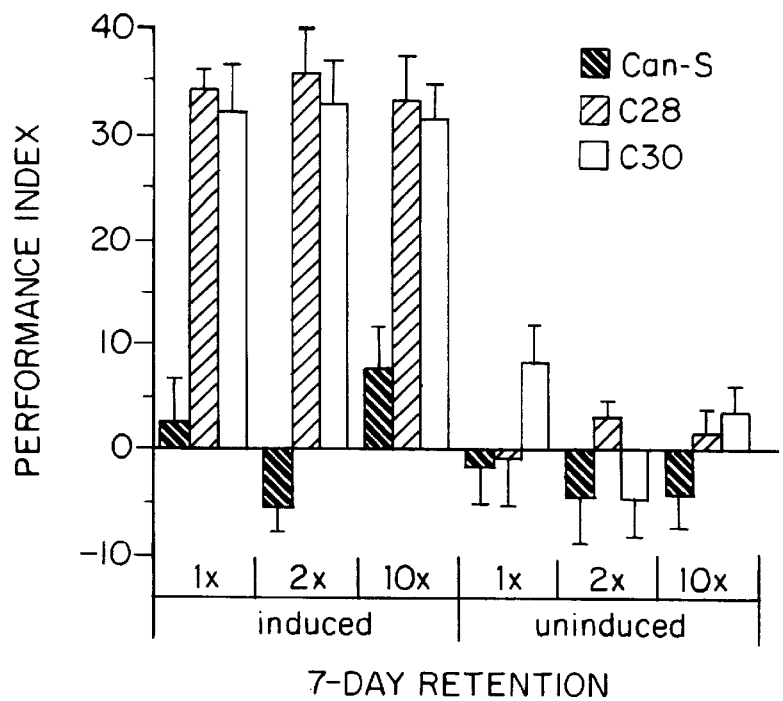
FIG. 15B is a bar graph representation of results showing the effect of one (1×), two (2×) or ten (10×) massed training sessions, three hours after heat-shock induction of the transgene (induced) or in the absence of heat-shock (uninduced), on seven-day memory retention in wildtype (Can-S) flies, hsp-dCREB2-a transgenic (C28) flies, and hsp-dCREB2-a transgenic (C30) flies: forward striped bars=wildtype (Can-S) flies; back striped bars=hsp-dCREB2-a transgenic (C28) flies; and white bars=hsp-dCREB2-a transgenic (C30) flies.

This model leads to three predictions, which have been confirmed. First, if the functional difference between CREB activator and repressor isoforms is zero ($\Delta C$=0) immediately after one training session, then additional massed training sessions should never yield LTM. FIG. 15A shows that 48 massed training sessions, rather than the usual 10, still does not produce any 7-day memory retention. Second, if the amount of CREB repressor is increased experimentally, $\Delta C$ will be negative immediately after training ($\Delta C<0$). Then, enough CREB repressor may not decay during a rest interval to free enough CREB activator for induction of LTM. This has been shown to be the case for spaced training (15-min rest interval) after inducing the expression of a hsp-dCREB2-b (repressor) transgene three hours before training (Example 4). Third, if the amount of CREB activator is increased experimentally, $\Delta C$ will be positive immediately after training ($\Delta C>0$). This effect, then, should eliminate or reduce the rest interval required to induce LTM. FIG. 15B shows the results from recent experiments in which the expression of a hsp-dCREB2-a (activator) transgene was induced three hours before training. In these transgenic flies, massed training produced maximal LTM. This effect appeared not to arise trivially, since olfactory acuity, shock reactivity (FIG. 15C) and initial learning were normal in transgenic flies after heat shock-induction. Thus, the requirement for a rest interval between training sessions to induce LTM specifically was eliminated.

FIG. 15B also shows that maximal LTM occurred in induced hsp-dCREB2-a transgenic flies after just one training session. The usual requirement for additional training to form a strong, long-lasting memory was no longer necessary. Thus, induced overexpression of a CREB activator has produced in otherwise normal flies, the functional equivalent of a "photographic" memory. This result indicates that the amount of CREB activator present during training—rather than the amount of activated PKA that reaches CREB in the nucleus, for instance (cf. Backsai et al. 1993; Kaang et al. 1993; Frank and Greenberg 1994)—is the rate-limiting step of LTM formation. Taken together, results from these experiments support the notion that the opposing functions of CREB activators and repressors act as a "molecular switch" (cf. Foulkes et al. 1992) to determine the parameters of extended training (number of training sessions and rest interval between them) required to form maximum LTM.

To date, seven different dCREB2 RNA isoforms have been identified, and more are hypothesized to exist. Each may be regulated differentially at transcriptional (Meyer et al. 1993) and/or translation levels before or during LTM formation. In addition, different combinations of CREB isoforms may exist in different (neuronal) cell types. Consequently, many different combinations of activator and repressor molecules are possible. From this perspective, the notions that all activators and repressors are induced during a training session or that all repressors inactivate faster than activators (see above) need not be true. Instead, the model requires only that $\Delta C$ (the net function of activators and repressors) is less than or equal to zero immediately after training and the increases with time (rest interval).

Theoretically, particular combinations of activator and repressor molecules in the relevant neuron(s) should determine the rest interval and/or number of training sessions necessary to produce maximum LTM for any particular task or species. Thus, the molecular identification and biochemical characterization of each CREB activator and repressor isoform used during LTM formation in fruit flies is the next major step toward establishing the validity of our proposed model. Similar experiments in other species may establish its generality.

CREB certainly is not involved exclusively with LTM. The dCREB2 gene, for instance, is expressed in all fruit fly cells and probably acts to regulate several cellular events (Foulkes et al. 1992).

So, what defines the specificity of its effects on LTM? Specificity most likely resides with the neuronal circuitry involved with a particular learning task. For olfactory learning in fruit flies, for instance, CREB probably is modulated via the cAMP second messenger pathway. Genetic disruptions of other components of this pathway are known to affect olfactory learning and memory (Livingstone et al. 1984; Drain et al. 1991; Levin et al. 1992; Skoulakis et al. 1993; Qiu and Davis 1993). Presumably, the stimuli used during conditioning (training) stimulate the underlying neuronal circuits. The cAMP pathway is activated in (some) neurons participating in the circuit, and CREB-dependent regulation of gene expression ensues in the "memory cells". This neurobiological perspective potentially will be established in Drosophila by identifying the neurons in which LTM-specific CREB function resides. Experiments using a neuronal co-culture system in Aplysia already have contributed significantly to this issue (Alberini et al. 1994 and references therein).

The involvement of CREB in memory, or in the structural changes of neurons which underlie memory in vivo, also has been implicated in mollusks (Dash et al. 1990; Alberini et al. 1994) and in mice (Bourtchuladze et al. 1994). Ample evidence also exists for the involvement of the cAMP second messenger pathway in associative learning in Aplysia (Kandel et al. 1987; Byrne et al. 1993) and in rat hippocampal long-term potentiation (LTP), a cellular model of associative learning in vertebrates (Frey et al. 1993; Huang and Kandel 1994). Finally, cellular and biochemical experiments have suggested that CREB function may be modulated by other second messenger pathways (Dash et al. 1991); Ginty et al. 1994; deGroot et al. 1994). These observation suggest that CREB might act as a molecular switch for LTM in many species and tasks.

Finally, why might the formation of LTM require a molecular switch? Many associative events occur only once in an animal's lifetime. Forming long-term memories of such events would be unnecessary and if not counterproductive. Instead, discrete events experienced repeatedly are worth remembering. In essence, a recurring event comprises a relevant signal above the noise of one-time events. Teleologically, then, the molecular switch may act as an information filter to ensure that only discrete but recurring events are remembered. Such a mechanism would serve efficiently to tailor an individual's behavioral repertoire to its unique environment.

The present invention also relates to isolated DNA having sequences which encode (1) a cyclic 3',5'-adenosine monophosphate (cAMP) responsive transcriptional activator, or a functional fragment thereof, or (2) an antagonist of a cAMP responsive transcriptional activator, or a functional fragment thereof, or (3) both an activator and an antagonist, or functional fragments thereof of both.

The invention relates to isolated DNA having sequences which encode Drosophila dCREB2 isoforms, or functional analogues of a dCREB2 isoform. As referred to herein, a functional analogue of a dCREB2 isoform comprises at least one function characteristic of a Drosophila dCREB2 isoform, such as a cAMP-responsive transcriptional activator function and/or an antagonistic repressor of the cAMP activator function. These functions (i.e., the capacity to mediate PKA-responsive transcription) may be detected by standard assays (e.g., assays which monitor for CREB-dependent activation). For example, assays in F9 cells have been used extensively to study CREB-dependent activation because their endogenous cAMP-responsive system is inactive (28, 49, 50).

The invention further relates to isolated DNA having sequences which encode a Drosophila dCREB2 gene or a functional fragment thereof. Isolated DNA meeting these criteria comprise nucleic acids having sequences identical to sequences of naturally occurring Drosophila dCREB2 and portions thereof, or variants of the naturally occurring sequences. Such variants include mutants differing by the addition, deletion or substitution of one or more nucleic acids.

The invention relates to isolated DNA that are characterized by (1) their ability to hybridize to a nucleic acid having the DNA sequence in FIG. 1A (SEQ ID NO.: 1) or its complement, or (2) by their ability to encode a polypeptide of the amino acid sequence in FIG. 1A (SEQ ID NO.: 2) or functional equivalents thereof (i.e., a polypeptide which functions as a cAMP responsive transcriptional activator), or (3) by both characteristics. In one embodiment, the percent amino acid sequence similarity between the polypeptide of FIG. 1A and functional equivalents thereof is at least about 55% ($\geq$55%). In a preferred embodiment, functional equivalents of the polypeptide of FIG. 1A share at least about 60% sequence similarity with the polypeptide of FIG. 1A. More preferably, the percent amino acid sequence similarity between the polypeptide of FIG. 1A and functional equivalents thereof is at least about 70%, and still more preferably, at least about 75%. Isolated nucleic acids meeting these criteria comprise nucleic acids having sequences homologous to sequences of mammalian CREB, CREM and ATF-1 gene products. Isolated nucleic acids meeting these criteria also comprise nucleic acids having sequences identical to sequences of naturally occurring dCREB2 or portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds, Vol. 1, Suppl. 26, 1991), the teachings of which are incorporated herein by reference. Factors such as probe length, base composition, percent mismatch between the hybridizing sequences, temperature and ionic strength influence the stability of nucleic acid hybrids. Thus, high or moderate stringency conditions can be deterimined empirically, depending in part upon the characteristics of the known DNA to which other unknown nucleic acids are being compared for homology.

Isolated nucleic acids that are characterized by their ability to hybridize to a nucleic acid having the sequence in FIG. 1A or its complement (e.g., under high or moderate stringency conditions) may further encode a protein or polypeptide which functions as a cAMP responsive transcriptional activator.

The present invention also relates to isolated DNA having sequences which encode an enhancer-specific activator, or a functional fragment thereof.

The invention further relates to isolated DNA having sequences which encode a Drosophila dCREB1 gene or a functional fragment thereof. Isolated DNA meeting these criteria comprise nucleic acids having sequences identical to sequences of naturally occurring Drosophila dCREB1 and portions thereof, or variants of the naturally occurring sequences. Such variants include mutants differing by the addition, deletion or substitution of one or more nucleic acids.

The invention further relates to isolated DNA that are characterized by (1) their ability to hybridize to a nucleic acid having the DNA sequence in FIG. 5 (SEQ ID NO.: 7) or its complement, or (2) by their ability to encode a polypeptide of the amino acid sequence in FIG. 5 (SEQ ID NO.: 8), or by both characteristics. Isolated DNA meeting these criteria also comprise nucleic acids having sequences identical to sequences of naturally occurring dCREB1 or portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated under high stringency conditions or moderate stringency conditions as described above, for example.

Fragments of the isolated DNA which code for polypeptides having a certain function can be identified and isolated by, for example, the method of Jasin, M., et al., U.S. Pat. No. 4,952,501.

Nitric Oxide in Invertebrates: Drosophila dNOS Gene Codes for a $Ca^{2+}$/Calmodulin-Dependent Nitric Oxide Synthase Nitric oxide (NO) is a gaseous mediator of a wide variety of biological processes in mammalian organisms. Applicants have cloned the Drosophila gene, dATOS, coding for a $Ca^{2+}$/calmodulin-dependent nitric oxide synthase (NOS). Presence of a functional NOS gene in Drosophila provides conclusive evidence that invertebrates synthesize NO and presumably use it as a messenger molecule. Furthermore, conservation of an alternative RNA splicing pattern between dNOS and vertebrate neuronal NOS, suggests broader functional homology in biochemistry and/or regulation of NOS.

NO is synthesized by nitric oxide synthases (NOSs) during conversion of L-arginine to L-citrulline (1). Biochemical characterization of NOSs has distinguished two general classes: (i) constitutive, dependent on exogenous $Ca^{2+}$ and calmodulin and (ii) inducible, independent of exogenous $Ca^{2+}$ and calmodulin. Analyses of cDNA clones have identified at least three distinct NOS genes in mammals (2, 3, 4, 5) neuronal, endothelial and macrophage, the former two of which are constitutive and the latter of which is inducible. The nomenclature for these different isoforms used here is historical, as it is clear now that one or more isoforms can be present in the same tissues (6).

As a diffusible free-radical gas, NO is a multifunctional messenger affecting many aspects of mammalian physiology [for reviews, see (7)]. NO originally was identified as an endothelium-derived relaxing factor responsible for regulation of vascular tone (8) and as a factor involved with macrophage-mediated cytotoxicity (9). Since NO has been implicated in several physiological processes including inhibition of platelet aggregation, promotion of inflammation, inhibition of lymphocyte proliferation and regulation of microcirculation in kidney (10). More recently, NO also has been shown to play a role in cell—cell interactions in mammalian central and peripheral nervous systems—in regulating neurotransmitter release, modulation of NMDA receptor-channel functions, neurotoxicity, nonadrenergic noncholonergic intestinal relaxation (11) and activity-dependent regulation of neuronal gene expression (12). Recent reports of NO function in synaptogenesis and in apoptosis during development of the rat CNS (13) suggest that NO regulates activity-dependent mechanism(s) underlying the organization of fine-structure in the cortex (14). NO also appears to be involved with long-term potentiation in hippocampus and long-term depression in cerebellum, two forms of synaptic plasticity that may underlie behavioral plasticity (15). Consistent with these cellular studies, inhibition of NOS activity has been shown to disrupt learning and memory (16).

Many of the above conclusions are based on pharmacological studies using inhibitors of nitric oxide synthases or donors of NO. Interpretations of such studies usually are limited because the drugs interact with more than one target and they cannot be delivered to specific sites. A molecular genetic approach can overcome these problems, however, by disrupting a specific gene, the product of which may be one of the drug's targets. Recently, such an approach has been attempted in mice via generation of a knock-out mutation of the neuronal NOS (nNOS) (17). While nNOS mutants appeared fully viable and fertile, minor defects in stomach morphology and hippocampal long-term potentiation were detected (17, 18). Moreover, some NOS enzymatic activity still was present in certain regions of the brain, suggesting a role for other NOS genes in the CNS. While yielding some relevant information about one specific component of NO function, this nNOS disruption existed throughout development. Consequently, functional defects of NOS disruption in adults could not be resolved adequately from structural defects arising during development. Genetic tools exist in Drosophila, in contrast, to limit disruptions of gene functions temporally or spatially.

To identify candidate Drosophila NOS homologs, a fragment of the rat neuronal NOS CDNA (2) was hybridized at low stringency to a phage library of the Drosophila genome as described in Example 11 (19). The rat cDNA fragment encoded the binding domains of FAD and NADPH (amino acids 979–1408 of SEQ ID NO.: 11), which are cofactors required for NOS activity, and therefore were expected to be conserved in fruit flies. Several Drosophila genomic clones were identified with the rat probe and classified into eight contigs. Sequence analysis of three restriction fragments from these genomic clones revealed one (2.4R) with high homology to mammalian NOSs. The deduced amino acid sequence of the ORF encoded within the 2.4R fragment indicated 40% identity to the rat neuronal NOS and binding sites for FAD and NADPH.

The 2.4R DNA fragment then was used to probe a Drosophila adult head cDNA library as described in Example 11 (19), and eight clones were isolated. Restriction analysis indicated that all contained identical inserts and thus, defined a predominant transcript expressed by this Drosophila gene. One clone (c5.3) was sequenced in both directions. The 4491 bp cDNA contained one long ORF of 4350 bp. The methionine initiating this ORF was preceded by ACAAG which is a good match to the translation start consensus (A/CAAA/C) for Drosophila genes (20). Conceptual translation of this ORF yielded a protein of 1350 amino acids with a molecular weight of 151,842 Da.

Comparison of the amino acid sequence of this deduced Drosophila protein (DNOS) (SEQ ID NO.: 9) to sequences of mammalian NOSs revealed that DNOS is 43% identical to neuronal NOS (SEQ ID NO.: 11), 40% identical to endothelial NOS (SEQ ID NO.: 10) and 39% identical to macrophage NOS (SEQ ID NO.: 12). It also revealed similar structural motifs in DNOS (FIGS. 16A–16C). The C-terminal half of the DNOS protein contains regions of high homology corresponding to the presumptive FMN-, FAD- and NADPH-binding sites. Amino acids thought to be important for making contacts with FAD and NADPH in mammalian NOSs (2, 3, 4, 5) are conserved in DNOS. The middle section of DNOS, between residues 215 and 746 of SEQ ID NO.: 9, showed the highest similarity to mammalian NOSs: it is 61% identical to the neuronal isoform and 53% identical to endothelial and macrophage isoforms. Sequences corresponding to the proposed heme- and calmodulin-binding sites in mammalian enzymes are well-conserved in DNOS. The region located between residues 643–671 of SEQ ID NO.: 9 has the characteristics of a calmodulin-binding domain (basic, amphiphilic α-helix) (21). The amino acid sequence between these two sites is very well conserved among all four NOS proteins, suggesting the location of functionally important domains such as the arginine-binding site (3), tetrahydrobiopterine cofactor binding site or a dimerization domain. DNOS also has a PKA consensus site (22) (at Ser-287 of SEQ ID NO.: 9) in a position similar to neuronal and endothelial NOSs.

The 214 amino acid N-terminal domain of DNOS shows no obvious homology to its equivalent portion of neuronal NOS or to the much shorter N-terminal domains of endothelial and macrophage NOSs. This region of DNOS contains an almost uninterrupted homopolymeric stretch of 24 glutamine residues. Such glutamine-rich domains, found in many Drosophila and vertebrate proteins, have been implicated in protein-protein interactions regulating the activation of transcription (23). Thus, this domain of DNOS could be involved with protein—protein interactions necessary for localization and/or regulation of DNOS activity.

Figure 16D:
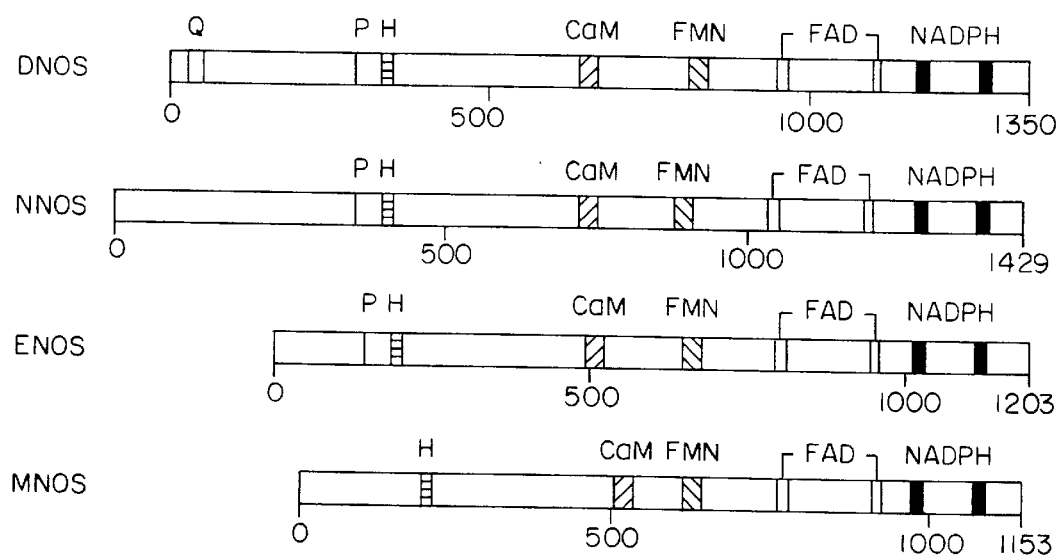
FIG. 16D is a schematic diagram of the domain structure of Drosophila and mammalian NOS proteins with the proposed cofactor-binding sites for heme (H), calmodulin (CaM), flavin mononucleotide (FMN), flavin adenine dinucleotide (FAD), nicotinamide adenine dinucleotide phosphate (NADPH) and the glutamine-rich domain (Q) in DNOS shown.

The above sequence comparisons suggest that a Drosophila structural homolog of a vertebrate NOS gene was identified. The order of the putative functional domains in the DNOS protein is identical to that of mammalian enzymes (FIG. 16D). Structural predictions based on several protein algorithms also indicate that general aspects of DNOS protein secondary structure (hydrophobicity plot, distribution of α-helixes and β-strands) from the putative heme-binding domain to the C-terminus are similar to those of mammalian NOSs. DNOS also does not contain a transmembrane domain, as is the case for vertebrate NOSs. In addition to these general characteristics, several aspects of DNOS structure actually render it most like neuronal NOS: (i) the overall sequence similarity, (ii) the similarity of the putative calmodulin-binding site (55% identical to the neuronal NOS vs. 45% identical to endothelial NOS or vs. 27% identical to macrophage NOS) and (iii) the large N-terminal domain. Neuronal NOS and DNOS also do not contain sites for N-terminal myristoylation, which is the case for endothelial NOS (3), nor do they have a deletion in the middle of the protein, which is the case for macrophage NOS (5).

Figure 17A:
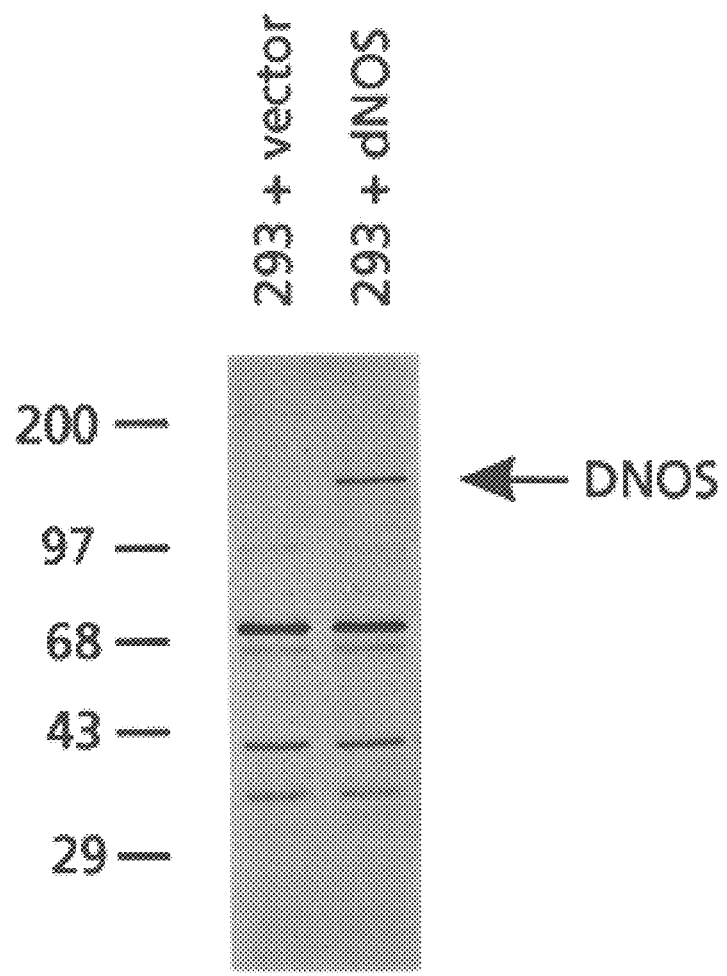
FIG. 17A is a photograph of a Western blot showing DNOS expression in 293 human embryonic kidney cells.

To establish that Applicants putative DNOS protein had nitric oxide synthase activity, the dNOS cDNA was expressed in 293 human embryonic kidney cells as described in Example 12 (24), which have been used routinely in studies of mammalian NOSs (2). Protein extracts prepared from dNOS-transfected 293 cells as described in Example 12, contained a 150 kD polypeptide, which was recognized by a polyclonal antibody raised against the N-terminal domain of DNOS (FIG. 17A, lane 293+dNOS) (25). This immunoreactive polypeptide was of a size expected for DNOS and was absent from cells transfected with just the PCGN vector alone (FIG. 17A, lane 293+ vector).

Figure 17B:
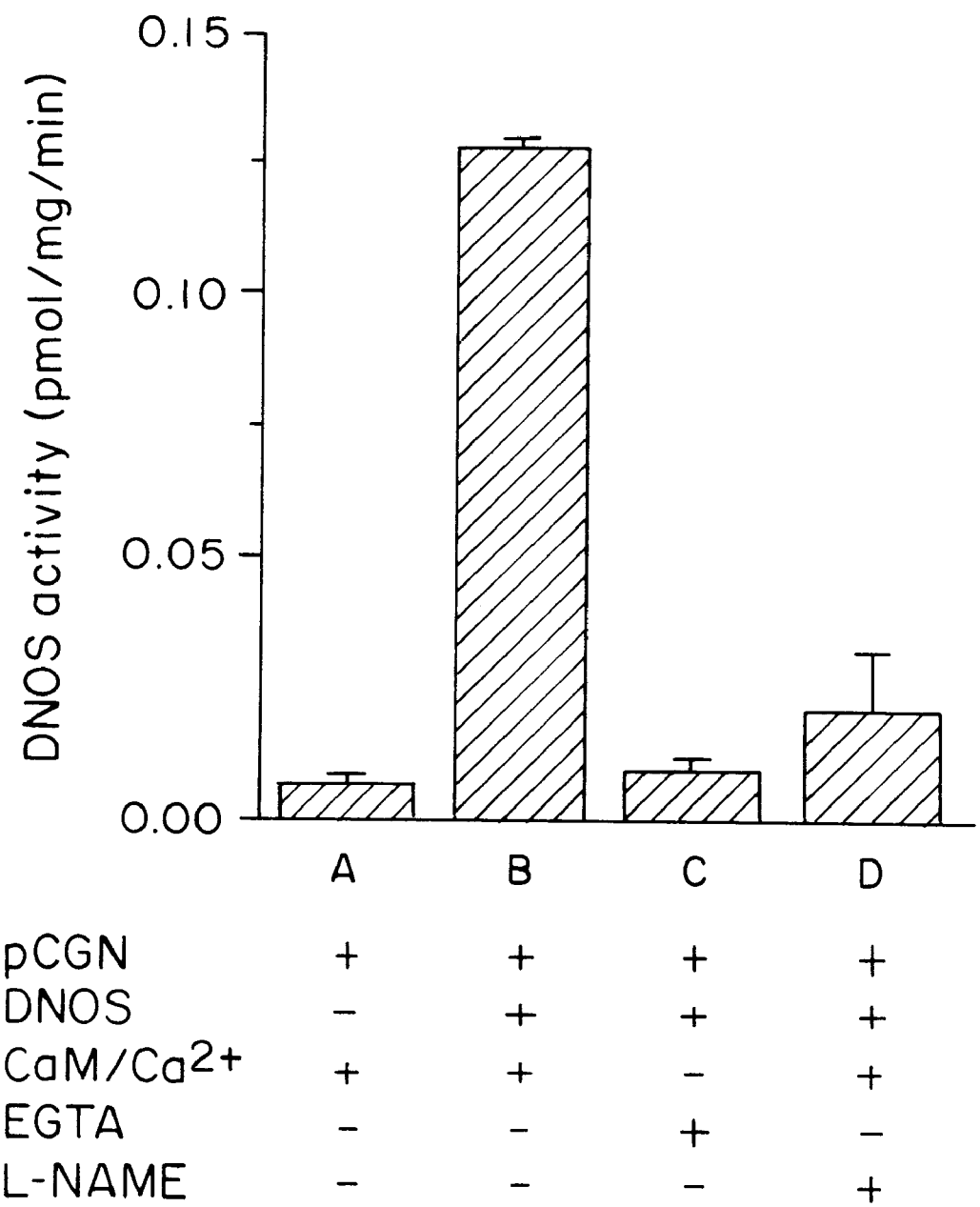
FIG. 17B is a bar graph representation of results showing DNOS enzyme activity measured in 293 human embryonic kidney cell extracts by conversion of $^3$H-L-arginine to $^3$H-L-citrulline: in the presence of exogenous $Ca^{2+}$ or calmodulin (group B); in the presence of 1 mM EGTA without exogenous $Ca^{2+}$ or calmodulin (group C); in the presence of 100 mM L-NAME with exogenous $Ca^{2+}$ or calmodulin (group D).

Extracts made from dNOS-transfected 293 cells showed significant NO synthase activity, as measured by the L-arginine to L-citrulline conversion assay as described in Example 12 (26) (0.1276±0.002 pmol/mg/min; FIG. 17B, group B). [In a parallel experiment, the specific activity of rat neuronal NOS expressed from the same vector in 293 cells was 3.0±0.02 pmol/mg/min, N=4]. DNOS activity was dependent on exogenous $Ca^{2+}$/calmodulin and on NADPH, two cofactors necessary for activity of constitutive mammalian NOSs (27, 28). DNOS activity was reduced 90% by the $Ca^{2+}$ chelator EGTA (FIG. 17B, group C). Also, 500 μM N-(6-aminohexyl)-1-naphthalene-sulfonamide (W5), a calmodulin antagonist which inhibits activity of neuronal NOS (28), diminished DNOS activity to 18% (0.0222±0.001 pmol/mg/min, N=2). In the absence of exogenous NADPH, DNOS (or nNOS) activity was reduced 20% (0.1061±0.011 pmol/mg/min, N=4 for DNOS; 2.7935±0.033 pmol/mg/min, N=2 for nNOS). DNOS activity also was blocked by inhibitors of mammalian NOSs (29). $N^G$-nitro-L-arginine methyl ester (L-NAME) reduced DNOS activity 84% (FIG. 17B, group D), and 100 μM $N^G$-monomethyl-L-arginine acetate produced a complete block (0.0001±0.0002 pmol/mg/min, N=2). These enzymatic data demonstrate that DNOS is a $Ca^{2+}$/calmodulin-dependent nitric oxide synthase.

Figure 18A:
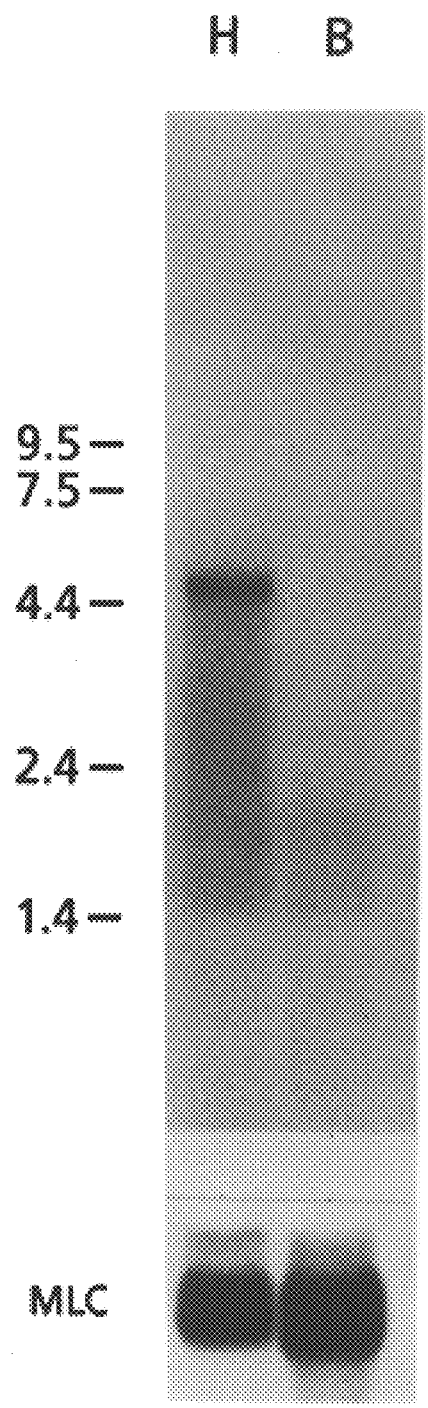
FIG. 18A is a photomicrograph of a Northern blot showing a 5.0 kb dNOS transcipt present in Drosophila heads: H=head; B=body.
Figure 18B:
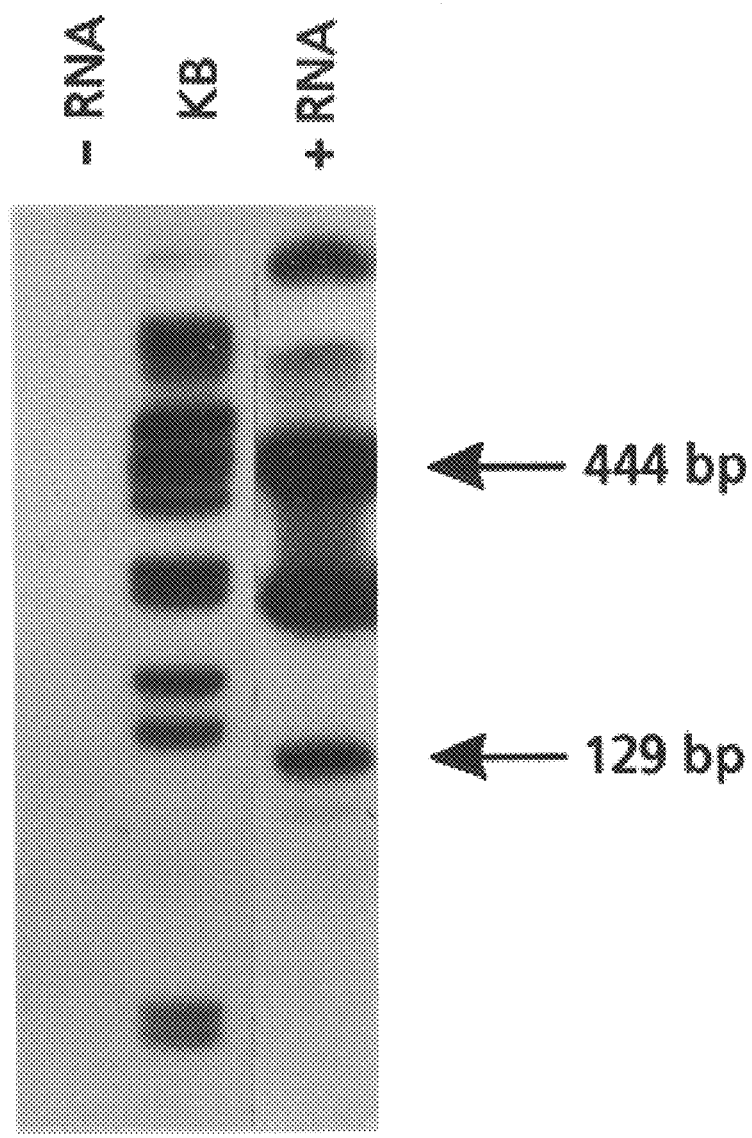
FIG. 18B is a photograph of an agarose gel stained with ethidium bromide showing the expression by the dNOS gene of two alternatively spliced mRNA species with the arrows indicating the positions of the DNA fragments of the expected sizes: the 444 bp long-form fragment and the 129 bp short-form fragment. The other bands present in the lane are artifacts from heteroduplexes that failed to denature. KB=size markers.
Figure 18C:
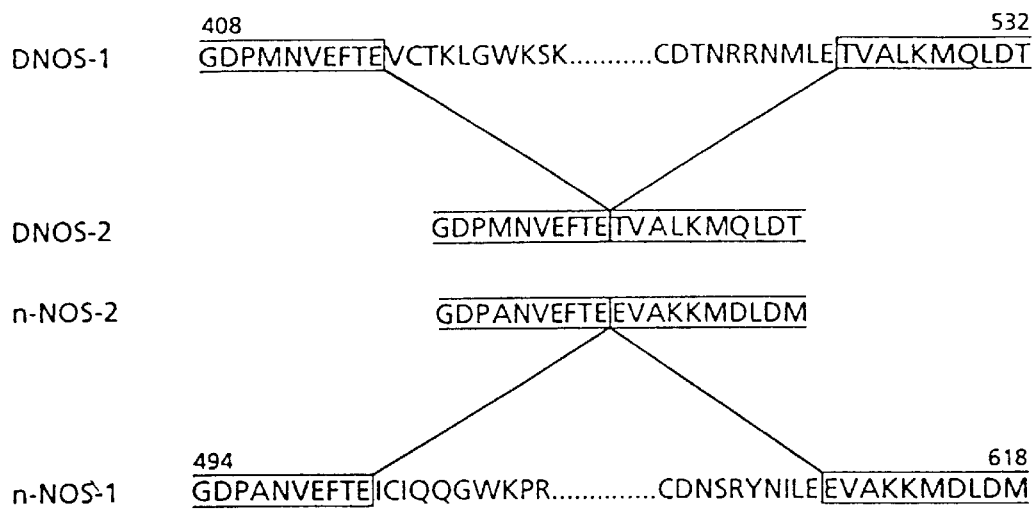
FIG. 18C depicts the alignment of the deduced amino acid sequence of two protein isoforms of DNOS and mouse neuronal NOS: top part shows the relation between two conceptual Drosophila NOS proteins, DNOS-1 (amino acid residues 408–427 and 513–532 of SEQ ID NO.: 9) and DNOS-2 (SEQ ID NO.: 14), corresponding to the longer and shorter RT-PCR products, respectively; the bottom part shows the relationship between the relevant regions of two protein isoforms of the mouse neuronal NOS, n-NOS-1 (amino acid residues 494–513 and 599–618; SEQ ID NO.:13 and SEQ ID NO.: 15, respectively) and n-NOS-2 (SEQ ID NO.: 16); and the numbers indicate the positions of the amino acid residues relative to the first methionine in the respective OFRs.

Northern blot analysis indicated a 5.0 kb dNOS transcript which was expressed predominantly in adult fly heads but riot bodies (FIG. 18A). More sensitive RT-PCR experiments as described in Example 13 (30), however, detected dNOS message in poly(A)$^+$ RNA from fly bodies. Neuronal NOS genes from mice and humans produce two alternatively spliced transcripts, the shorter one of which yields a protein containing a 105 amino acid in-frame deletion (residues 504–608 in mouse or rat neuronal NOS) (31). RT-PCR amplification of Drosophila head mRNA produced two DNA fragments: the 444 bp fragment corresponded to vertebrate long form and the 129 bp fragment corresponded to vertebrate short form (FIG. 18B). Conceptual translation of the 129 bp sequence confirmed a splicing pattern identical to that for the nNOS gene (FIG. 18C). Presence of the short NOS isoform in Drosophila strengthens the notion that it may play an important role in NOS biochemistry.

The discovery of a NOS homolog in Drosophila provides definitive proof that invertebrates produce NO and, as suggested by recent reports, most likely use it for intercellular signaling. These data also suggest that a NOS gene was present in an ancestor common to vertebrates and arthropods, implying that NOS has existed for at least 600 million years. Thus, it is expected that NOS genes are prevalent throughout the animal kingdom.

Consistent with this view are existing histochemical data. NOS activity has been detected in several invertebrate tissue extracts: in *Lymulus polyphemus* (32), in the locust brain (33), in the salivary gland of *Rhodnius prolixus* (34) and in various tissues of *Lymnaea stagnalis* (35). Applications of NOS inhibitors or NO-generating substances have been shown to modulate the activity of buccal motoneurones in Lymnaea stagnalis (35) and the oscillatory dynamics of olfactory neurons in procerebral lobe of Limax maximus (36). NADPH-diaphorase staining, a relatively specific indicator of NOS protein in fixed vertebrate tissue samples (37), also has suggested the presence of NOS in Drosophila heads (38). The present molecular cloning of dNOS considerably strengthens the validity of these observations.

Sophisticated genetic analyses of NOS function are available in Drosophila. Classical genetics will allow the creation of point mutations and deletions in dNOS, resulting in full or partial loss of dNOS function. Such mutations will permit detailed studies of the role of NOS during development.

Figure 3:
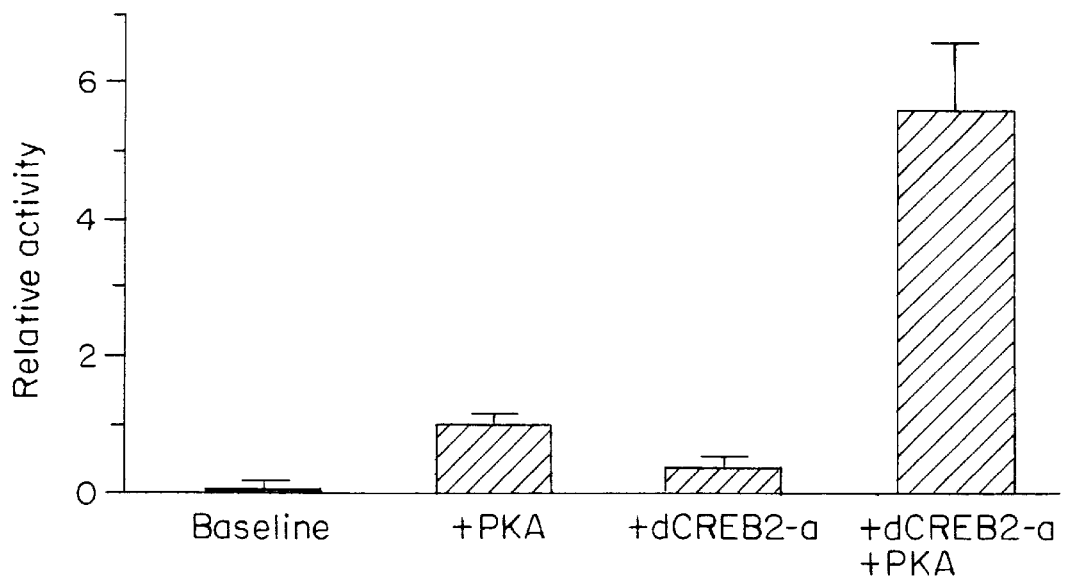
FIG. 3 is a bar graph representation of results showing pKA-responsive transcriptional activation by dCREB2-a.

The present further invention relates to isolated DNA that are characterized by by their ability to encode a polypeptide of the amino acid sequence in FIGS. 16A1–16A3 (SEQ ID NO.: 9) or functional equivalents thereof (i.e., a polypeptide which synthesizes nitric oxide). Isolated DNA meeting this criteria comprise amino acids having sequences homologous to sequences of mammalian NOS gene products (i.e., neuronal, endothelial and macrophage NOSs). Isolated DNA meeting these criteria also comprise amino acids having sequences identical to sequences of naturally occurring ciNOS or portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in Current Protocols in Molecular Biology (Ausubel, F. M. et al., eds, Vol. 1, Suppl. 26, 1991), the teachings of which are incorporated herein by reference. Factors such as probe length, base composition, percent mismatch between the hybridizing sequences, temperature and ionic strength influence the stability of nucleic acid hybrids. Thus, high or moderate stringency conditions can be deteriemined empirically, depending in part upon the characteristics of the known DNA to which other unknown nucleic acids are being compared for homology.

Isolated DNA that are characterized by their ability to encode a polypeptide of the amino acid sequence in FIGS. 16A–16C, encode a protein or polypeptide having at least one function of a Drosophila NOS, such as a catalytic activity (e.g., synthesis of nitric oxide) and/or binding function (e.g., putative heme, calmodulin, FMN, FAD and NADPH binding). The catalytic or binding function of a protein or polypeptide encoded by hybridizing nucleic acid may be detected by standard enzymatic assays for activity or binding (e.g., assays which monitor conversion of L-arginine to L-citrulline). Functions characteristic of dNOS may also be assessed by in vivo complementation activity or other suitable methods. Enzymatic assays, complementation tests, or other suitable methods can also be used in procedures for the identification and/or isolation of nucleic acids which encode a polypeptide having the amino acid sequence in FIGS. 16A–16C or functional equivalents thereof.

Complete citations for each of the references cited herein are provided after the examples. They are indicated in the text either by number or by author and year. List 1 is references for work relating to cloning and characterization of dCREB genes as described in Examples 1 and 2. List 2 is references for work relating to induction of dominant-negative CREB transgene and specific blocking of long-term memory, as described in Examples 3 and 4. List 3 is references for work relating to a molecular switch for long term memory, as described in Examples 5–10. List 4 is references for work relating to the dNOS gene, as described in Examples 11–13.

The present invention will now be illustrated by the following examples, which are not intended to be limiting in any way.

EXAMPLES

The following materials and methods were used in the work described in Examples 1 and 2.

Expression Cloning of dCREB1 and dCREB2

Standard protocols for expression cloning by DNA-binding (4, 66) were followed except as noted. A double-stranded, 3×CRE oligonucleotide was synthesized and cloned between the XbaI and KpnI sites of pGEM7Zf+ (Promega). The sequence of one strand of the oligonucleotide was 5' CGTCTAGATCTA<u>TGACTGAATA</u> <u>TGACGTAATATGACGTAA</u>TGGTACCAGATCTGGCC 3' (SEQ ID NO.: 17), with the CRE sites underlined. The oligonucleotide was excised as a BglII/HindIII fragment and labeled by filling-in the overhanging ends with Klenow fragment in the presence of [$\alpha^{32}$P]dGTP, [$\alpha^{32}$P]dCTP and unlabeled DATP and dTTP (4). Just prior to use, the labeled fragment was pre-absorbed to blank nitrocellulose filters to reduce background binding. All other steps were as described (4). After secondary and tertiary lifts, positive clones were subcloned into pKS+ (Stratagene) and sequences.

Gel Shift Analysis

Gel-mobility shift assays were performed as in (4) with the following modifications. The 4% polyacrylamide gel (crosslinking ratio 80:1) was cast and run using 5× Tris-glycine buffer (4) supplemented with 3 mM $MgCl_2$. The oligonucleotides used as the DNA probes were boiled and slowly cooled to room temperature at a concentration of 50 μg/ml in 0.1M NaCl. 50 ng of double-stranded probe was end-labeled using polynucleotide kinase in the presence of 100 μCi of [$\gamma^{32}$P]ATP. The double-stranded oligonucleotides were purified on a native polyacrylamide gel and used in a mobility shift assay at about 0.5 ng/reaction.

For dCREB2, the original dCREB2-b cDNA was subcloned and subjected to site-directed mutagenesis to introduce restriction sites immediately 5' and 3' of the open reading frame. This open reading frame was subcloned into the pET11A expression vector (Novagen) and used to induce expression of the protein in bacteria. The cells containing this vector were grown at 30° C. to an approximate density of $2 \times 10^8$/ml and heat-induced at 37° C. for 2 hours. The cells were collected by centrifugation and lysed according to (8). The crude extract was clarified by centrifugation and loaded onto a DEAE column previously equilibrated with 50 mM Tris HCl, pH 8.0, 10% sucrose, 100 mM KCl. Step elutions with increasing amounts of KCl in the same buffer were used to elute the dCREB2-b protein, which was assayed using the gel mobility-shift assay. The peak fraction was dialyzed against the loading buffer and used in the binding experiment. The specific competitor that was used was the wild-type CRE oligonucleotide. The sequence of one strand of the double-stranded oligonucleotides used in the gel shift analysis are listed. For the first two oligonucleotides, wild-type and mutant CREs are underlined.

Wild-type 3×CRE (SEQ ID NO.: 18):
5'AAA<u>TGACGTAA</u>CGGAAA<u>TGACGTAA</u>CGGAAA
<u>TGACGTAA</u>CG 3';

Mutant 3xmCRE (SEQ ID NO.: 19):
5'AAA<u>TGAATTAA</u>CGGAAA<u>TGAATTAA</u>CGGAAA<u>TGAATTAA</u>CGG 3';
Nonspecific competitor #1 (SEQ ID NO.: 20):
5'TGCACGGGTTTTCGACGTTCACTGG-TAGTGTCTGATGAGGCCGAAAGGCCGAAA CGCGATGCCCATAACCACCACGCTCAG 3';
Nonspecific competitor #2 (SEQ ID NO.: 21):
5'TCGACCCACAGTTTCGGGTTTTCGAG-CAAGTCTGCTAGTGTCTGATGAGGCCG AAAGGCCGAAACGCGAAGCCGTATTGCAC-CACGCTCATCGAGAAGGC 3';
Nonspecific competitor #3 (SEQ ID NO.: 22):
5'CTAGAGCTTGCAAGCATGCTTGCAAG-CAAGCATGCTTGCAAGCATGCTTG CAAGC 3';
Nonspecific competitor #4 (SEQ ID NO.: 23):
5'CTCTAGAGCGTACGCAAGCGTACGCAAGCGTACG 3'

For dCREB1, heat-induced bacterial extracts (4) were made from the original phage clone integrated by lysogeny. Extract from a bacteria lysogenized with another plaque (which did not bind to CRE sites) from the screen was used as a negative control. Competition experiments were done using a 4–100 fold molar excess (relative to the probe) of unlabeled, wild-type CRE oligonucleotides or unlabeled, mutant CRE oligonucleotides.

Northern Blots

Total head and body RNA was isolated from flies according to the protocol of (17). Total RNA from all other developmental stages was a gift from Eric Schaeffer. All RNA samples were selected twice on oligo-dT columns (5 Prime-3 Prime) to isolate poly A+ RNA. Two µg of poly A+ RNA was fractionated on 1.2% formaldehyde-formamide agarose gels, transferred to nitrocellulose and probed using an uniformly labeled, strand-specific, antisense RNA (aRNA) probe. The template for the synthesis of aRNA was one of the partial cDNA clones isolated from the library screen (pJY199). This cDNA contained the carboxyl-terminal 86 amino acids of the dCREB2-b protein and about 585 bp of 3' untranslated mRNA. All Northern blots were washed at high stringency (0.1% SDS, 0.1×SSC, 65° C.).

In situ Hybridization To Tissue Sections

Frozen frontal sections were cut and processed under RNAse-free conditions, essentially as described in (58), with modifications for riboprobes as noted here. Digoxigenin-labeled riboprobes were made from pJY199 using the Genius kit (Boehringer-Mannheim). One µg of Xba-linearized template and T3 RNA polymerase was used to make the antisense probe, while one µg of EcoRI-linearized template together with T7 RNA polymerase was used for the control sense probe. Alkaline hydrolysis (30 minutes at 60° C.) was used to reduce the average probe size to about 200 bases. The hydrolyzed probe was diluted 1:250 in hybridization solution (58), boiled, quickly cooled on ice, added to the slides and hybridized at 42° C. overnight. The slides were then treated with RNAse A (20 µg/ml RNAse A in 0.5M NaCl/10 mM Tris pH8 for 1 hour at 37° C.) prior to two 50° C. washes. Digoxigenin detection was as described.

Reverse Transcription Coupled With the Polymerase Chain Reaction (RT-PCR) Analysis of dCREB2 and Identification of Alternatively Spliced Exons The template for reverse transcription coupled with the polymerase chain reaction (RT-PCR) was total RNA or poly A+ RNA isolated from Drosophila heads as in (17). Total RNA used was exhaustively digested with RNase-free DNase I (50 µg of RNA digested with 50 units of DNase I for 60–90' at 37° C. followed by phenol, phenol/chloroform extraction, and ethanol precipitation) prior to use. Results from separate experiments indicate that this DNase-treatment effectively eliminates the possibility of PCR products derived from any contaminating genomic DNA. Two rounds of selection using commercial oligo-dT columns (5 Prime-3 Prime) were used to isolate poly A+ RNA from total RNA. The template for an individual reaction was either 100–200 ng of total RNA, or 10–20 ng of poly A+ RNA.

The RT-PCR reactions were performed following the specifications of the supplier (Perkin-Elmer) with a "Hot Start" modification (Perkin Elmer RT-PCR kit instructions). All components of the RT reaction, except the rTth enzyme, were assembled at 75° C., and the reaction was initiated by adding the enzyme and lowering the temperature to 70° C. At the end of 15 minutes, the preheated (to 75° C.) PCR components (including trace amounts of [$\alpha^{32}$P]dCTP) were added quickly, the reaction tubes were put into a pre-heated thermocycler, and the PCR amplification begun. Cycling parameters for reactions (100 µl total volume) in a Perkin-Elmer 480 thermocycler were 94° C. for 60 seconds, followed by 70° C. for 90 seconds. For reactions (50 µl) in an MJ Minicycler the parameters were 94° C. for 45 seconds and 70° C. for 90 seconds.

All primers used in these procedures were designed to have 26 nucleotides complementary to their target sequence. Some primers had additional nucleotides for restriction sites at their 5' ends to facilitate subsequent cloning of the products. Primers were designed to have about 50% GC content, with a G or C nucleotide at their 3' most end and with no G/C runs longer than 3. For RT-PCR reactions with a given pair of primers, the $Mg^{+2}$ concentration was optimized by running a series of pilot reactions, at $Mg^{+2}$ concentrations ranging from 0.6 mM to 3.0 mM. Reaction products were analyzed on denaturing urea-polyacrylamide gels by autoradiography. Any product that appeared larger than the band predicted from the cDNA sequence was purified from a preparative native gel, re-amplified using the same primers, gel-purified, subcloned and sequenced.

To verify that a given RT-PCR product was truly derived from RNA, control reactions were run to show that the appearance of the product was eliminated by RNase A treatment of the template RNA. Also, products generated from reactions using total RNA as the template were re-isolated from reactions using twice-selected polyA+RNA as template.

Plasmids

Expression constructs for transient transfection experiments in Drosophila were made in the expression vector pAct5CPPA (35) or in pAcQ. pAcQ is a close derivative of pAct5CPPA in which the XbaI site at the 5' end of the 2.5 kb actin promoter fragment was destroyed and additional sites were inserted in the polylinker. pAc-dCREB1 was made by subcloning a KpnI-SacI fragment containing the complete dCREB1 open reading frame (from a cDNA subcloned into pKS+) into pAct5CPPA. pAc-PKA was constructed by subcloning an EcoRV fragment encoding the Drosophila PKA catalytic subunit (23) from a modified pHSREM1 construct (17) into pAct5CPPA. To make the 3xCRE-lacZ reporter construct for Drosophila cell culture, the double-stranded, wild-type 3xCRE oligonucleotide used in the gel shift analysis was cloned into the KpnI-XbaI backbone of HZ50PL (37), a reporter construct made for enhancer testing which has cloning sites in front of a minimal hsp70 promoter-lacZ fusion gene.

RSV-dCREB.2-a was constructed in a long series of cloning steps. Details of the construction are available upon request. Essentially, the activator-encoding open reading frame was first reconstructed on the plasmid pKS+ by sequentially adding each of the three exons (exons 2, 4 and 6) into the original cDNA of dCREB2-b, which had been subcloned from phage DNA into pKS+. Site-directed mutagenesis was used to introduce unique restriction enzyme sites both 5' and 3' of the dCREB2-b open reading frame, and these sites facilitated the subcloning process and allowed removal of 5' and 3' untranslated sequences. Once the activator was assembled, the resulting open reading frame was sequenced to confirm the cloning steps and moved into a modified RSV vector which contained a polylinker located between the RSV promoter and the SV40 polyadenylation sequences (RSV-0). RSV-dCREB2-b was made by moving the original dCREB2-b cDNA (which had been subcloned into pKS+) into RSV-0.

Other constructs used in experiments were: pCaE (pMtC) (52), which contains the cDNA for mouse PKA catalytic subunit cloned under the mouse metallothionein 1 promoter; RSV-βgal (20), which expresses the lacZ gene under control of the Rous sarcoma long terminal repeat promoter (29); RSV-CREB (28) is a CREB cDNA fragment containing the 341-amino acid open reading frame under the RSV LTR-promoter in RSV-SG, and the D(−71) CAT reporter (56) which is a fusion of a CRE-containing fragment of the rat somatostatin promoter and the bacterial CAT coding region.

F9 Cell Culture and Transfection

Undifferentiated F9 cells were maintained and transfected using the calcium phosphate method as described in (12), except that chloroquine was added to 100 mM immediately before transfection and precipitates were washed off ten hours after transfection, at which time the dishes received fresh chloroquine-free medium. Amounts of DNA in transfections were made equivalent by adding RSV-0 where required. Cells were harvested 30 hours after transfection. Extracts were made by three cycles of freeze/thawing, with brief vortexing between cycles. Particulate matter was cleared from extracts by ten minutes of centrifugation in the cold. β-galactosidase assays were performed as described in (53). CAT assays were performed as described in (65) using aliquots of extract heat-treated at 65° C. for ten minutes and centrifuged for ten minutes to remove debris. Results reported are from three experiments run on different days with at least three dishes per condition within each experiment. Error bars represent standard error of the mean, with error propagation taken into account (30).

Drosophila Cell Culture and Transient Transfection

Schneider L2 cells in Schneider's medium (Sigma) supplemented with 10 μl fetal bovine serum (FBS) or Kc167 cells in D-22 medium (Sigma) supplemented with 10% FBS, were transfected by the calcium phosphate method essentially as described in (41), with the following differences. Kc167 cells were plated at $2 \times 10^6$ cells/ml and chloroquine was added to a final concentration of 100 mM immediately prior to transfection. We used a total of 10 μg of plasmid DNA per dish for L2 transfections and 25 μg per dish for Kc167 transfections. DNA masses in transfections were made equivalent with pGEM7Zf+ where required. Precipitates were left undisturbed on L2 cells until harvest, but for Kc167 cells the original medium was replaced with fresh, chloroquine-free medium after twelve hours. Cells were harvested thirty-six to forty-eight hours after transfection. Extracts were made and enzymatic assays performed as described above for F9 cells. Results reported for transfections are averages of at least three experiments run on different days, with at least duplicate dishes for each condition within experiments. Error bars represent standard error of the mean, with error propagation taken into account (30).

β-galactosidase (βgal) and Chloramphenicol Acetyl Transferase (CAT) Assays

β-galactosidase assays were run and activity calculated as described in (53). CAT assays were performed essentially according to (65) using supernatants from heat-treated aliquots of extracts (65° C. for 10 minutes and then centrifuged for 10 minutes). Relative activity was calculated according to (65).

PKA-Responsive Transcriptional Activation by dCREB2-a

F9 cells were transiently transfected with 10 μg of D(−71) CAT plasmid as a CRE-directed reporter. 5 μg of RSV-βgal reporter was included in each dish as a normalization control for transfection efficiency. Different groups received 8 μg of dCREB2-a expression vector and 4 μg of PKA expression vector, separately or in combination. Results are expressed as CAT/βgal enzyme activity ratios, standardized to values obtained with PKA-transfected dishes.

Transcriptional Effect of dCREB2-b and a Mutant Variant On PKA-Responsive Activation by dCREB2-a F9 cells were transiently cotransfected with 10 μg of D(−71) CAT along with the indicated combinations of the following expression constructs: RSV-dCREB2-a (5 μg); pMtC (2 μg); RSV-dCREB2-b (5 μg); and RSV-mLZ-dCREB2-b, which expresses a leucine-zipper mutant of dCREB2-b (5 μg). The DNA mass for each dish was made up to 27 μg with RSV-O. Other experimental conditions are as described above under "PKA-Responsive Transcriptional Activation by dCREB2-a".

Transcriptional Activation of a CRE Reporter Gene by dCREB1 in Drosophila Schneider L2 cell culture The cells were transiently transfected with a dCREB1 expression construct (1 μg), with or without a construct which expresses Drosophila PKA. 3×CRE-βgal reporter (1 μg) and the normalization Ac-CAT reporter (1 μg) were included in each dish. Expression vectors not present in particular dishes were replaced by pACQ.

Example 1

Isolation and Characterization of dCREB2

Two different genes were isolated in a DNA-binding expression screen of a Drosophila head cDNA library using a probe containing three CRE sites (3×CRE). Many clones were obtained for the dCREB2 gene, while only one clone was obtained for dCREB1. The dCREB2 clones had two alternatively-spliced open reading frames, dCREB2-b and dCREB2-c (see FIG. 2). These differed only in the presence or absence of exon 4 and in their 5' and 3' untranslated regions. The inferred translation product of dCREB2-b showed very high sequence similarity to the amino acid sequences of the basic region/leucine zipper (bZIP) domains of mammalian CREB (SEQ ID NO.: 4), CREM (SEQ ID NO.: 5) and ATF-1 (SEQ ID NO.: 6) (see FIG. 1B).

Chromosomal in situ hybridization using a dCREB2 probe localized the gene to a diffuse band at 17A2 on the X chromosome, a region which contains several lethal complementation groups (19).

To determine the DNA binding properties of dCREB2-b, the DNA binding activity of dCREB2-b was assayed using a gel mobility-shift assay. Bacterial extracts expressing the dCREB2-b protein retarded the migration of a triplicated CRE probe (3×CRE). The protein had lower, but detectable, affinity for a mutated 3×CRE oligonucleotide. Competition experiments using unlabeled competitor oligonucleotides showed that the binding of dCREB2-b to 3×CRE was specific with higher affinity for CRE sites than to nonspecific DNA. Together with the conserved amino acid sequence, this functional similarity suggested that dCREB2 was a CREB family member.

The expression pattern of dCREB2 was determined by Northern blot analysis of poly A+RNA from various developmental stages. A complex pattern with at least 12 different transcript sizes was found. Two bands of approximately 0.8 and 3.5 kb were common to all of the stages. The adult head contained transcripts of at least six sizes (0.8, 1.2, 1.6, 1.9, 2.3 and 3.5 kb). In situ hybridization to RNA in Drosophila head tissue sections showed staining in all cells. In the brain, cell bodies but not neuropil were stained.

dCREB2 has alternatively-spliced forms. Initial transfection experiments showed that the dCREB2-c isoform was not a PKA-responsive transcriptional activator. This information, together with the complex developmental expression pattern and the known use of alternative splicing of the CREM gene to generate PKA-responsive activators (24, 26) suggested that additional domains might be required to code for an activator.

Reverse transcription coupled with the polymerase chain reaction (RT-PCR) was used to identify new exons. Comparison of the genomic DNA sequence with that of cDNAs indicated the general exon/intron organization and assisted in the search for additional exons. Sense and antisense primers spaced across the dCREB2-b cDNA were synthesized and used pairwise in RT-PCR reactions primed with Drosophila head RNA. Reactions with primers in exons 5 and 7 (see FIG. 2) generated two products, one with the predicted size (compared with the cDNA clones) and one that was larger. The larger fragment was cloned and its sequence suggested the presence of exon 6 (see FIG. 1A; SEQ ID NO.: 1). A primer within exon 6 was synthesized, end-labeled and used to screen a Drosophila head cDNA library. Two clones were isolated, sequenced and found to be identical. This splicing isoform, dCREB2-d, confirmed the splice junctions and exon sequence inferred from the RT-PCR products.

Initial attempts to isolate exon 2 proved difficult. The genomic sequence that separated exons 1 and 3 (see FIG. 2) was examined and one relatively extensive open reading frame (ORF) was identified. Three antisense primers, only one of which lay inside this ORF, were synthesized based on the intron sequence. Three sets of RT-PCR reactions were run in parallel, each using one of the three antisense primers and a sense primer in exon 1. Only the reaction that used the antisense primer in the ORF produced a PCR product. The sequence of this product matched a continuous stretch of nucleotides from the genomic sequence, extending 3' from exon 1 past the splice junction in the dCREB2-b cDNA to the location of the antisense primer in the ORF. This fragment suggested that exon 1 might be extended in some mRNAs by use of an alternative 5' splice site located 3' to the site used to make dCREB2-b. Based on the newly-identified exon sequences, a sense primer was made. This primer was used with an antisense primer in exon 3 to generate a new product whose sequence established the location of the new 5' splice site. The sequence added to exon 1 by alternative 5' splice site selection is denoted exon 2. The exon 2 sequence also showed that the same 3' splice site was used both for the original cDNA and for exon 2. To independently verify this alternative splicing pattern, we carried out RT-PCR with a primer that spanned the 3' splice junction of exon 2 and a primer in exon 1. The sequence of the product corroborated the splice junctions of exon 2 shown in FIG. 1A (SEQ ID NO.: 1).

To determine if exons 2 and 6 could be spliced into the same molecule, we carried out an RT-PCR reaction with primers in exons 2 and 6. The reaction produced a product of the size predicted by coordinate splicing of these two exons and the identity of this product was confirmed by extensive restriction analysis.

dCREB2 is a Drosophila CREB/ATF gene. FIG. 1A shows the DNA sequence (SEQ ID NO.: 1) and inferred amino acid sequence (SEQ ID NO.: 2) of dCREB2-a, the longest ORF that can result from the identified alternative splicing events. The indicated translation start site for this ORF is probably authentic because: i) stop codons occur upstream from this ATG in all reading frames in our dCREB2 cDNAs (sequences not shown) ii) this ATG was selected by computer (65) as the best ribosome binding site in the DNA sequence that contains the ORF; and iii) use of the next ATG in the open reading frame 480 nucleotides downstream would not produce an inferred product that is a PKA-dependent activator (see below). This information does not exclude the possibility that internal translation initiation sites may be used in this transcript, as happens in the CREM gene's S-CREM isoform (15).

The dCREB2-a open reading frame predicts a protein of 361 amino acids with a carboxyl-terminal bZIP domain (SEQ ID NO.: 3) highly homologous to those of mammalian CREB (SEQ ID NO.: 4) and CREM (SEQ ID NO.: 5) (see FIG. 1B). The inferred dCREB2-a product has a small region of amino acids containing consensus phosphorylation sites (59) for PKA, calcium/calmodulin-dependent kinase II (CaM kinase II) and protein kinase C (PKC) at a position similar to that of the P-box in CREB, CREM and ATF-1. The amino-terminal third of the predicted dCREB2-a is rich in glutamines (including runs of four and five residues). Glutamine-rich activation domains occur in CREB, CREM, and other eukaryotic transcription factors, including some from Drosophila (11,54).

A computerized amino acid sequence homology search (71) with the predicted dCREB2-a protein sequence (SEQ ID NO.: 2) identifies CREB, CREM and ATF-1 gene products as the closest matches to dCREB2-a. The homology is particularly striking in the carboxyl-terminal bZIP domain where 49 of 54 amino acids are identical with their counterparts in mammalian CREB (FIG. 1B). The homology is less striking, albeit substantial, in the activation domain. Lower conservation in this domain is also characteristic of the mammalian CREB and CREM genes (48).

FIG. 2 shows the exon organization of all of the dCREB2 alternative splice forms that we have detected, both as cDNAs and by RT-PCR. Splice products of dCREB2 fall into two broad categories. One class of transcripts (dCREB2-a, -b, -c, -d) employs alternative splicing of exons 2, 4 and 6 to produce isoforms whose protein products all have the bZIP domains attached to different versions of the activation domain. The second class of transcripts (dCREB2-q, -r, -s) all have splice sites which result in in-frame stop codons at various positions upstream of the bZIP domain. These all predict truncated activation domains without dimeriation or DNA binding activity.

Two different dCREB2 isoforms, dCREB2-a and dCREB2-b, have opposite roles in PKA-responsive transcription. The capacity of isoforms of the dCREB2 gene to mediate PKA-responsive transcription was tested in F9 cells. These cells have been used extensively to study CREB-dependent activation because their endogenous cAMP-responsive transcription system is inactive (28, 49, 50). Candidate cAMP-responsive transcription factors, synthesized from expression vectors, were transiently transfected with and without a construct expressing the PKA catalytic subunit. CREB-dependent changes in gene expression were measured using a cotransfected construct that has a CRE-containing promoter fused to a reporter gene.

Figure 4:
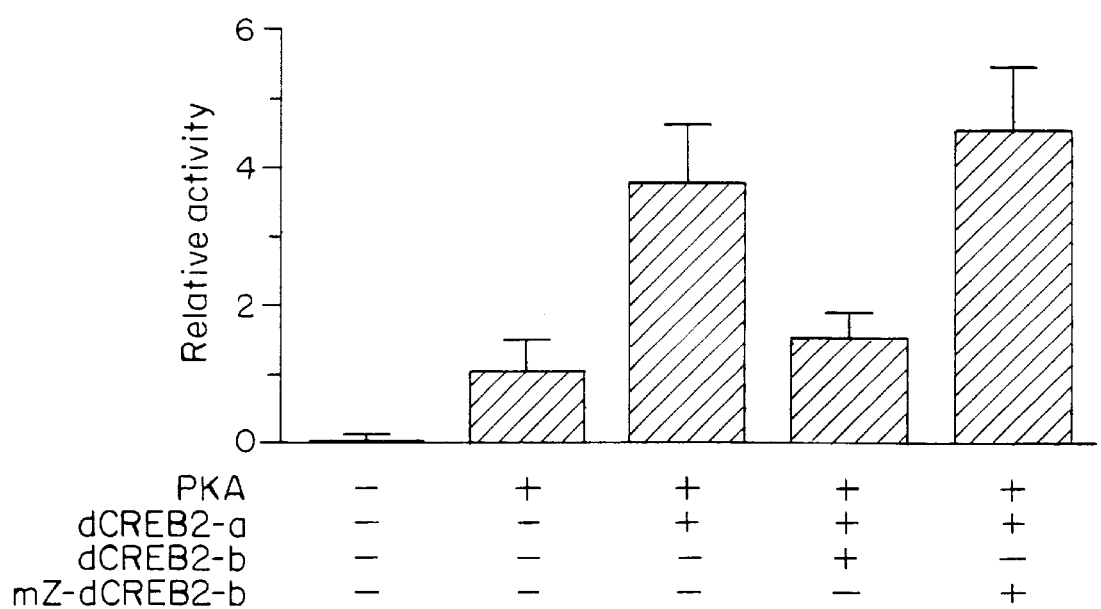
FIG. 4 is a bar graph representation of results showing the transcriptional effect of dCREB2-b and a mutant variant on pKA-responsive activation by dCREB2-a.

The product of the dCREB2-a isoform is a PKA-dependent activator of transcription (FIG. 3). Transfection of PKA or dCREB2-a alone gave only modest activation above baseline values. Cotransfection of dCREB2-a and PKA together, however, gave levels of activation 5.4-fold greater than the activation seen with PKA alone.

dCREB2-b did not act as a PKA-dependent transactivator. When transfected together with the reporter and PKA, it failed to stimulate reporter activity. Instead, it functioned as a direct antagonist of PKA-dependent activation by dCREB2-a (FIG. 4). Cotranfection of equimolar amounts of the dCREB2-a and dCREB2-b expression constructs, along with PKA and the reporter, resulted in a nearly complete block of PKA-dependent activation from the CRE-containing reporter.

The strong homology between the leucine zippers of dCREB2 (SEQ ID NO.: 3), CREB (SEQ ID NO.: 4) and CREM (SEQ ID NO.: 5) (see FIG. 1B) suggested that mutations which abolish CREB dimerization (18) should also affect dCREB2 dimerization. The mutant Drosophila molecule mLZ-dCREB2-b was made by introducing two single-base changes that convert the middle two leucines of the leucine zipper to valines. An identical mutation in CREB abolishes homodimerization in vitro (18). Cotransfected mLZ-dCREB2-b failed to block PKA-dependent activation by dCREB2-a (FIG. 4).

Example 2

Isolation and Characterization of dCREB1

A single cDNA representing the dCREB1 gene was isolated in the same screen of a Drosophila lambda gt11 expression library that yielded the dCREB2 cDNAS. The sequence of the dCREB1 cDNA contained a complete open reading frame specifying a 266 amino acid protein with a carboxyl-terminal leucine zipper four repeats long and an adjacent basic region (FIG. 5; SEQ ID NO.: 7). The amino-terminal half of the inferred protein contains an acid-rich activation domain, with glutamate, asparate and proline residues spaced throughout. dCREB1 has consensus phosphorylation sites for CaM kinase II and PKC throughout its length, but has no predicted phosphoacceptor site for PKA.

Figure 6:
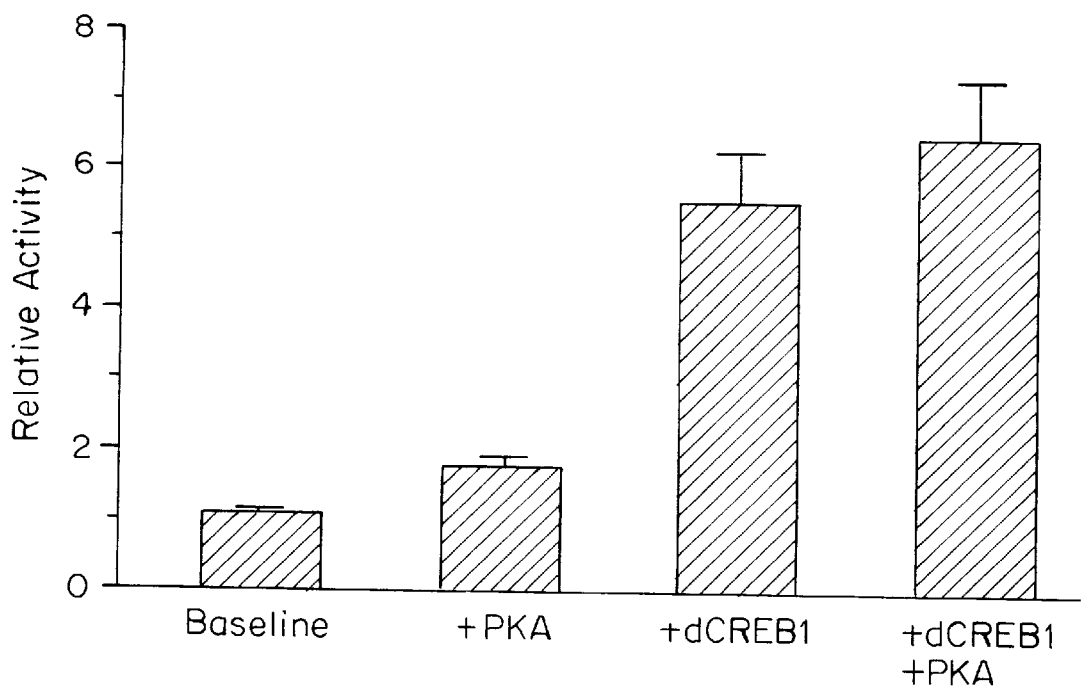
FIG. 6 is a bar graph representation of results showing transcriptional activation of a CRE reporter gene by dCREB1 in Drosophila Schneider L2 cell culture.

Gel shift analysis showed higher-affinity binding of the dCREB1 protein to 3xCRE than to 3xmCRE. Transcriptional activation by dCREB1 was assayed with transient cotransfection experiments using the Drosophila L2 and Kc167 cell culture lines. In L2 cells, dCREB1 activates transcription from CREs, but this effect is not enhanced by cotransfection of PKA (FIG. 6). In Kc167 cells, dCREB1 fails to activate reporter expression either alone or with cotransfected PKA expression constructs.

Genomic Southern blot analysis indicates that dCREB1 is a single copy gene, and chromosomal in situ hybridization shows that it is located at 54A on the right arm of chromosome 2.

These results show that dCREB1 is a non-PKA responsive CREB family member from Drosophila.

The following materials and methods were used in the work described in Examples 3 and 4.

Isolating Transgenic Flies

EcoRI restriction sites were added (using PCR) just 5' to the putative translation initiation site and just 3' to the translation termination site in the dCREB2-b cDNA. This fragment was sequenced and subcloned into CaSpeR hs43, a mini-white transformation vector which contains the hsp70 promoter, in the orientation so that the dCREB2-b open reading frame is regulated by the hsp70 promoter. Germ-line transformation was accomplished using standard techniques (Spradling and Rubin, 1982; Rubin and Spradling,1982). Two transgenic lines, 17-2 and M11-1, each with one independent P-element insertion were generated and characterized. They appeared normal in general appearance, fertility and viability. These transgenic lines were outcrossed for at least five generations to w(CS-10) (Dura et al., 1993), which itself had been outcrossed for ten generations to a wild-type (Can-S) stock. This extensive series of outcrossing is necessary to equilibrate the genetic background to that of Canton-S. Flies homozygous for the 17-2 transgene were bred and used for all experiments.

The mutant blocker has been described previously (see Example 1). The mutations were substituted into an otherwise wild-type blocker construct and germ-line transformants were made by injecting into w(isoCJ1) embryoes. Flies homozygous for the A2-2 transgene insertion were bred and used for all experiments. w(isoCJ1) is a subline of w(CS10) (see above) carrying isogenic X, $2^{nd}$ and $3^{rd}$ chromosomes and was constructed by Dr. C. Jones in our laboratory. Originally 40 such sublines were w(CS10) using standard chromosome balancer stocks. Olfactory acuity, shock reactivity, learning and three-hr memory after one-cycle training then were assayed in each isogenic subline. As expected, a range of scores among the sublines was obtained. w(isoCJ1) yielded scores that were most like those of w(CS10) on each of these assays. By injecting DNA into the relatively homogeneous genetic background of w(isoCJ1), outcrossing of the resulting germ-line transformants to equilibrate heterogeneous) genetic backgrounds was not necessary.

Cycloheximide Feeding and Heat-Shock Regimen

Flies were fed cycloheximide as reported (Tully et al., 1994) except that the feeding period was limited to 12–14 hrs prior to training, or to the 24-hr retention interval after training. Flies which were fed prior to training were transferred directly to the training apparatus after feeding, subjected to massed or spaced training, then transferred to test tubes containing filter paper strips soaked with 5% glucose during the 24-hr interval. Flies which were fed after training were trained, then transferred immediately to test tubes containing filter paper strips soaked with 5% glucose solution which was laced with 35 mM CXM. Flies remained in the test tubes for the duration of the 24-hr retention interval.

For heat-shock induction, flies were collected within two days of eclosion, placed in glass bottles in groups of about 600, and incubated overnight at 25° C. and 70% relative humidity. The next day, three hours before training, groups of approximately 100 flies were transferred to foam-stoppered glass shell vials containing a strip of filter paper to absorb excess moisture. The vials then were submerged in a 37° C. water bath until the bottom of the foam stopper (inside the vial) was below the surface of the water, thereby insuring that the flies could not escape heat-shock. The vial remained submerged for 30 min, after which the flies were transferred to a standard food vial for a 3-hr recovery period at 25° C. and 70% relative humidity. Training began immediately after the recovery period.

Pavlovian Learning and Memory and Testing

Flies were trained with an automated version of the learning procedure of Tully and Quinn (1985; Tully et al., 1994). Groups of about 100 flies were exposed sequentially to two odors [either octanol (OCT) or methylcyclohexanol (MCH)] for 60 seconds with 45 seconds rest intervals after each odor presenation. During exposure to the first odor, flies also were subjected to twelve 1.5-second pulses of 60 V DC with a 5-second interpulse interval. After training, flies were transferred to food vials for a particular retention interval. Conditioned odor-avoidance responses then were tested by transferring flies to the choice point of a T-maze, where they were exposed simultaneously to OCT and MCH carried in the distal ends of the T-maze arms and out the choice point on converging currents of air. Flies were allowed to distribute themselves in the T-maze arms for two minutes, after which they were trapped in their respective arms, anesthetized and counted. The "percent correct" then was calculated as the number of flies avoiding the shock-paired odor (they were in the opposite T-maze arm) divided by the total number of flies in both arms. (The number of flies left at the choice point, which usually was less than 5%, were not included in this calculation). Finally, a performance index (PI) was calculated by averaging the percent corrects of two reciprocal groups of flies—one where OCT and shock were paired, the other where MCH and shock were paired—and then by normalizing the average so that a PI=0 represented a 50:50 distribution in the T-maze and a PI=100 represented 100% avoidance of the shock-paired odor. For these studies, three different training protocols were used: 1. One-cycle training consisted of the training session just described. 2. Massed training consisted of 10 of these training cycles delivered one right after the other. 3. Spaced training consisted of 10 training cycles with a 15-min rest interval between each. One-cycle training was used to assay learning, while massed and spaced was used to assay consolidated memories (Tully et al., 1994).

Olfactory Acuity and Shock Reactivity

Odor avoidance responses to OCT or to MCH at two different concentrations—one ($10^0$) usually used in conditioning experiments and a 100-fold ($10^{-2}$) dilution thereof—were quantified in various groups of flies in the absence of heat shock and 3 hr or 24 hr after heat shock with the method of Boynton and Tully (1992). Briefly, flies are placed in a T-maze and given a choice between an odor and air. The odors are naturally aversive, and flies ususally choose air and avoid the T-maze arm containing the odor. For shock reactivity, flies are given a choice between an electrified grid in one T-maze arm, and an unconnected grid in the other. After the flies have distributed themselves, they are anesthetized, counted and a PI is calculated.

Statistical Analyses of Behavioral Data

Since each PI is an average of two percentages, the Central Limit Theorem predicts that they should be distributed normally (see Sokal and Rohlf, 1981). This expectation was shown to be true by an empirical determination with data from Tully and Quinn (1985) and Tully and Gold (1993). Thus, untransformed (raw) data were analyzed parametrically with JMP2.1 statistical software (SAS Institute Inc., Cary N.C.). Since preliminary experiments preceded all of the experiments summarized herein, all pairwise comparisons were planned. To maintain an experimentwise error rate of alpha=0.05, the critical P values for these individual comparisons were adjusted accordingly (Sokal and Rohlf, 1981) and are listed below for each experiment.

All experiments were designed in a balanced fashion with N=2 PIs per group collected per day; then replicated days were added to generate final Ns. In each experiment, the experimenter (M.D.) was blind to genotype.

A. One-day memory in wild-type flies fed CXM before or immediately after massed or spaced training (FIG. 8): PIs from these four drug treatments (−CXM before, −CXM after, +CXM before and +CXM after) and two training procedures (massed and spaced) were subjected to a TWO-WAY ANOVA with DRUG ($F_{(3,56)}=8.93$; P<0.001) and TRAINing ($F_{(1,56)}=18.10$, P<0.001) as main effects and DRUG×TRAIN ($F_{(3,56)}=4.68$, P=0.006) as the interaction term. P values from subsequent planned comparisons are summarized in FIG. 8. The six planned comparisons were judged significant if P≤0.01.

B. One-day memory after massed or spaced training in dCREB2-b transgenic flies (FIGS. 9A and 9B): In experiments with the 17-2 transgenic line, PIs from two strains (Can-S and 17-2) and four training-regimens (spaced−hs, spaced+hs, massed−hs and massed+hs) were subjected to a TWO-WAY ANOVA with STRAIN ($F_{(1,40)}=1.57$; P=0.22) and TRAINing-regimen ($F_{(3,40)}=25.81$, P<0.001) as main effects and STRAIN×TRAIN ($F_{(3,40)}=6.62$, P=0.001) as the interaction term. A similar analysis was done with data from the M11-1 transgenic line, yielding STRAIN ($F_{(1,40)}=2.81$; P=0.10), TRAINing-regimen ($F_{(3,40)}=11.97$, P<0.001) and STRAIN×TRAIN ($F_{(3,40)}=3.37$, P=0.03) effects. P values from subsequent planned comparisons are summarized in FIGS. 9A and 9B. In each experiment, the seven planned comparisons were judged significant if P≤5 0.01.

C. Learning after one-cycle training in 17-2 transgenic flies (FIG. 9C): PIs from two strains (Can-S and 17-2) and three heat-shock regimens [−hs, +hs (3 hr) and+hs (24 hr)] were subjected to a TWO-WAY ANOVA with STRAIN ($F_{(1,30)}=0.69$; P=0.41) and HEAT-shock regimen ($F_{(2,30)}=10.29$, P<0.001) as main effects and STRAIN×HEAT ($F_{(2,30)}=0.71$, P=0.50) as the interaction term. P values from subsequent planned comparisons are summarized in FIG. 9C. The three planned comparisons were judged significant if P≤0.02.

D. One-day memory after spaced training in A2-2 transgenic flies (FIG. 10): PIs from these three strains [w(isoCJ1), 17-2 and A2-2] and two heat-shock regimens [−hs and +hs (3 hr)] were subjected to a TWO-WAY ANOVA with STRAIN ($F_{(2,30)}=9.43$, P<0.001) and HEAT-shock regimen ($F_{(1,30)}=9.84$, P=0.004) as main effects and STRAIN×HEAT ($F_{(2,30)}=5.71$, P=0.008) as the interaction term. P values from subsequent planned comparisons are summarized in FIG. 10. The six planned comparisons were judged significant if P≤0.01.

E. Olfactory acuity in 17-2 flies (Table): PIs from these two strains (Can-S and 17-2), four different odor-levels (OCT- $10^0$, OCT- $10^{-2}$, MCH-$10^0$ and MCH-$10^{-2}$) and three heat-shock regimens [−hs. +hs (3 hr) and +hs (24 hr)] were subjected to a THREE-WAY ANOVA with STRAIN ($F_{(1,184)}=0.12$, P=0.73), ODOR-level ($F_{(3,184)}=126.77$, P<0.001) and HEAT-shock regimen ($F_{(2,184)}=3.55$, P=0.03) as main effects, STRAIN×ODOR ($F_{(3,184)}=1.23$, P=1.23, P=0.30), STRAIN×HEAT ($F_{(2,184)}=0.33$, P=0.72) and ODOR×HEAT ($F_{(6,184)}=3.14$, P=0.006) as two-way interaction terms and STRAIN×ODOR×HEAT ($F_{(6,184)}=0.48$, P=0.83) as the three-way interaction term. P values from subsequent planned comparisons are summarized in the Table. The twelve planned comparisons were significant if P≤0.005.

F. Shock reactivity in 17-2 flies (Table): PIs from these two strains (Can-S and 17-2), two shock groups (60 V and 20 V) and three heat-shock regimens [−hs, +hs (3 hr) and +hs (24 hr)] were subjected to a THREE-WAY ANOVA with STRAIN ($F_{(1,84)}=0.50$, P=0.48), SHOCK ($F_{(1,84)}=97.78$, P<0.001) and HEAT-shock regimen ($F_{(2,84)}=3.36$, P=0.04) as main effects, STRAIN×SHOCK ($F_{(1,84)}=1.12$, p=0.29), STRAIN×HEAT ($F_{(2,84)}=1.06$, P=0.35) and SHOCK×HEAT ($F_{(2,84)}=6.66$, P=0.002) as two-way interaction terms and STRAIN×SHOCK×HEAT ($F_{(2,84)}=1.75$, P=0.18) as the three-way interaction term. P values from subsequent planned comparisons are summarized in the Table. The six planned comparisons were judged significant if $P \leq -0.01$.

G. Seven-day memory after spaced training in 17-2 flies (FIG. 11): PIs from two strains (Can-S and 17-2) and two heat-shock regimens [−hs and +hs(3 hr)] were subjected to a TWO-WAY ANOVA with STRAIN ($F_{(1,20)}=6.09$; $P=0.02$) and HEAT-shock regimen ($F_{(1,20)}=16.30$, $P=0.001$) as main effects and STRAIN×TRAIN ($F_{(1,20)}=7.73$, $P=0.01$) as the interaction term. P values from subsequent planned comparisons are summarized in FIG. 11. The three planned comparisons were judged significant if $P \leq 0.02$.

H. One-day memory after spaced training in rsh;17-2 double mutants (FIG. 12): PIs from three strains (17-2, rsh and rsh;17-2) and two heat-shock regimens [−hs and +hs (3 hr)] were subjected to a TWO WAY ANOVA with STRAIN ($F_{(2,30)}=32.05$; $P<0.001$) and HEAT-shock regimen ($F_{(1,30)}=59.68$, $P<0.001$) as main effects and STRAIN×TRAIN ($F_{(2,30)}=11.59$, $P<0.001$) as the interaction term. P values from subsequent planned comparisons are summarized in FIG. 12. The five planned comparisons were judged significant if $P \leq 0.01$.

I. Learning after one-cycle training in rsh;17-2 mutants (see text): PIs from these two strains (Can-S and rsh;17-2) and two heat-shock regimens [−hs and +hs (3 hr)] were subjected to a TWO-WAY ANOVA with STRAIN ($F_{(1,20)}=86.85$, $P<0.001$) and HEAT-shock regimen ($F_{(1,20)}=0.02$, $P<0.89$) as main effects and STRAIN×HEAT ($F_{(1,20)}=0.86$, $P=0.37$) as the interaction term. P values from subsequent planned comparisons are summarized in the Table. The two planned comparisons were significant if $P \leq 0.03$.

J. Olfactory acuity in rsh;17-2 flies (Table): PIs from these two strains (Can-S and rsh;17-2), four different odor-levels (OCT-$10^0$, OCT-$10^{-2}$, MCH-$10^0$ and MCH-$10^{-2}$) and two heat-shock regimens [−hs, and +hs (3 hr)] were subjected to a THREE-WAY ANOVA with STRAIN ($F_{(1,112)}=0.02$, $P=0.88$), ODOR-level ($F_{(3,112)}=50.03$, $P<0.001$) and HEAT-shock regimen ($F_{(1,112)}=29.86$, $P<0.001$) as main effects, STRAIN×ODOR ($F_{3,112)}=2.15$, $P=0.10$), STRAIN×HEAT ($F_{(1,112)}=0.34$, $P=0.56$) and ODOR×HEAT ($F_{(3,112)}=6.41$, $P=0.001$) as two-way interaction terms and STRAIN× ODOR×HEAT ($F_{(3,112)}=1.12$, $P=0.35$) as the three-way interaction term. P values from subsequent planned comparisons are summarized in the Table. The eight planned comparisons were judged significant if $P \leq 0.01$.

K. Shock reactivity in rsh;17-2 flies (Table): PIs from these two strains (Can-S and rsh;17-2), two shock groups (60 V and 20 V) and two heat-shock regimens [−hs and +hs (3 hr)] were subjected to THREE-WAY ANOVA with STRAIN ($F_{(1,56)}=0.51$, $P=0.48$), SHOCK ($F_{(1,56)}=88.14$, $P<0.001$) and HEAT-shock regimen ($F_{(1,56)}=0.08$, $P=0.77$) as main effects, STRAIN×SHOCK ($F_{1,56)}=0.12$, $P=0.73$), STRAIN×HEAT ($F_{(1,56)}=0.03$, $P=0.86$) and SHOCK×HEAT ($F_{(1,56)}=0.39$, $P=0.53$) as two-way interaction terms and STRAIN×SHOCK×HEAT ($F_{(1,84)}=1.58$, $P=0.21$) as the three-way interaction term. P values from subsequent planned comparisons are summarized in the Table. The four planned comparisons were judged significant if $P \leq 0.01$.

Northern Analysis

For RNA collection, the heat-shock regimen was the same as for behavioral experiments. For any indicated time interval between heat-shock and collection, flies rested in food-containing vials at 25° C. Flies were collected and quickly frozen in liquid nitrogen. All Northern analyses used head RNA. The tube of frozen flies was repeatedly rapped sharply on a hard surface, causing the heads to fall off. The detached frozen heads were recovered by sieving on dry ice. Approximately 1000 heads were pooled for RNA preparation. Wild-type and transgenic flies for each individual time point always were processed in parallel. Flies that were not induced were handled in a similar manner to induced flies, except that the vials were not placed at 37° C. Total head RNA was isolated from each group of flies, and poly A+ RNA was isolated using oligo dT columns according to the instructions of the manufacturer (5'→3' Inc.). The concentration of poly A+ mRNA was measured spectrophotometrically, and 0.5 mg of mRNA per lane was loaded and run on 1.2% formaldehyde-agarose gels. Northern blots were prepared, probed and washed (0.1×SSC at 65° C.) as described (Ausubel et al., 1994). For detection of the transgene, an 843 bp dCREB2-b cDNA fragment was subcloned into pKS+ and used to generate a uniformly-labeled antisense riboprobe. This fragment codes for the carboxyl-terminal 86 amino acids of the dCREB2-b protein plus 3' untranslated mRNA.

Western Blot Analysis and Antiserum

Western blot analysis was performed using a rabbit antiserum raised against a peptide corresponding to 16 amino acids in the basic region of the dCREB2-b cDNA with an additional COOH terminal Cys. The sequence of the peptide was: (SEQ ID NO.: 24) NH2-RKREIRLQKNREAAREC-COOH. The peptide was synthesized and coupled to Sulfo-SMCC (Pierce) activated keyhole lympet hemocyanin. The antigen was injected into rabbits (100 ug) and boosted at two week intervals. Sera was bled and tested for immune reactivity towards bacterially-expressed dCREB2-b protein. The antiserum was passed through a CM Affi-gel Blue column (Biorad), and the flow-through was concentrated by ammonium sulfate precipitation, resuspended and dialyzed against PBS (0.14 M NaCl, 2.7 mM KCl, 4.3 mM $Na_2HPO_4 7H_2O$, 1.4 mM $KH_2PO_4$, pH 7.3). The dialyzed serum was affinity-purified using a peptide column made using an Ag/Ab Immobilization kit (Immunopure from Pierce). After the antiserum was eluted using a 4M $MgCl_2$, 0.1 M HEPES pH 6.0 buffer, it was dialyzed into PBS and frozen.

Each data point represents approximately 5 fly heads. Groups of about 25–50 flies were collected and quickly frozen on liquid nitrogen until all of the time points had been collected. Heads were isolated resuspended in approximately 200 ul of 1× Laemmli sample buffer, allowed to thaw and homogenized with a Dounce type B pestle. Samples were boiled for 5 minutes, and centrifuged for 10 minutes at room temperature in an Eppendoff microcentrifuge. The supernatants were collected and boiled again just prior to loading onto protein gels. Standard procedures were used to separate equal amounts of proteins from each sample on 12% polyacrylamide-SDS gels and to transfer them to PVDF membranes by electroblotting (Ausubel et al., 1994).

The membranes were blocked for 60 minutes with a 5% BSA solution made up in TBST (10 mM Tris 50 mM NaCl, 0.05% Tween 20). The primary antibody was diluted 1:1000 in TBST and incubated with the filter for 30 minutes. The membranes were washed three times with TBST for 5 minutes each time and then incubated for 30 minutes with an alkaline phosphatase-conjugated anti-rabbit IgG second antibody (Promega) diluted 1:7500 in TBST. The membranes were washed three more times as before and developed using a chromogenic alkaline phosphatase reaction according to manufacturers suggestions (Promega).

Example 3

Transgene Expression Increased After Heat-Shock Induction

In order to interpret the effects of transgene induction on behavior, dCREB2-b expression in transgenic flies (17-2)

after heat-shock induction was measured. Northern blot analysis revealed elevated levels of hs-dCREB2-b message in the 17-2 flies immediately and three hours after heat-shock (FIG. 7A). This induction was also detectable in brain cells using in situ hybridization. Western blot showed increased dCREB2-b protein immediately after induction (FIG. 7B). Elevated levels of the dCREB2-b protein were seen nine hours later and were still detectable twenty four hours after induction. These data indicate that increased amounts of dCREB2-b existed in brain cells throughout spaced training, which ended about six hours after heat induction.

The behavioral experiments also used transgenic flies (A2-2) which expressed a mutated dCREB2-b protein (dCREB2-mLZ). These mutations changed the two internal leucine residues of the leucine zipper to valine residues, and these changes have been shown to result in a protein which is unable to form dimers (Dwarki et al., 1990). In transient co-transfection assays, the mutant protein was unable to block PKA-dependent transcription mediated by dCREB2-a, while the wild-type protein had blocking function. Western blot analysis showed that the wild-type and mutant blocker are expressed at similar levels beginning immediately after heat-shock induction and lasting for at least 6 hours (FIG. 7C). Therefore, it is unlikely that these two proteins have large differences in expression levels or stability in the transgenic flies.

Northern blot analysis of two different housekeeping genes, myosin light chain (Parker et al., 1985) and elongation factor a (Hovemann et al., 1988), showed that steady-state levels of their RNAs were unaffected after transgene induction for at least 3 hours. Gel shift analysis using two different consensus DNA binding sites showed that there was no large effect on the gel shift species which formed after transgene induction for at least 9 hours. Cotransfection of the blocker did not interfere with the activity of a transcription factor from a different family in cell culture. Considered together, hs-dCREB2-b probably had fairly specific molecular modes of action after induction.

Example 4

Assessment of the Role of CREBs in Long-Term Memory Formation

Figure 8:
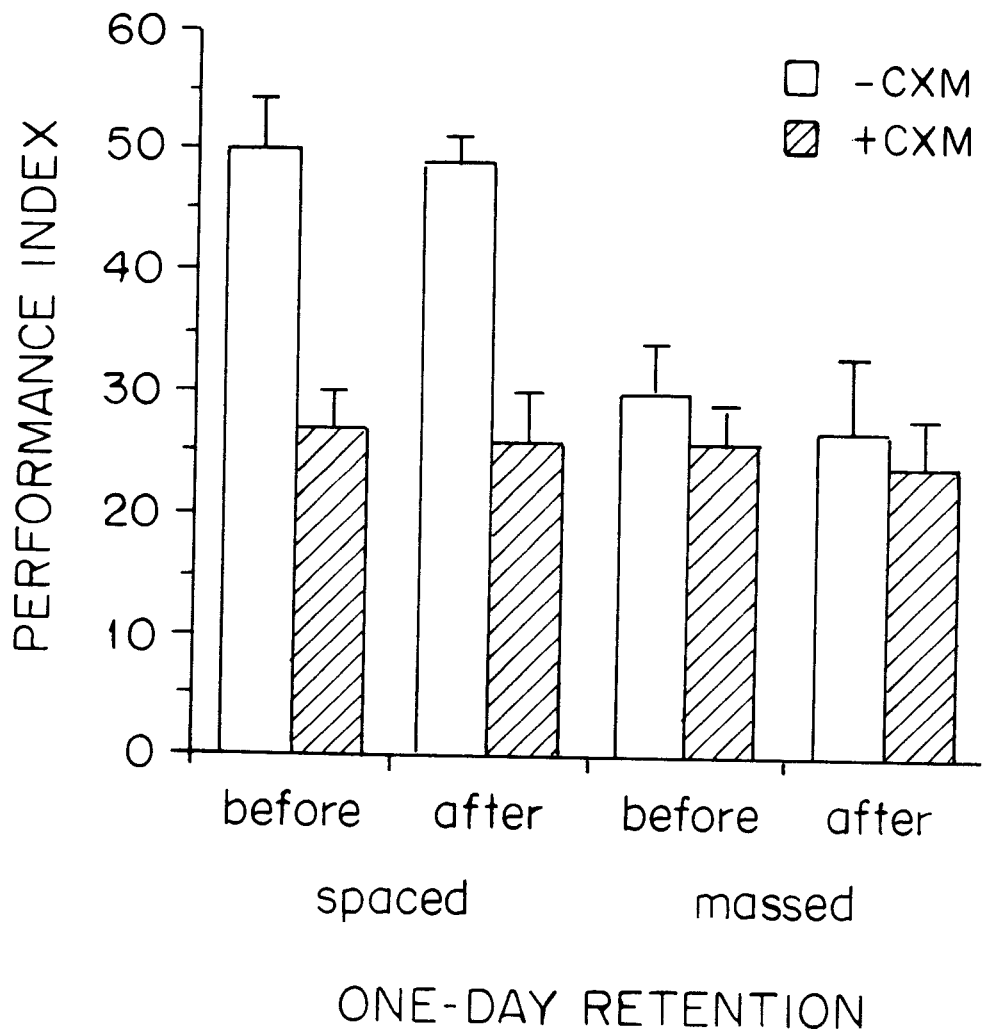
FIG. 8 is a bar graph representation of results showing the effect of cycloheximide (CXM) feeding, before or after spaced or massed training, on one-day memory retention: striped bars=+CXM; white bars=−CXM.

To confirm and extend the results of Tully et al. (1994), flies were fed 35 mM cycloheximide (CXM) for 12–14 hours before, or for the 24-hr retention interval immediately after, massed or spaced training (FIG. 8). Each of these CXM feeding regimens significantly reduced one-day memory after spaced training but had no effect on one-day memory after massed training (FIG. 8). Thus, cyclohexmide feeding immediately before or after spaced training disrupts one-day memory. These results suggest that protein synthesis is required soon after training for the formation of long-lasting memory.

The results in FIG. 8 show that cycloheximide feeding affects one-day retention after spaced training but not massed training. Different groups of wild-type (Can-S) flies were fed 5% glucose solution alone (hatched bars) or laced with 35 mM CXM (striped bars) either for 12–14 hr overnight before massed or spaced training or for the 24-hr retention interval immediately after training. One-day memory retention was significantly lower than normal in flies fed CXM before (P<0.001) or after (P<0.001) spaced training. In both cases, one-day retention in CXM-fed flies was reduced to a level similar to one-day memory after massed training in glucose-fed flies (P=0.88 for CXM before training and P=0.71 for CXM after training). In contrast, no difference was detected between CXM-fed and control flies for one-day memory after massed training (P=0.49 and P=0.46, respectively).

Figure 9A:
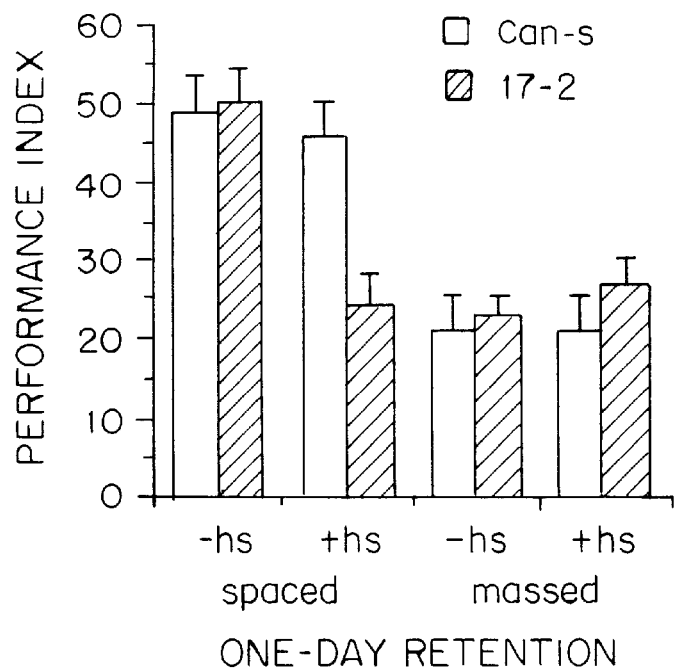
FIG. 9A is a bar graph representation of results showing the effect of heat shock induction on one-day memory retention in wildtype (Can-S) flies and hs-dCREB2-b transgenic (17-2) flies given spaced or massed training: white bars=wildtype (Can-S) flies; striped bars: hs-dCREB2-b transgenic (17-2) flies; hs=heat shock.

One day retention after spaced training was unaffected in uninduced (−hs) transgenic flies (17-2) but was significantly reduced in induced (+hs) transgenic flies (FIG. 9A). In contrast, one-day retention after massed training was normal in both uninduced and induced transgenic flies (FIG. 9A). Comparisons of one-day retention after spaced or massed training between wild-type flies with (+hs) or without (−hs) heat-shock indicated that the heat-shock regimen itself did not have a non-specific effect on memory after either training protocol. Thus induction of the dCREB2-b transgene only affected (i.e., disrupted) one-day memory after spaced training.

Figure 9B:
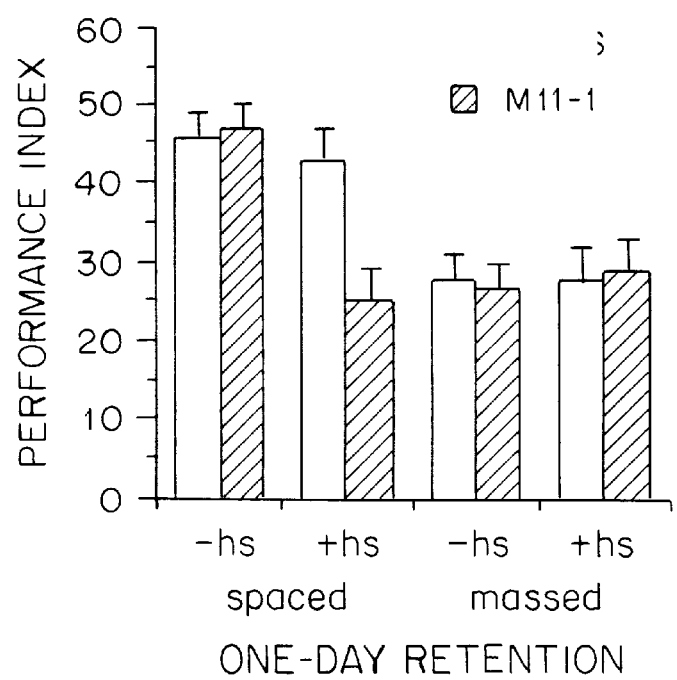
FIG. 9B is a bar graph representation of results showing the effect of heat shock induction on one-day memory retention in wildtype (Can-S) flies or hs-dCREB2-b transgenic (M11-1) flies given spaced or massed training: white bars=wildtype (Can-S) flies; striped bars: hs-dCREB2-b transgenic (M11-1) flies; hs=heat shock.

One day retention after spaced or massed training in M11-1, a second line carrying an independent hs-dCREB2-b insertion, also was tested. Results with M11-1 were similar to those obtained with 17-2 (FIG. 9B). These results show that the effect of induced hs-dCREB2-b does not depend on any particular insertion site of the transgene.

Figure 9C:
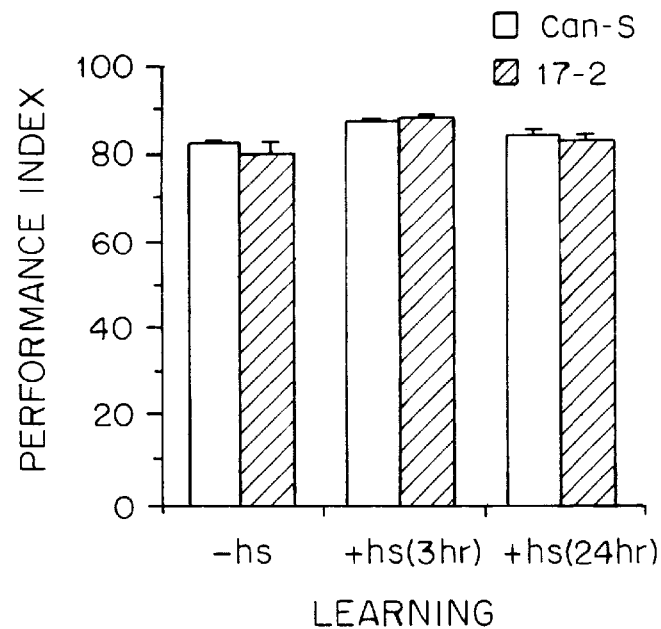
FIG. 9C is a bar graph representation of results showing the effect of heat shock induction on learning in wildtype (Can-S) flies and hs-dCREB2-b transgenic (17-2) flies given spaced or massed training: white bars=wildtype (Can-S) flies; striped bars: hs-dCREB2-b transgenic (17-2) flies; hs=heat shock.

The results in FIGS. 9A–9C show that induction of the dCREB2-b transgene disrupts one-day memory after spaced training, while one-day memory after massed training and learning are normal.

In FIG. 9A, different groups of wild-type (Can-S) flies (hatched bars) or hs-dCREB2-b transgenic (17-2) flies (striped bars) were given spaced training or massed training in the absence of heat shock (−hs) or three hours after heat shock (+hs). After training, flies were transferred to standard food vials and stored at 18° C. until one-day memory was assayed. No differences in one-day memory after spaced or massed training were detected between Can-S vs. 17-2 flies in the absence of heat shock (−hs; P=0.83 and 0.63, respectively). When flies were trained three hours after heat shock (+hs), however, one-day memory was significantly different between Can-S v. 17-2 flies after spaced training (P<0.001) but not after massed training (P=0.23). In fact, the one-day memory after spaced training was no different than that after massed training in induced 17-2 flies (P=0.59). In addition, the heat-shock regimen did not produce a non-specific effect on one-day retention after spaced (P=0.59) or massed (P=1.00) training in Can-S flies. N=6 performance indices (PIs) per group.

The experiment described in FIG. 9A was repeated in FIG. 9B with a second, independently derived dCREB2-b transgenic line, M11-1 (striped bars). Here again, a) no differences in one-day memory after spaced or massed training were detected between Can-S vs. M11-1 flies in the absence of heat-shock (−hs; P=0.83 and 0.86, respectively), b) a significant difference between Can-S v. M11-1 for one-day memory after spaced training (P<0.001) but not after massed training (P=0.85) when trained three hours after heat-shock (+hs), c) one-day memory after spaced training was no different than that after massed training in induced M11-1 flies (P=0.43) and d) the heat-shock regimen did not produce a non-specific effect on one-day retention after spaced (P=0.59) or massed (P=0.94) training in Can-S flies. N=6 PIs per group.

If induction of the transgene specifically affected LTM via disruption of gene expression, then learning should not be affected, since it does not require new protein synthesis (see Tully et al. 1994). Different groups of flies were trained using one-cycle training either without heat-shock, or three or twenty four hours after heat-shock. These time points after induction were selected to correspond to the times when flies were trained and tested in the previous experiments (see FIGS. 9A and 9B). Induction of the transgene (d-CREB2-b) in the 17-2 line had no effect on learning in either case (FIG. 9C).

In FIG. 9C, different groups of Can-S flies (hatched bars) or 17-2 transgenic flies (striped bars) received one-cycle training in the absence of heat shock (−hs) or three (+hs 3hr) or 24 (+hs 24hr) hours after heat-shock and then were tested immediately afterwards. In each case, no differences between Can-S vs. 17-2 flies were detected (Ps=0.28, 0.64 and 0.42, respectively), indicating that learning was normal in induced or uninduced transgenic flies. N=6 PIs per group.

Figure 10:
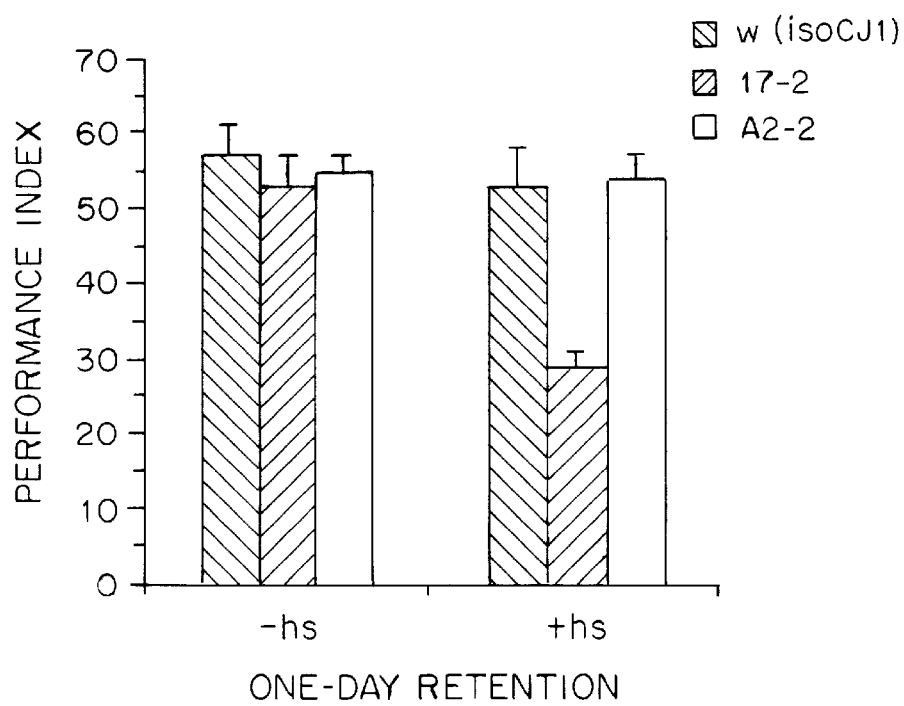
FIG. 10 is a bar graph representation of results showing the effect of heat shock induction on one-day memory retention in wildtype [w(isoCJ1)] flies, hs-dCREB2-b transgenic (17-2) flies, and mutant hs-dCREB2-mLZ transgenic (A2-2) flies given spaced training: forward striped bars=wildtype [w(isoCJ1)] flies; back striped bars=hs-dCREB2-b transgenic (17-2) flies; white bars=mutant hs-dCREB2-mLZ transgenic (A2-2) flies; hs=heat shock.

Induction of the transgene which contained the mutant blocker (A2-2) did not affect one-day retention after spaced training, while the wild-type blocker (17-2) had a dramatic effect (FIG. 10). The w(iso CJ1) flies, whose one-day retention also was unaffected by heat induction, is the isogenic control for the mutant blocker transgenic flies. Since Western blot analysis showed that wild-type and mutant blockers probably have similar expression levels, this result suggests that the blocker requires an intact leucine zipper to function effectively.

FIG. 10 shows that induction of the hs-dCREB2-mLZ mutant blocker does not affect one-day retention after spaced training. Different groups of wild-type [w (iso CJ1)], hs-dCREB2-b transgenic (17-2) or mutant hs-dCREB2-mLZ transgenic flies (A2-2) received spaced training in the absence of heat-shock (−hs) or three hours after heat-shock (+hs). The flies were then handled and tested as in FIG. 9A. No differences in one-day memory after spaced training were detected between w(isoCJ1) vs. 17-2 flies or between w(isoCJ1) vs. A2-2 flies in the absence of heat shock (−hs; P=0.38 and 0.59, respectively). When flies were trained three hours after heat shock (+hs), however, one-day memory after spaced training was significantly different between w(isoCJ1) vs. 17-2 flies (P<0.001)—as in FIG. 9A—but was not different between w(isoCJ1) vs. A2-2 flies (P=0.78). In addition, the heat-shock regimen did not produce a non-specific effect on one-day retention after spaced training in w(isoCJ1) or A2-2 flies (P=0.40 and P=0.97, respectively. N=6 performance indices (PIs) per group.

Olfactory acuity and shock reactivity are component behaviors essential for flies to properly learn odor-shock associations. The Table shows the scores for these peripheral behaviors for Can-S versus 17-2 flies. With or without heat-shock, olfactory acuity and shock reactivity were normal in 17-2 transgenic flies. Thus, hs-dCREB2-b induction does not affect olfactory acuity or shock reactivity.

Figure 11:
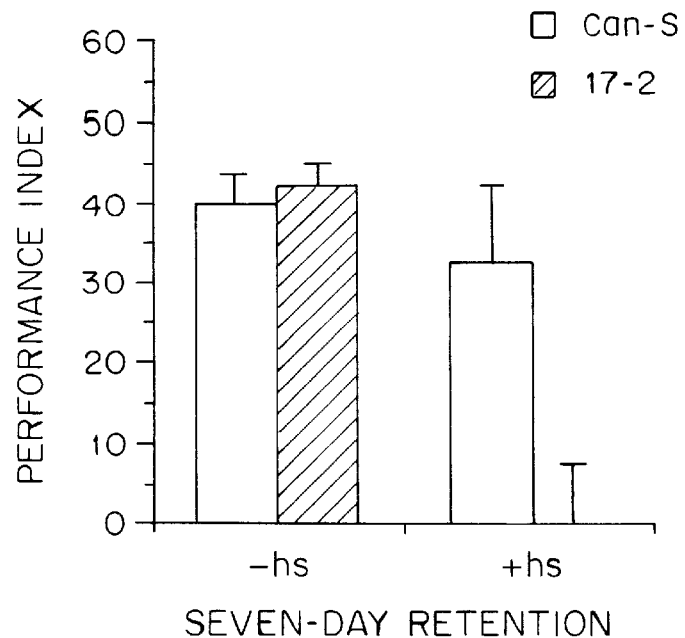
FIG. 11 is a bar graph representation of results showing the effect of heat shock induction on seven-day memory retention (long term memory) in wildtype (Can-S) flies and hs-dCREB2-b transgenic (17-2) flies given spaced training: white bars=wildtype (Can-S) flies; striped bars=hs-dCREB2-b transgenic (17-2) flies; hs=heat shock.

If induction of hs-dCREB2-b blocks long-term memory (LTM), then long-lasting memory also should be blocked. In wild-type flies, seven-day retention after spaced training consists solely of the CXM-sensitive LTM because the CXM insensitive ARM component has decayed away (Tully et al., 1994). In uninduced transgenic flies (17-2), seven-day retention after spaced training was similar to retention in uninduced wild-type flies (P=0.83; FIG. 11). Seven-day retention was severely disrupted, however, in transgenic flies which were trained three hours after heat-shock (P=0.001) and did not differ from zero (P=0.91). In contrast, the heat-shock protocol had no detectable effect on seven-day memory in wild-type flies (P=0.39). Thus, induction of hs-dCREB2-b disrupts long-term memory (LTM).

FIG. 11 shows that induction of hs-dCREB2-b completely abolishes 7-day memory retention. Previous analyses of radish mutants indicated that memory retention four or more days after spaced training reflects the sole presence of LTM. Thus, the effect of induced hs-dCREB2-b on LTM was verified by comparing 7-day retention after spaced training in Can-S (hatched bars) vs. 17-2 transgenic (striped bars) flies that were trained in the absence of heat-shock (−hs) or three hours after heat shock (+hs). Flies were stored in standard food vials at 18° C. during the retention interval. N=6 PIs per group. Seven-day retention after spaced training did not differ between Can-S and 17-2 in the absence of heat-shock (P=0.83) but was significantly lower than normal in 17-2 flies after heat-shock (P=0.002). In fact, 7-day retention after spaced training in induced 17-2 transgenic files was not different from zero (P=0.92). In addition, the heat-shock regimen did not affect 7-day retention after spaced training non-specifically in Can-S flies (P=0.39).

Figure 12:
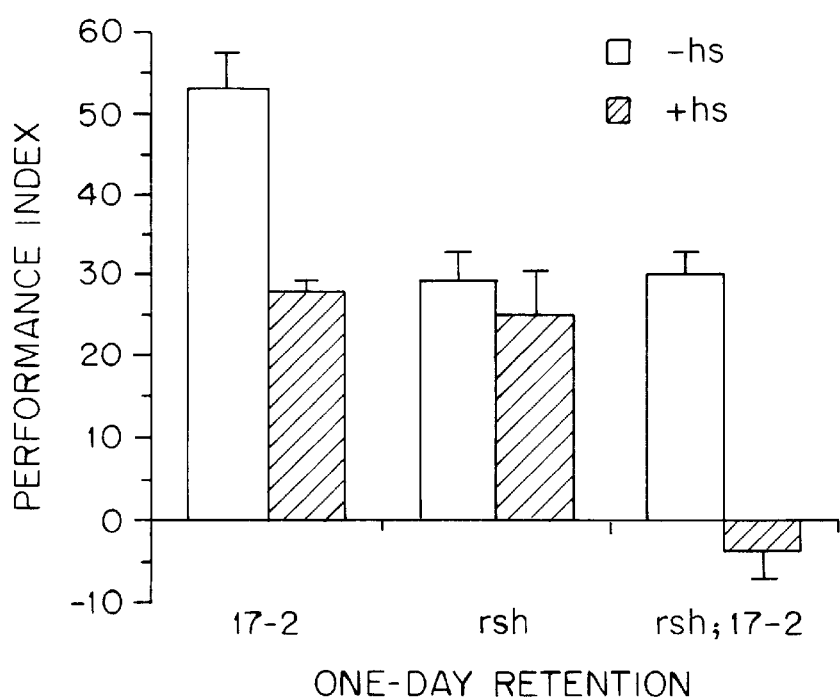
FIG. 12 is a bar graph representation of results showing the effect of heat shock induction on one-day memory retention in hs-dCREB2-b transgenic (17-2) flies, radish mutant flies, and radish hs-dCREB2-b double mutant (rsh;17-2) flies given spaced training: hs=heat shock; white bars=−hs; striped bars=+hs.

If induction of the hs-dCREB2-b transgene specifically blocks LTM, then it should only affect the CXM-sensitive component of consolidated memory after spaced training. For both transgenic lines, 17-2 and M11-1, the effect of transgene induction looked similar to the effect that CXM had on wild-type flies (compare FIG. 8 with FIGS. 9A and 9B). This similarity suggested that the induced dCREB2-b protein completely blocked CXM-sensitive memory, leaving ARM intact. The radish mutation disrupts ARM (Folkers et al., 1993), leaving only LTM one day after spaced training (Tully et al., 1994). Thus, a radish hs-dCREB2-b "double mutant" (rsh; 17-2) was constructed to allow examination of LTM in the absence of ARM. In the absence of heat-shock, rsh;17-2 double-mutants and radish single-gene mutants yielded equivalent one-day retention after spaced training (FIG. 12). In contrast, when these flies were heat-shocked three hours before spaced training, one-day retention was undetectable in rsh;17-2 flies but remained at mutant levels in radish flies. The double mutant also showed normal (radish-like) learning (P=0.59) and normal (wild-type) olfactory acuity and shock reactivity in the absence of heat-shock versus three hours after heat shock (see the Table).

TABLE 1

Olfactory acuity and shock reactivity in Can-S (wild-type), 17-2 (hs-dCREB2-b transgenic) and rsh; 17-2 (radish, hs-dCREB2-b "double mutant") flies[a].

| Heat Shock | Group | Olfactory Acuity | | | | Shock Reactivity | |
|---|---|---|---|---|---|---|---|
| | | OCT | | MCH | | | |
| | | $10^{0*}$ | $10^{-2}$ | $10^{0}$ | $10^{-2}$ | 60V | 20V |
| −hs | CAN-S | 58 ± 3 | 32 ± 3 | 80 ± 2 | 33 ± 7 | 79 ± 5 | 52 ± 5 |

TABLE 1-continued

Olfactory acuity and shock reactivity in Can-S (wild-type), 17-2 (hs-dCREB2-b transgenic) and rsh; 17-2 (radish, hs-dCREB2-b "double mutant") flies[a].

| Heat Shock | Group | Olfactory Acuity | | | | Shock Reactivity | |
|---|---|---|---|---|---|---|---|
| | | OCT | | MCH | | | |
| | | $10^{0*}$ | $10^{-2}$ | $10^{0}$ | $10^{-2}$ | 60V | 20V |
| | 17-2 | 60 ± 3 | 34 ± 8 | 77 ± 3 | 37 ± 5 | 87 ± 3 | 43 ± 2 |
| +hs (3 hrs) | CAN-S | 69 ± 4 | 41 ± 4 | 77 ± 2 | 25 ± 9 | 74 ± 5 | 58 ± 6 |
| | 17-2 | 71 ± 4 | 37 ± 3 | 76 ± 5 | 26 ± 3 | 78 ± 3 | 67 ± 5 |
| +hs (24 hr) | CAN-S | 66 ± 2 | 56 ± 8 | 79 ± 4 | 33 ± 2 | 84 ± 3 | 63 ± 3 |
| | 17-2 | 65 ± 3 | 42 ± 6 | 76 ± 3 | 41 ± 5 | 85 ± 2 | 60 ± 6 |
| −hs | CAN-S | 51 ± 4 | 39 ± 5 | 72 ± 5 | 33 ± 7 | 87 ± 3 | 52 ± 5 |
| | rsh; 17-2 | 57 ± 3 | 39 ± 5 | 74 ± 5 | 29 ± 4 | 82 ± 4 | 53 ± 6 |
| +hs (3 hr) | CAN-S | 72 ± 4 | 48 ± 3 | 66 ± 2 | 60 ± 3 | 80 ± 4 | 58 ± 6 |
| | rsh; 17-2 | 68 ± 4 | 46 ± 6 | 78 ± 2 | 49 ± 4 | 83 ± 1 | 50 ± 5 |

[a]Olfactory acuity and shock reactivity were assayed in untrained flies with the methods of Boynton and Tully (1992) and Dura et al. (1993), respectively (see Experimental Procedures for more details). N = 98 PIs per group. Planned comparisons between Can-S vs. mutant flies failed to detect any significant differences with any heat-shock regimen.
*$10^{0}$ is manual concentration and corresponds to $10^{-3}$ for bubbler (see Tully et al., 1994).

FIG. 12 shows that induction of hs-dCREB2-b completely abolishes one-day memory after spaced training in radish; 17-2 "double mutants." Since radish is known to disrupt ARM, a clear view of the effect of hs-dCREB2-b on LTM was obtained in radish;17-2 flies. One-day retention after spaced training was assayed in rsh;17-2 double mutants and in 17-2 and rsh single-gene mutants as controls. Flies were trained in the absence of heat-shock (hatched bars) or three hours after heat-shock (striped bars) and stored at 18° C. during the retention interval. As usual, induction of hs-dCREB2-b produced significantly lower one-day memory after spaced training in 17-2 flies (P<0.001). The heat-shock regimen, however, had no effect on such memory in radish mutants (P=0.52), which reflects only the presence of LTM (see Tully et al., 1994). In contrast, heat-shock produced significantly lower scores in rash;17-2 double mutants (P<0.001), which were not different from zero (P=0.20). N=6 PIs per group.

The following materials and methods were used in the work described in Examples 5 and 6.

Pavlovian Learning and Memory and Testing

During one training session, a group of about 100 flies was exposed sequentially to two odors [either octanol (OCT) or methylcyclohexanol (MCH)] for 60s with 45-s rest intervals after each odor presentation. During exposure to the first odor, flies received twelve 1.5-s pulses of 60 V DC with a 5-s interpulse interval.

After training, flies were transferred to food vials and stored at 18° C. for a seven-day retention interval. Conditioned odor-avoidance responses then were tested by transferring files to the choice point of a T-maze, where they were exposed simultaneously to OCT and MCH carried on converging currents of air in the distal ends of the T-maze arms and out the choice point.

Flies were allowed to distribute themselves in the T-maze arms for 120s, after which they were trapped in their respective arms, anesthetized and counted. The "percent correct" then was calculated as the number of flies avoiding the shock-paired odor (they were in the opposite T-maze arm) divided by the total number of flies in both arms. (The number of flies left at the choice point, which usually was less than 5%, were not included in this calculation.) Finally, a performance index (PI) was calculated by averaging the percent corrects of two reciprocal groups of flies—one where OCT and shock were paired, the other where MCH and shock were paired—and then by normalizing the average so that a PI=0 represented a 50:50 distribution in the T-maze and a PI=100 represented 100% avoidance of the shock-paired odor.

All behavioral experiments were designed in a balanced fashion with N=2 PIs per group collected per day; then replicated across days to generate final Ns. In all experiments, the experimenter was blind to genotype.

Statistical Analyses of Behavior Data

PIs are distributed normally (Tully and Gold 1993). Consequently, untransformed (raw) data were analyzed parametrically with JMP3.01 statistical software (SAS Institute Inc., Cary NC). Negative accelerating exponential Gompertz (growth) functions (see Lewis 1960) were fit to the data in FIGS. 13A and 13B via nonlinear least squares with iteration.

Example 5

Effect on Long Term Memory of Repeated Training Sessions

Seven-day memory retention (a measure of long term memory) in wild-type (Can-S) flies is induced incrementally by repeated training sessions. An automated version of a discriminative classical conditioning procedure was used to electroshock flies during exposure to one odor (CS+) but not to a second odor (CS−). Seven days after one or more training sessions, memory retention of conditioned odor avoidance responses was quantified in a T-maze, where flies were presented the CS+ and CS− simultaneously for 120s.

In FIG. 13A, long term memory as a function of the number of training sessions is indicated by open circles. One training session produced a mean performance index (PI±SEM; Note 1) near zero. Additional training sessions with a 15-min rest interval between each, however, yielded a steady increase in mean PIs with a maximum of 39 after ten training sessions. Ten additional training sessions produced similar performance. A nonlinear "growth" function (solid line) was fit to the individual PIs using an iterative least squares method. N=13, 6, 6, 6, 13, 7, 7, 7, 7, 6, 7 and 7 PIs for groups receiving 1–10, 15 and 20 training sessions, respectively.

Example 6

Effect on Long Term Memory of the Rest Interval Between Each Training Session Seven-day memory retention (a measure of long term memory) in wild-type (Can-S) flies is induced incrementally by the rest interval between each training session. As described in Example 5, an automated version of a discriminative classical conditioning procedure was used to electroshock flies during exposure to one odor (CS+) but not to a second odor (CS−). Seven days after one or more training sessions, memory retention of conditioned odor avoidance responses was quantified in a T-maze, where flies were presented the CS+ and CS− simultaneously for 120s.

In FIG. 13B, long term memory as a function of the rest interval is indicated by open circles. Ten training sessions with no rest interval between each (massed training) produced a mean PI near zero. Increasing the rest interval between each of ten training sessions yielded a steady increase in mean PIs with a maximum of 34 for a 10-min rest interval. Rest intervals up to ten minutes longer produced similar performance. A nonlinear growth function (solid line) was fit to the data as above. N=12, 6, 6, 6, 6, 13, 7, 7, 7, 7, 7, 7 and 7 PIs for groups receiving 0–10, 15 and 20 min of rest between each training session.

The following materials and methods were used in the work described in Examples 7–10.

Isolating Transgenic Flies

EcoRI restriction sites were added (using PCR) just 5' to the putative translation initiation site and just 3' to the translation termination site in the dCREB2-a CDNA. This fragment was sequenced and subcloned into CaSpeR hs43, a mini-white transformation vector which contains the hsp70 promoter, in the orientation so that the dCREB2-a open reading frame is regulated by the hsp70 promoter. Germ-line transformation was accomplished by injecting into isogenic w(isoCJ1) embryoes using standard techniques (Spradling and Rubin, 1982; Rubin and Spradling, 1982). By injecting DNA into the relatively homogeneous genetic background of w(isoCJ1), outcrossing of the resulting germ-line transformants to equilibrate (heterogeneous) genetic backgrounds was not necessary. Two transgenic lines, C28 and C30, each with one independent P-element insertion were generated and characterized. They appeared normal in general appearance, fertility and viability. Flies homozygous for the C28 or C30 transgene were bred and used for all experiments.

Heat Shock Regimen

For heat-shock induction, flies were collected within two days of eclosion, placed in glass bottles in groups of about 600, and incubated overnight at 25° C. and 70% relative humidity. The next day, three hours before training, groups of approximately 100 flies were transferred to foam-stoppered glass shell vials containing a strip of filter paper to absorb excess moisture. The vials then were submerged in a 37° C. water bath until the bottom of the foam stopper (inside the vial) was below the surface of the water, thereby insuring that the flies could not escape heat-shock. The vial remained submerged for 30 min, after which the flies were transferred to a standard food vial for a 3-hr recovery period at 25° C. and 70% relative humidity. Training began immediately after the recovery period.

Statistical Analyses of Behavior Data

PIs from the three strains (Can-S, C28 and C30) and six training-regiments (1×+hs, 2'massed+hs, 10×massed+hs, 1×−hs, 2×massed−hs and 10×massed−hs) were subjected to a TWO-WAY ANOVA with STRAIN ($F_{(2,102)}=48.34$; P<0.001) and TRAINing-regimen ($F_{(5,102)}=25.47$, P<0.001) as main effects and STRAIN×TRAIN ($F_{(10,102)}=5.85$, P<0.001) as the interaction term. Since preliminary experiments preceded all of the experiments summarized herein, all pairwise comparisons were planned. To maintain an experimentwise error rate of alpha=0.05, the individual comparisons summarized in FIG. 15B were judged significant if P<0.002 (Sokal and Rohlf 1981).

Example 7

A Molecular Switch for the Formation of Long Term Memory

FIG. 14 presents a conceptual method of a molecular switch for the formation of LTM, based on differential regulation of CREB isoforms with opposing functions.

Immediately after one training session, the relevant CREB activators and repressors are induced. Their combined functions (rather than molecular concentrations) are equivalent and yielded no net effect of CREB activators. Thus, repeated sessions of massed training (no rest interval) never induce LTM (see FIG. 15A). CREB repressors functionally inactivate faster than CREB activators, however, yielding an increasing net effect of CREB activators (ΔC) with time (see FIG. 13B). If ΔC is positive at the end of a particular rest interval during spaced training, then CREB activators are free to initiate downstream events involved with the formation of LTM. Usually, ΔC after one training session is not large enough to yield much LTM. Thus, repeated spaced training sessions serve to increase ΔC incrementally eventually to produce maximal LTM (see FIG. 13A).

Figure 15C:
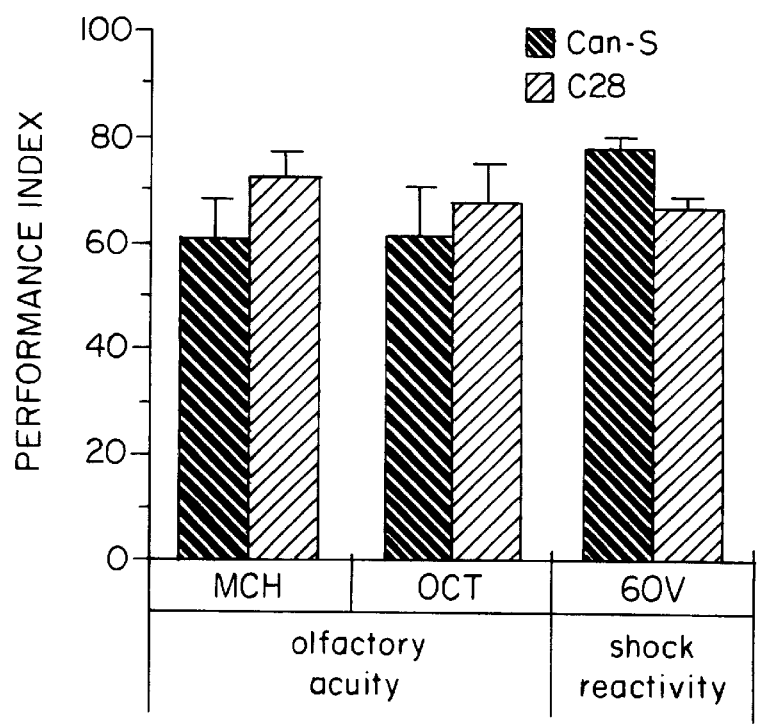
FIG. 15C is a bar graph representation of results showing responses three hours after heat shock in wildtype (Can-S) flies and hsp-dCREB2-a transgenic (C28) flies to odors, either octanol (OCT) or methylcyclohexanol (MCH), or to shock (60 V DC): forward striped bars=wildtype (Can-S) flies; back striped bars=hsp-dCREB2-a transgenic (C28) flies.

Experimental verification of two predictions from this model involving CREB as a molecular switch for long term memory formation is shown in FIGS. 15A–15C and discussed in Examples 8–10.

Example 8

Effect on Long Term Memory of Having Equal Amounts of CREB Activators and Repressors Immediately After One Training Session The model of a molecular switch for LTM predicts that the functional effects of all CREB activators and repressors are equal immediately after one training session (ΔC=0). If no rest interval occurred between additional training sessions (massed training), then functional CREB activator would not accumulate, thereby preventing the induction of downstream events required for LTM induction.

To test this notion, wild-type (Can-S) flies were subjected to 48, instead of the usual 10 (see FIG. 15B), massed training sessions (48× massed) or, as a positive control, to 10 spaced training sessions with a 15-min rest interval (10× spaced). Seven-day memory after such massed training was near zero (FIG. 15A), while that after spaced training was near its usual maximum value (see FIG. 13A). Thus, nearly five times the usual amount of massed training still did not induce LTM. N=6 PIs for each group.

PIs from two groups (10× spaced or 48× massed) of wild-type (Can-S) files were subjected to a ONE-WAY ANOVA with GROUP ($F_{[10]}=51.13$; P<0.001) as the main effect. A subsequent planned comparison revealed that the mean PI of the 48× massed group did not differ significantly from zero ($t_{[10]}=1.66$; P=0.127).

Example 9

Effect on Long Term Memory of Increasing Amounts of CREB Activator

The model of a molecular switch for LTM predicts that experimentally increasing the amount of CREB activator will eliminate the requirements for at least 10 repeated training sessions with a 10-min rest interval between each to produce maximal LTM.

To test this idea, two transgenic lines (C28 and C30) carrying an inducible hsp-dCREB2-a activator construct inserted into different cytological locations were generated. Different groups of flies from these two transgenic lines were subjected, along with wild-type (Can-S) flies, to 1 (1×) 2 (2×) or (10×) massed training sessions three hours after heat-shock induction of the transgene (induced) or in the absence of heat-shock (uninduced).

Without heat-shock, seven-day memory in all three strains did not differ from zero after one, two or ten massed training sessions (all Ps>0.002;). With heat-shock, seven-day memory in wild-type flies remained near zero in each massed training group (all Ps>0.002). In contrast, seven-day memory was significant (near the maximum of 35) after ten massed sessions in both the C28 and C30 transgenic lines (all Ps<0.0001). Moreover, seven-day memory after one training session was similar to that after ten training sessions in both C28 (P=0.89) and C30 (P=0.89) transgenic flies. Thus, maximum LTM was induced after just one training session in transgenic flies expressing abnormally high levels of CREB activator. N=10, 4 and 6 PIs for each group of Can-S, C28 and C30, respectively.

Example 10

Olfactory Acuity and Shock Reactivity

Odor avoidance responses to OCT or to MCH were quantified with the method of Boynton and Tully (1992) given a choice between an odor and air. The odors are naturally aversive, and flies usually chose air and avoided the T-maze arm containing the odor. After 120s, the flies were trapped in their respective arms of the T-maze, anesthetized and counted. A PI was calculated as a normalized percent correctly avoiding the odor (cf. Example 5). PIs from these two strains and two odor-groups (OCT and MCH) were subjected to a TWO-WAY ANOVA with STRAIN ($F_{(1,12)}$=1.57, P=0.23) and ODOR ($F_{(1,12)}$=0.07, P=0.80) as main effects and DRUG×ODOR ($F_{(1,12)}$=0.15, P=0.71) as the interaction term. The two subsequent planned comparisons were judged significant if P<0.025.

Shock reactivity was quantified with the method of Dura et al. (1993) in wild-type (Can-S) flies, or in a transgenic line (C28) carrying an inducible hsp-dCREB2-a construct, three hours after a 30-min heat shock at 37° C. Briefly, flies were placed in a T-maze and given a choice between an electrified grid (60 V DC) in one T-maze arm and an unconnected grid in the other. After 120s, the flies were trapped in their respective T-maze arms, anesthetized and counted. A PI was calculated as for olfactory acuity. PIs from these two strains were subjected to a ONE-WAY ANOVA with STRAIN ($F_{(1, 6)}$=13.03, P=0.01) as the main effect.

Naive avoidance responses to odors or to shock three hours after heat-shock did not differ between wild-type (Can-S) versus transgenic (C28) flies for the two odorants (MCH and OCT) used for conditioning experiments (P=0.27, 0.55, respectively). N=4 PIs per group. Naive shock avoidance responses three hours after training for transgenic flies were slightly lower than those for wild-flies (P=0.01). N=4 PIs per group.

Examples 11–13 pertain to the Drosophila nitric oxide synthase work.

Example 11

Low Stringency Hybridization to a Phage Library of the Drosophila Genome and Screening of Drosophila cDNA Library $6\times10^4$ plaques of a genomic Drosophila λDASH library with the 1.3 kb Bgl II fragment of rat neuronal NOS CDNA (residues 3282–4573) under low stringency conditions of 40% formamide were screened as described in W. M. McGinnis et al., Nature 308:428 (1984). Fifty positive phage were purified and grouped based on inter se hybridization. The contig containing the 2.4R fragment of dNOS was comprised of 15 phage clones. Regions of cross-hybridization to the rat probe were identified, subcloned and three of them were sequenced. The other two did not contain sequences homologous to any protein in the database. A Drosophila head cDNA library (a gift from P. Salvaterra) was screened with the 2.4R fragment isolated from phage clone λ8.11 in standard conditions. All phage purification and cloning steps were done with standard methods (J. Sambrook, E. F. Fritsch, T. Maniatis, Molecular cloning: A Laboratory Manual (Cold Spring Harbor Laboratory, Cold Spring Harbor, N.Y., 1989). cDNA fragments were subcloned into Bluescript (Stratagene) and sequenced on both strands with Sequenase 2.0 (USB).

Example 12

Activity of Drosophila Nitric Oxide Synthase (dNOS)

The expression construct for activity assays contained dNOS cDNA (with an XbaI site engineered immediately upstream of the ATG codon) cloned into the XbaI and SmaI sites of the pCGN expression vector [M. Tanaka and W. Herr, Cell, 60:375 (1990)]. 293 human kidney cells were transfected with 15 μg of the dNOS construct, or vector DNA, and precipitated with calcium phosphate as described in [M. J. Imperiale, L. T. Feldman and J. R. Nevins, Cell, 35:127 (1983)]. Cells were collected 2 days later and protein extracts were prepared as described in [J. Sambrook, E. F. Fritsch, T. Maniatis, Molecular cloning: A Laboratory Manual (Cold Spring Harbor Laboratory, Cold Spring Harbor, N.Y., 1989)].

The fusion protein for raising anti-DNOS antibodies was made by cloning a 0.29 kb Eam1105I-SacI fragment of dNOS cDNA (this fragment codes for 97 N-terminal amino acids of dNOS ORF) into EcoRI site of PGEX-KG [K. Guan and J. E. Dixon, Anal. Biochem., 192:262 (1991)]. The fusion protein was expressed in BL21 E. coli strain and purified over Glutathione-Sepharose columns (Pharmacia) as described in [G. J. Hannon, D. Demetrick, D. Beach, Genes & Dev., 7:2378 (1993)]. Immunization of rabbits, and serum preparation, was done by Hazleton Research Products, Inc. (Denver). The DNOS protein was detected on Western blots using a 1:500 dilution of rabbit serum, and cross-reacting bands were visualized with anti-rabbit alkaline phosphatase conjugate (Promega) according to the protocol provided.

The enzymatic assay was done essentially as described previously (D. Bredt and S. Snyder, Proc. Natl. Acad. Sci. USA, 87:682 (1990)]. A 100 ml reaction mixture containing 25 μl (50–100 μg) of soluble protein extract, 50 mM Hepes pH 7.4, 3 μM FAD, 3 μM FMN, 10 μM tetrahydrobiopterin (ICN), 1 mM DTT, 0.8 mM $CaCl_2$, 1 mM NADPH, 10 μg/ml calmodulin, 2μl of [$^3$H]L-arginine (35.7 Ci/mmol, NEN) and 50 mM L-valine in was incubated for 60 minutes at 37° C. The reaction was stopped with 0.5 ml 20 mM Hepes pH 5.5, 2 mM EDTA, 2 mM EGTA, loaded on 0.5 ml Dowex AG 50WX-8 ($Na^+$ form) column and eluted with 3×0.5 ml of the stop buffer. Radioactivity present in the eluent was quantified in a scintillation counter.

FIGS. 17A–17B show the expression of DNOS enzymatic activity in 293 kidney cells. FIG. 17A shows the results of a Western blot analysis of protein extracts from 293 cells transfected with vector alone (lane 293+vector) or with dNOS CDNA construct (lane 293+dNOS). 25 μg of soluble protein extracts was resolved on 7.5% polyacrylamide gel, transferred to nitrocellulose membrane and treated with anti-DNOS antibody. The arrow indicates the position of the DNOS protein. Positions of molecular weight markers (in kD) are shown on the left.

FIG. 17B shows siginificant DNOS enzyme activity measured in 293 cell extracts by conversion of $^3$H-L-arginine to $^3$H-L-citrulline. Enzymatic activity was detected only in cells transfected with dNOS cDNA construct (groups B–D) and is presented as specific activity (pmol of citrulline/mg/min.). The DNOS activity also was measured in the presence of 1 mM EGTA without exogenous $Ca^{2+}$ or calmodulin (group C), or in the presence of 100 mM L-NAME (group D). N=4 reactions per group.

Example 13

Splicing Pattern of dNOS

Heads and bodies of adult flies were separated on sieves. Total RNA was isolated by the guanidinium isothiocyanate method [P. Chomczynski and N. Sacchi, *Anal. Biochem.*, 162:156 (1987)]. Poly(A)$^+$ RNA selection, Northern blot and hybridization were done with standard methods (J. Sambrook, E. F. Fritsch, T. Maniatis, *Molecular cloning: A Laboratory Manual* (Cold Spring Harbor Laboratory, Cold Spring Harbor, N.Y., 1989)]. The blot was hybridized with random-primed dNOS cDNA ($10^6$ cpm/ml), washed in 0.1×SSC and 0.1% SDS at 65° C. and exposed to X-ray film for 72 hours. Two 25-mer primers [corresponding to residues 1374–1399 (the top primer) and 1793–1817 (the bottom primer) in the dNOS sequence] were used to amplify fragments of two dNOS splice products. Each RT-PCR reaction contained 30 ng of poly(A)$^+$ head RNA. In the first stage (RT), 90 ng of the bottom primer and 5 U of rTth polymerase (Perkin-Elmers) were added and the mixture was incubated in the MJ Research Minicycler™ in the following sequence of conditions: 95°/1 minute, 67°/45 seconds, 70°/13 minutes. The second stage (PCR) was carried out as follows: 94°/45 seconds, 63°/45 seconds, 70°/90 seconds and was repeated for 35 cycles. Products of the reaction were analyzed on a denaturing polyacrylamide (8%) gel. Bands of interest were isolated, reamplified, cloned into pCR1000 (InVitrogen) and sequenced with Sequenase kit (USB).

Northern blot analysis of dNOS expression in adult flies shows a 5.0 kb dNOS transcript present in heads (FIG. 18A). Each lane contained 10 mg of poly (A)$^+$ mRNA isolated from Drosophila heads (H) or bodies (B). The Northern blot was hybridized with the dNOS cDNA as described above (30). Positions of size markers (in kb) are shown on the left. The blot was overprobed with myosin light chain (MLC) (41) as a standard for RNA concentration.

FIG. 18B shows that the dNOS gene expresses two alternatively spliced mRNA species. RT-PCR reactions were performed on poly(A)$^+$ mRNA isolated from Drosophila heads and were resolved on 8% polyacrylamide gel. Arrows indicate the positions of DNA fragments of expected sizes: the 444 bp long-form fragment and the 129 bp short-form fragment (lane +RNA). Other bands present in this lane are artifacts from heteroduplexes that failed to denature. Poly (A)$^+$ mRNA was omitted from the control reaction (lane –RNA), which otherwise was done in identical conditions. Size markers (kb ladder) are shown in the middle lane (KB).

Equivalents

Those skilled in the art will know, or be able to ascertain, using no more than routine experimentation, many equivalents to the specific embodiments of the invention described herein. These and all other equivalents are intended to be encompassed by the following claims.

LIST 1

1. Abel, T., R. Bhatt, and T. Maniatis. 1992. A Drosophila activator binds to both fat body and liver-specific regulatory elements. Genes Dev. 6:466–488.
2. Alberini, C. M., M. Ghirardi, R. Metz, and E. R. Kandel. 1994. C/EBP is an immediate-early gene required for the consolidation of long-term facilitation in Aplysia. Cell 76:1099–114.
3. Alberts, A. S., J. Arias, M. Hagiwara, M. R. Montminy, and J. R. Feramisco. 1994. Recombinant cyclic AMP response element binding protein (CREB) phosphorylated on Ser-133 is transcriptionally active upon its introduction into fibroblast nuclei. J Biol Chem 269:7623–30.
4. Ausubel, F. 1994. Current Protocols in Molecular Biology. John Wiley and Sons, New York
5. Backsai, B. J., B. Hochner, M. Mahaut-Smith, S. R. Adams, B. K. Kaang, E. R. Kandel, and R. Y. Tsien. 1993. Spatially resolved dynamics of cAMP and protein kinase A subunits in Aplysia sensory neurons. Science 260:222–226.
6. Brindle, P., S. Linke, and M. Montminy. 1993. Protein-kinase-A-dependent activator in transcription factor CREB reveals new role for CREM repressors. Nature 364: 821–824.
7. Buchler, W., U. Walter, B. Jastorff, and S. M. Lohmann. 1988. Catalytic subunit of cAMP-dependent protein kinase is essential for cAMP-mediated mammalian gene expression. Febs Lett 228:27–32.
8. Buratowski, S., M. Sopta, J. Greenblatt, and P. A. Sharp. 1991. RNA polymerase II-associated proteins are required for a DNA conformation change in the transcription initiation complex. Proc Natl Acad Sci USA 88:7509–13.
9. Busch, S. J., and P. Sassone-Corsi. 1990. Dimers, leucine zippers and DNA-binding domains. Trends. Genet. 6:36–40.
10. Chrivia, J. C., R. P. Kwok, N. Lamb, M. Hagiwara, M. R. Montminy, and R. H. Goodman. 1993. Phosphorylated CREB binds specifically to the nuclear protein CBP. Nature 365:855–9.
11. Courey, A. J., and R. Tjian. 1992. Mechanisms of Transcriptional Control as Revealed by Studies of the Human Transcription Factor Sp1. In S. L. McKnight & K. R. Yamamoto (Ed.), Transcriptional Regulation, vol. 2. Cold Spring Harbor Press, Cold Spring Harbor
12. Darrow, A. L., R. J. Rickles, and S. Strickland. 1990. Maintenance and use of F9 teratocarcinoma cells. In (Ed.), Methods Enzymol, vol. 190.
13. Dash, P. K., B. Hochner, and E. R. Kandel. 1990. Injection of the cAMP-responsive element into the nucleus of Aplysia sensory neurons blocks long-term facilitation. Nature 345:718–21.
14. deGroot, R. P., and P. Sassone-Corsi. 1993. Hormonal control of gene expression: Multiplicity and versatility of cyclic adenosine 3',5'-monophosphate-responsive nuclear regulators. Mol. Endocrinol. 7:145–153.
15. Delmas, V., B. M. Laoide, D. Masquilier, G. R. de, N. S. Foulkes, and P. Sassone-Corsi. 1992. Alternative usage of initiation codons in MRNA encoding the cAMP-responsive-element modulator generates regulators with opposite functions. Proc Natl Acad Sci U S A 89:4226–30.

16. Deutsch, P. J., J. P. Hoeffler, J. L. Jameson, J. C. Lin, and J. F. Habener. 1988. Structural determinants for transcriptional activation by cAMP-responsive DNA elements. J Biol Chem 263:18466–72.
17. Drain, P., E. Folkers, and W. G. Quinn. 1991. cAMP-dependent protein kinase and the disruption of learning in transgenic flies. Neuron 6:71–82.
18. Dwarki, V. J., M. Montminy, and I. M. Verma. 1990. Both the basic region and the 'leucine zipper' domain of the cyclic AMP response element binding (CREB) protein are essential for transcriptional activation. Embo J 9:225–32.
19. Eberl, D. F., L. A. Perkins, M. Engelstein, A. J. Hilliker, and N. Perrimon. 1992. Genetic and developmental analysis of polytene section 17 on the X chromosome of *Drosophila melanogaster*. Genetics 130: 569–583.
20. Edlund, T., M. D. Walker, P. J. Barr, and W. J. Rutter. 1985. Cell-specific expression of the rat insulin gene: Evidence for role of two distinct 5' flanking elements. Science 230:912–916.
21. Engels, W. R., C. R. Preston, P. Thompson, and W. B. Eggleston. 1986. In situ hybridization to Drosophila salivary chromosomes with biotinytlated DNA probes and alkaline phosphatase. Focus 8:6–8.
22. Fantozzi, D. A., A. T. Harootunian, W. Wen, S. S. Taylor, J. R. Feramisco, R. Y. Tsien, and J. L. Meinkoth. 1994. Thermostable inhibitor of cAMP-dependent protein kinase enhances the rate of export of the kinase catalytic subunit from the nucleus. J. Biol. Chem. 269:2676–2686.
23. Foster, J. L., G. C. Higgins, and F. R. Jackson. 1988. Cloning, sequence, and expression of the Drosophila cAMP-dependent protein kinase catalytic subunit gene. J Biol Chem 263:1676–81.
24. Foulkes, N., and P. Sassone-Corsi. 1992. More is better: activators and repressors from the same gene. Cell 68 411–414.
25. Foulkes, N. S., E. Borrelli, and P. Sassone-Corsi. 1991. CREM gene: use of alternative DNA-binding domains generates multiple antagonists of cAMP-induced transcription. Cell 64:739–49.
26. Foulkes, N. S., B. Mellstrom, E. Benusiglio, and P. Sassone-Corsi. 1992. Developmental switch of CREM funtion during spermatogenesis: from antagonist to activator. Nature 355:80–84.
27. Gonzalez, G. A., P. Menzel, J. Leonard, W. H. Fischer, and M. R. Montminy. 1991. Characterization of motifs which are critical for activity of the cyclic AMP-responsive transcription factor CREB. Mol Cell Biol 11: 1306–12.
28. Gonzalez, G. A., K. K. Yamamoto, W. H. Fischer, D. Karr, P. Menzel, W. 3. Biggs, W. W. Vale, and M. R. Montminy. 1989. A cluster of phosphorylation sites on the cyclic AMP-regulated nuclear factor CREB predicted by its sequence. Nature 337:749–52.
29. Gorman, C. M., G. T. Merlino, M. C. Willingham, I. Pastan, and B. H. Howard. 1982. The Rous sarcoma virus long terminal repeat is a strong promoter when introduced into a variety of eukaryotic cells by DNA-mediated transfection. Proc Natl Acad Sci USA 79:6777–81.
30. Grossman, M. and H. W. Norton. 1980. Approximate intrinsic bias in estimates of heritability based on variance component analysis. J. Hered. 71:295–297.
31. Grove, J. R., D. J. Price, H. M. Goodman, and J. Avruch. 1987. Recombinant fragment of protein kinase inhibitor blocks cyclic AMP-dependent gene transcription. Science 238:530–3.
32. Habener, J. F. 1990. Cyclic AMP response element binding proteins: a cornucopia of transcription factors. Mol. Endocrinol. 4:1087–1094.
33. Hagiwara, M., P. Brindle, A. Harootunian, R. Armstrong, J. Rivier, W. Vale, R. Tsien, and M. R. Montminy. 1993. Coupling of hormonal stimulation and transcription via the cyclic AMP-responsive factor CREB is rate limited by nuclear entry of protein kinase A. Mol Cell Biol 13:4852–9.
34. Hai, T. Y., F. Liu, W. J. Coukos, and M. R. Green. 1989. Transcription factor ATF cDNA clones: An extensive family of leucine zipper proteins able to selectively form DNA binding heterodimers. Genes & Dev. 3:2083–2090.
35. Han, K., M. S. Levine, and J. L. Manley. 1989. Synergistic activation and repression of transcription by Drosophila homeobox proteins. Cell 56:573–83.
36. Hartoonian, A. T., S. R. Adams, W. Wen, J. L. Meinkoth, S. S. Taylor, and R. Y. Tsien. 1993. Movement of the free catalytic subunit of cAMP-dependent protein kinase into and out of the nucleus can be explained by diffusion. Mol. Biol. Cell 4:993–1002.
37. Hiromi, Y., and W. J. Gehring. 1987. Regulation and function of the Drosophila segmentation gene *fushi tarazu*. Cell 50:963–74.
38. Hoeffler, J. P., T. E. Meyer, Y. Yun, J. L. Jameson, and J. F. Habener. 1988. Cyclic AMP-responsive DNA-binding protein: structure based on a cloned placental cDNA. Science 242:1430–3.
39. Kim, K. S., M. K. Lee, J. Carroll, and T. H. Joh. 1993. Both the basal and inducible transcription of the tyrosine hydroxylase gene are dependent upon a cAMP response element. J Biol Chem :268:15689–95.
40. Knepel, W., J. Chafitz, and J. F. Habener. 1990. Transcriptional activation of the rat glucagon gene by the cyclic AMP-responsive element in pancreatic islet cells. Mol Cell Biol 10:6799–804.
41. Krasnow, M. A., E. E. Saffman, K. Kornfeld, and D. S. Hogness. 1989. Transcriptional activation and repression by Ultrabithorax proteins in cultured Drosophila cells. Cell 57:1031–43.
42. Landschulz, W. H., P. F. Johnson, and S. L. McKnight 1988. The leucine zipper: a hypothetical struture common to a new class of DNA binding proteins. Science 240:1759–1764.
43. Lane, M. E., and D. Kalderon. 1993. Genetic investigation of cAMP-dependent protein kinase function in Drosophila development Genes Dev 7:1229–43.
44. Lee, C. Q., Y. D. Yun, J. P. Hoeffler, and J. F. Habener. 1990. Cyclic-AMP-responsive transcriptional activation of CREB-327 involves interdependent phosphorylated subdomains. Embo J 9:4455–65.
45. Leza, M. A., and P. Hearing. 1989. Independent cyclic AMP and E1A induction of adenovirus early region 4 expression. J Virol 63:3057–64.
46. Liu, F., M. A. Thompson, S. Wagner, M. E. Greenberg, and M. R. Green. 1993. Activating transcription factor-1 can mediate Ca(2+)- and cAMP-inducible transcriptional activation. J Biol Chem 268:6714–20.
47. Maekawa, T., S. Matsuda, J. Fujisawa, M. Yoshida, and S. Ishii. 1991. Cyclic AMP response element-binding protein, CRE-BP1, mediates the E1A- induced but not the Tax-induced trans-activation. Oncogene 6:627–32.
48. Masquilier, D., N. S. Foulkes, M. G. Mattei, and P. Sassone-Corsi. 1993. Human CREM gene: evolutionary conservation, chromosomal localization, and inducibility of the transcript Cell Growth Differ 4:931–7.
49. Masson, N., M. Ellis, S. Goodbourn, and K. A. Lee. 1992. Cyclic AMP response element-binding protein and the catalytic subunit of protein kinase A are present in F9 embryonal carcinoma cells but are unable to activate the somatostatin promoter. Mol Cell Biol 12:1096–106.

50. Masson, N., H. C. Hurst, and K. A. Lee. 1993. Identification of proteins that interact with CREB during differentiation of F9 embryonal carcinoma cells [corrected and republished with original paging, article originally printed in Nucleic Acids Res 1993 Mar 11;21(5):1 163–9]. Nucleic Acids Res 21:1163–9.
51. Meinkoth, J. L., M. R. Montminy, J. S. Fink, and J. R. Feramisco. 1991. Induction of a cyclic AMP-responsive gene in living cells requires the nuclear factor CREB. Mol Cell Biol 11:1759–64.
52. Mellon, P. L., C. H. Clegg, L. A. Correll, and G. S. McKnight. 1989. Regulation of transcription by cyclic AMP-dependent protein kinase. Proc. Natl. Acad. Sci. USA 86:4887–4891.
53. Miller, J. H. 1972. Experiments in Molecular Genetics. Cold Spring Harbor Laboratory, Cold Spring Harbor
54. Mitchell, P. J., and R. Tjian. 1989. Transcriptional regulation in mammalian cells by sequence-specific DNA binding proteins. Science 245:371–8.
55. Montminy, M. R., M. J. Low, A. L. Tapia, S. Reichlin, G. Mandel, and R. H. Goodman. 1986. Cyclic AMP regulates somatostatin mRNA accumulation in primary diencephalic cultures and in transfected fibroblast cells. J Neurosci 6:1171–6.
56. Montminy, M. R., K. A. Sevarino, J. A. Wagner, G. Mandel, and R. H. Goodman. 1986. Identification of a cyclic-AMP-responsive element within the rat somatostatin gene. Proc Natl Acad Sci U S A 83:6682–6.
57. Nigg, E. A., H. Hilz, H. M. Eppenberger, and F. Dutly. 1985. Rapid and reversible transclocation of the catalytic subunit of the cAMP-dependent protein kinase type II from the golgi to the nucleus. EMBO J. 4:2801.
58. Nighorn, A., M. J. Healy, and R. L. Davis. 1991. The cyclic AMP phosphodiesterase encoded by the Drosophila dunce gene is concentrated in the mushroom body neuropil. Neuron 6:455–67.
59. Pearson, R. B., and B. E. Kemp. 1991. Protein kinase phosphorylation site sequences and consensus specificity motifs: Tabulations. In (Ed.), vol. 200. Academic Press,
60. Rehfuss, R. P., K. M. Walton, M. M. Loriaux, and R. H. Goodman. 1991. The cAMP-regulated enhancer-binding protein ATF-1 activates transcription in response to cAMP-dependent protein kinase A. J Biol Chem 266:18431–4.
61. Riabowol, K. T., J. S. Fink, M. Z. Gilman, D. A. Walsh, R. H. Goodman, and J. R. Feramisco. 1988. The catalytic subunit of cAMP-dependent protein kinase induces expression of genes containing cAMP-responsive enhancer elements. Nature 336:83–6.
62. Riabowol, K. T., M. Z. Gilman, and J. R. Feramisco. 1988. Microinjection of the catalytic subunit of cAMP-dependent protein kinase induces expression of the c-fos gene. Cold Spring Harb Symp Quant Biol 1:85–90.
63. Roesler, W. J., G. R. Vandenbark, and R. W. Hanson. 1988. Cyclic AMP and the induction of eukaryotic gene transcription. J Biol Chem 263:9063–6.
64. Ruppert, S., T. J. Cole, M. Boshart, E. Schmid, and G. Schutz. 1992. Multiple MRNA isoforms of the transcription activator protein CREB: generation by alternative splicing and specific expression in primary spermatocytes. Embo J 11: 1503–12.
65. Sheen, J. Y., and B. Seed. 1988. A simple phase-extraction assay for chloramphenicol acetyltransferase activity. Gene 67:271–277.
66. Singh, H., J. H. LeBowitz, A. J. Baldwin, and P. A. Sharp. 1988. Molecular cloning of an enhancer binding protein: isolation by screening of an expression library with a recognition site DNA. Cell 52:415–23.
67. Smolik, S. M., R. E. Rose, and R. H. Goodman. 1992. A cyclic AMP-responsive element-binding transcriptional activator in *Drosophila melanogaster*, dCREB-A, is a member of the leucine zipper family. Mol Cell Biol 12:4123–31.
68. Staden, R. 1984. Computer methods to locate signals in nucleic acid sequences. Nucleic Acids Res 12:505–19.
69. Struhl, K. 1992. Yeast GCN4 Transcriptional Activator Protein. In S. L. McKnight & K. R. Yamamoto (Ed.), Transcriptional Regulation, vol. 2. Cold Spring Harbor Press, Cold Spring Harbor.
70. Struthers, R. S., W. W. Vale, C. Arias, P. E. Sawchenko, and M. R. Montminy. 1991. Somatotroph hypoplasia and dwarfism in transgenic mice expressing a non-phosphorylatable CREB mutant Nature 350:622–4.
71. Sturrock, S. S., and J. F. Collins. 1993. MPsrch. In Edinburgh: Biocomputing Research Unit, University of Edinburgh.
72. Vinson, C. R., P. B. Sigler, and S. L. McKnight. 1989. Scissors-grip model for DNA recognition by a family of leucine zipper proteins. Science 246:911–6.
73. Waeber, G., T. E. Meyer, M. LeSieur, H. L., Hermann, N. Gerard, and J. F. Habener. 1991. Developmental stage-specific expression of the cyclic AMP response element binding protein CREB during spermatogenesis involves alternative exon splicing. Mol. Endocrinol. 5: 1418–1430.
74. Williams, J. G., A. J. Harwood, N. A. Hopper, M. N. Simon, S. Bouzid, and M. Veron. 1993. Regulation of Dictyostelium morphogenesis by cAMP-dependent protein kinase. Philos Trans R Soc Lond Biol 340:305–13.
75. Yin, J. C. P., J. S. Wallach, M. Del Vecchio, E. L. Wilder, H. Zhou, W. G. Quinn, and T. Tully. submitted.
76. Yun, Y. D., M. Dumoulin, and J. F. Habener. 1990. DNA-binding and dimerization domains of adenosine 3',5'-cyclic monophosphate-responsive protein CREB reside in the carboxyl-terminal 66 amino acids. Mol Endocrinol 4:931–9.
77. Ziff, E. B. 1990. Transcription factors: a new family gathers at the cAMP response site. Trends Genet 6:69–72.

LIST 2

Agranoff, B. W., Davis, R. E., and Brink, J. J. (1966). Chemical studies on memory fixation in goldfish. Brain Res. 1, 303–309.
Alberini, C. M., Ghirardi, M., Metz, R., and Kandel, E. R. (1994). C/EBP is an immediate-early gene required for the consolidation of long-term facilitation in Aplysia. Cell 76, 1099–114.
Ausubel, F. (Ed.). (1994). Current Protocols in Molecular Biology. (New York: John Wiley and Sons.)
Backsai, B. J., Hochner, B., Mahaut-Smith, M., Adams, S. R., Kaang, B -K., Kandel, E. R., and Tsien, R. Y. (1993). Spatially resolved dynamics of cAMP and protein kinase A subunits in Aplysia sensory neurons. Science 260, 222–226.
Baddeley, A. D. (1976). The Psychology of Memory. (New York: Basic Books).
Barondes, S. H. and Cohen, H. D. (1968). Effects of acetoxycycloheximide on learning and memory of a light-dark discrimination. Nature 218, 271–273.
Bourtchuladze, R., Frenguelli, B., Cioffi, D., Blendy, J., Schutz, G., and Silva, A. J. (1994). Normal short-term, but deficient long-term memory in mice with a targeted mutation of the cAMP Responsive Element Binding (CREB) Protein
Boynton, S. and Tully, T. (1992). latheo, a new gene involved in associative learning and memory in *Droso-* phila melanogaster, identified from P element mutagenesis. Genetics 131, 655–672.

Byers, D., Davis, R. L., and Kiger, J. A. (1981). Defect in cyclic AMP phosphodiesterase due to the dunce mutation of learning in Drosophila melanogaster. Nature 289, 79–81.

Byrne, J. H., Zwartjes, R., Homayouni, R., Critz, S. D., and Eskin, A. (1993). Roles of second messenger pathways in neuronal plasticity and in learning and memory. In Advances in Second Messenger and Phosphoprotein Research, S. Shenolikar and A. C. Nairn eds. (New York: Raven Press.) pp. 47–107.

Chen, C. N., Denome, S., and Davis, R. L. (1986). Molecular analysis of cDNA clones and the corresponding genomic coding sequences of the Drosophila dunce+ gene, the structural gene for cAMP phosphodiesterase. Proc Natl Acad Sci USA 83, 9313–7.

Dash, P. K., Hochner, B., and Kandel, E. R. (1990). Injection of the cAMP-responsive element into the nucleus of Aplysia sensory neurons blocks long-term facilitation. Nature 345, 718–721.

Davis, H. P. and Squire, L. R. (1984). Protein synthesis and memory: A review. Psychol. Bull. 96, 518–559.

deGroot, R. P. and Sassone-Corsi, P. (1993). Hormonal control of gene expression: Multiplicity and versatility of cyclic adenosine 3',5'-monophosphate-responsive nuclear regulators. Mol. Endocrinol. 7, 145–153.

Drain, P., Folkers, E., and Quinn, W. G. (1991). cAMP-dependent protein kinase and the disruption of learning in transgenic flies. Neuron 6, 71–82.

Dudai, Y., Jan, Y. N., Byers, D., Quinn, W. G., and Benzer, S. (1976). Dunce, a mutant of Drosophila deficient in learning. Proc. Natl. Acad. Sci. USA 73, 1684–1688.

Dura, J-M., Preat, T. and Tully, T. (1993). Identification of linotte, a new gene affecting learning and memory in Drosophila melanogaster. J. Neurogenet. 9, 1–14.

Dwarki, V. J., Montminy, M. and Verma, I. M. (1990). Both the basic region and the 'leucine zipper' domain of the cyclic AMP response element binding (CREB) protein are essential for transcriptional activation. EMBO J. 9, 225–232.

Ebbinghaus, H. (1885). Uber das Gedachtnis. (Dover, New York)

Folkers, E., Drain, P., and Quinn, W. G. (1993). radish, a Drosophila mutant deficient in consolidated memory. Proc. Natl. Acad. Sci. 90, 8123–8127.

Foulkes, N. and Sassone-Corsi, P. (1992). More is better: activators and repressors from the same gene. Cell 68, 411414.

Foulkes, N. S., Borrelli, E., and Sassone, C. P. (1991). CREM gene: use of alternative DNA-binding domains generates multiple antagonists of cAMP-induced transcription. Cell 64,739–49.

Foulkes, N. S., Melistrom, B., Benusiglio, E., and Sassone-Corsi, P. (1992). Developmental switch of CREM function during spermatogenesis: From antagonist to transcriptional activator. Nature 355, 80–84.

Frey, U., Huang, Y., Y., and Kandel, E. R. (1993). Effects of cAMP stimulate a late stage of LTP in hippocampal CA1 neurons. Science 260, 1661–1664.

Gonzalez, G. A. and Montminy, M. R. (1989). Cyclic AMP stimulates somatostatin gene transcription by phosphorylation of CREB at serine 133. Cell 59, 675–680.

Habener, J. F. (1990). Cyclic AMP response element binding proteins: a cornucopia of transcription factors. Mol. Endocrinol. 4, 1087–1094.

Hai, T. and Curran, T. (1991). Cross-family dimerization of transcription factors Fos/Jun and ATF/CREB alters DNA binding specificity. Proc Natl Acad Sci USA 88, 3720–4.

Hai, T. Y., Liu, F., Coukos, W. J., and Green, M. R. (1989). Transcription factor ATF CDNA clones: An extensive family of leucine zipper proteins able to selectively form DNA binding heterodimers. Genes & Dev. 3, 2083–2090.

Hovemann, B., Richter, S., Walldorf, U. and Cziepluch, C. (1988). Two genes encode related cytoplasmic elongation factors 1 alpha (EF-1 α) in Drosophila melanogaster with continuous and stage specific expression. Nucleic Acids Res. 16, 3175–3194.

Huang, Y. Y. and Kandel, E. R. (1994). Recruitment of long-lasting and protein kinase A-dependent long-term potentiation in the CA1 region of hippocampus requires repeated tetanization. Learning and Memory (Cold Spring Harbor) 1, 74–82.

Kaang, B. K., Kandel, E. R., and Grant, S. G. (1993). Activation of cAMP-responsive genes by stimuli that produce long-term facilitation in Aplysia sensory neurons. Neuron 10, 427–35.

Kandel, E. R., Klein, M., Hochner, B., Shuster, M., Siegelbaum, S., Hawkins, R. D., Glanzman, D. L., Castellucci, V. F., and Abrams, T. W. (1987). Synaptic modulation and learning: New insights into synaptic transmission from the study of behavior. In Synaptic Function, G. M. Edelmam, W. E. Gall, and W. M. Cowan eds. (New York: John Wiley and Sons.) pp.

Kandel, E. R. and Schwartz, J. H. (1982). Molecular biology of an elementary form of learning: Modulation of transmitter release by cAMP. Science 218, 433–443.

Landschulz, W. H., Johnson, P. F., and McKnight, S. L. (1988). The leucine zipper: a hypothetical struture common to a new class of DNA binding proteins. Science 240, 1759–1764.

Levin, L. R., Han, P. L., Hwang, P. M., Feinstein, P. G., Davis, R. L., and Reed, R. R. (1992). The Drosophila learning and memory gene rutabaga encodes a Ca2+/Calmodulin-responsive adenylyl cyclase. Cell 68, 479–89.

Livingstone, M. S., Sziber, P. P., and Quinn, W. G. (1984). Loss of calcium/calmodulin responsiveness in adenylate cyclase of rutabaga, a Drosophila learning mutant. Cell 37, 205–215.

Montarolo, P. G., Goelet, P., Castellucci, V. G., Morgan, J., Kandel, E. R., and Schacher, S. (1986). A critical period for macromolecular synthesis in long-term heterosynaptic facilitation in Aplysia. Science 234, 1249–1254.

Parker, V. P., Falkenthal, S. and Davidson, N. (1985). Characterization of the niyositz light-chain-2 gene of Drosophila melanogaster. Mol. Cell Biol. 5, 3058–3068.

Quinn, W. G., Harris, W. A., and Benzer, S. (1974). Conditioned behavior in Drosophila melanogaster. Proc. Nat. Acad. Sci. USA 71, 708–712.

Rosenzweig, M. R. and Bennett, E. L. (1984). Basic processes and modulatory influences in the stages of memory formation. In Neurobiology of Learning and Memory, G. Lynch, J. L. McGaugh, and N. M. Weinberger eds. (New York: The Guilford Press.) pp. 263–288

Rubin, G. M. and Spradling, A. (1982). Genetic transformation of Drosophila with transposable element vectors. Science 218, 348–53.

Schacher, S., Castellucci, V. F., and Kandel, E. R. (1988). cAMP evokes long-term facilitation in Aplysia sensory neurons that requires new protein synthesis. Science 240, 1667–1669.

Skoulakis, E. M., Kalderon, D., and Davis, R. L. (1993). Preferential expression in mushroom bodies of the catalytic subunit of protein kinase A and its role in learning and memory. Neuron 11, 197–208.

Sokal, R. R. and Rohlf, F. J. (1981). Biometry 2nd Ed. (New York: W. H. Freeman and Company). Spradling, A. C. and Rubin, G. M. (1982). Transposition of cloned P elements into Drosophila germ line chromosomes. Science 218, 341–7.

Tully, T. and Quinn, W. G. (1985). Classical conditioning and retention in normal and mutant *Drosophila melanogaster*. J. Comp. Physiol. 157, 263–277.

Tully, T. and Gold, D. (1993). Differential effects of dunce mutations on associative learning and memory in Drosophila. J. Neurogenet. 9,55–71.

Tully, T., Preat, T., Boynton, S. C., and Del Vecchio, M. (1994). Genetic dissection of consolidated memory in *Drosophila melanogaster*. Cell 79, 35–47.

Yamamoto, K. K., Gonzalez, G. A., Biggs, W. H. I., and Montminy, M. R. (1988). Phosphorylation-induced binding and transcriptional efficacy of nuclear factor CREB. Nature 334, 494–8.

LIST 3

Alberini, C. M., Ghirardi, M., Metz, R., and Kandel, B. R. (1994). C/EBP is an immediate-early gene required for the consolidation of long-term facilitation in Aplysia. Cell 76, 1099–114.

Armstrong, R. C. and Montminy, M. R. (1993). Transsynaptic control of gene expression. Annu. Rev. Neurosci. 16, 17–29.

Backsai, B. J., Hochner, B., Mahaut-Smith, M., Adams, S.R., Kaang, B-K., Kandel, E. R., and Tsien, R. Y. (1993). Spatially resolved dynamics of cAMP and protein kinase A subunits in Aplysia sensory neurons. Science 260. 222–226.

Bailey, C. H. and Kandel, E. R, (1994). Structural changes underlying long-term memory storage in Aplysia: a molecular perspective. Sem. Neurosci. 6, 3544.

Bourtchuladze, R. Frenguelli, B., Cioffi, D., Blendy, J., Schutz, G., and Silva, A. J. (1994). Normal short-term, but deficient long-term memory in mice with a targeted mutation of the cAMP Responsive Element Binding (CREB) Protein Boynton, S. and Tully, T. (1992). latheo, a new gene involved in associative learning and memory in *Drosophila melanogaster*, identified from P clement mutagenesis. Genetics 131, 655–672.

Buonomano, D. V. and Byrne, J. H. (1990). Long-term synaptic changes produced by a cellular analog of classical conditioning in Aplysia. Science 249,420–423.

Byrne, J. H., Zwartjes, R., Homayouni, R., Critz, S. D., and Eskin, A. (1993). Roles of second messenger pathways in neuronal plasticity and in learning and memory. In Advances in Second Messenger and Phosphoprotein Research, S. Shenolikar and A. C. Nairn eds. (New York: Raven Press.) pp. 47–107.

Carew, T. J., Pinsker, H. M. and Kandel, E. R. (1972). Long-term habituation of a defensive withdrawal reflex in Aplysia. Science 175, 451–454.

Castellucci, V. F., Blumenfeld, H., Goelet, P. and Kandel, E. R. (1989). Inhibitor of protein synthesis blocks long-term behavioral sensitization in the isolated gill-withdrawal reflex of Aplysia. J. Neurobiol. 20, 1–9.

Dash, P. K., Hochner, B., and Kandel, B. R. (1990). Injection of the cAMP-responsive element into the nucleus of Aplysia sensory neurons blocks long-term facilitation. Nature 345, 718–721.

Dash, P. K., Karl, K. A., Colicos, M. A., Prywes, R. and Kandel, E. R. (1991). cAMP response element-binding protein is activated by $Ca^{2+}$/calmodulin- as well as cAMP-dependent protein kinase. Proc. Natl. Acad. Sci. USA 88, 5061–5065.

Davis, H. P. and Squire, L. R. (1984). Protein synthesis and memory: A review. Psychol. Bull. 96, 518–559.

deGroot, R. P. and Sassone-Corsi, P. (1993). Hormonal control of gene expression: Multiplicity and versatility of cyclic adenosine 3',5'-monophosphate-responsive nuclear regulators. Mol. Endocrinol. 7, 145–153.

Drain, P., Folkers, E. and Quinn, W. G. (1991). cAMP-dependent protein kinase and the disruption of learning in transgenic flies. Neuron 6, 71–82.

Dura, J-M., Preat, T. and Tully, T. (1993). Identification of linotte, a new gene affecting learning and memory in *Drosophila melanogaster*. J. Neurogenet. 9, 1–14.

Ebbinghaus, H. (1885). Über das Gedächtnis, In H. A. Ruger and C. E. Bussenius, trans. (New York, Dover).

Erber, J. (1976). Retrograde amnesia in honeybees (Apis mellifera camica). J. Comp. Physiol. Psychol. 90, 41–46.

Foulkes, N. and Sassone-Corsi, P. (1992). More is better: activators and repressors from the same gene. Cell 68, 411–414.

Foulkes, N. S., Mellstrom, B., Benusiglio, E., and Sassone-Corsi, P. (1992). Developmental switch of CREM function during spermatogenesis: From antagonist to transcriptional activator. Nature 355, 80–84.

Frank, D. A. and Greenberg, M. E. (1994). CREB: a mediator of long-term memory from mollusks to mammals. Cell 79, 5–8.

Frey, U., Huang, Y., Y., and Kandel, E. R. (1993). Effects of cAMP stimulate a late stage of LTP in hippocampal CA1 neurons. Science 260, 1661–1664.

Frost, W. N., Castellucci, V. F., Hawkins, R. D. and Kandel, E. R. (1985). Monosynaptic connections from the sensory neurons of the gill- and siphon-withdrawal reflex in Aplysia participate in the storage of long-term memory for sensitization. Proc. Natl. Acad. Sci. USA 82, 8266–8269.

Gall, C. M. and Lauterborn, J. C. (1991). Activity-dependent neuronal gene expression: a potential memory mechanism? In Memory: Organization and Locus of Change, L. R. Squire, N. M. Weinberger. G. Lynch and J. L. McGaugh, eds. (New York: Oxford), pp. 301–329.

Ginty, D. D., et at. *Science* 260, 238–241 (1993).

Goelet, P., Castellucci, V. F., Schacher, S. and Kandel, E. R. (1986). the long and the short of long-term memory—a molecular framework. Nature 322,419–422.

Greenough, W. T. (1984). Structural correlates of information storage in the mammalian brain: a review and hypothesis. TINS 7, 229–283.

Habener, J. F. (1990). Cyclic AMP response element binding proteins: a cornucopia of transcription factors. Mol. Endocrinol, 4, 1087–1094.

Hintzman, D. L. (1974). Theoretical implications of the spacing effect. In Theories in Cognitive Psychology: The Loyola Symposium, R. L. Solso, ed. (Hillsdale N.J.: Lawrence Erlbaum Assoc.), pp. 77–99.

Huang, Y. Y. and Kandel, E. R. (1994). Recruitment of long-lasting and protein kinase A-dependent long-term potentiation in the CA1 region of hippocampus requires repeated tetanization. Learning and Memory (Cold Spring Harbor) 1, 74–82.

Jaffe, K. (1980). Effects of cycloheximide on protein synthesis and memory in praying mantis. Physiol. Behav. 25, 367–371.

Kaang, B. K., Kandel, E. R., and Grant, S. G. (1993). Activation of cAMP-responsive genes by stimuli that produce long-term facilitation in Aplysia sensory neurons. Neuron 10, 427–35.

Kandel, E. R., Klein, M., Hochner, B., Shuster, M., Siegelbaum, S., Hawkins, R. D., Glanzman, D. L., Castellucci, V. F., and Abrams, T. W. (1987). Synaptic modulation and learning: New insights into synaptic transmission from the study of behavior. In Synaptic Function, G. M. Edelmam,W. E. Gall, and W. M. Cowan eds. (New York: John Wiley and Sons.) pp.

Levin, L. R., Han, P. L., Hwang, P. M., Feinstein, P. G., Davis, R. L., and Reed, R. R. (1992). The Drosophila learning and memory gene rutabaga encodes a Ca2+/Calmodulin-responsive adenylyl cyclase. Cell 68, 479–89.

Lewis, D. (1960) Quantitative Methods in Psychology. (New York N.Y.: McGraw-Hill).

Livingstone, M. S., Sziber, P. P. and Quinn, W. G. (1984). Loss of calcium/calmodulin responsiveness in adenylate cyclase of rutabaga, a Drosophila learning mutant. Cell 37, 205–215.

Meyer, T. E., Waeber, G., Lin, J., Beckmann, W. and Habener, J. F. (1993). The promoter of the gene encoding 3',5'-cyclic adenosine monophosphate (cAMP) response element binding protein contain cAMP response elements: evidence for positive autoregulation of gene transcription. Endocrinology 132, 770–780.

Montarolo, P. G., Goelet, P., Castellucci, V. G., Morgan, J., Kandel, E. R., and Schacher, S. (1986). A critical period for macromolecular synthesis in long-term heterosynaptic facilitation in Aplysia. Science 234,1249–1254.

Nazif, F. A., Byrne, J. H. and Cleary, L. J. (1991). cAMP induces long-term morphological changes in sensory neurons of Aplysia. Brain Res. 539, 324–327.

Qiu, Y. and Davis, R. L. (1993) Genetic dissection of the learning(memory gene dunce of Drosophila melanogaster. Genes Develop. 7, 1447–1458.

Rubin, G. M. and Spradling, A. (1982). Genetic transformation of Drosophila with transposable element vectors. Science 218, 348–53.

Skoulalis, E. M., Kalderon, D., and Davis, R. L. (1993). Preferential expression in mushroom bodies of the catalytic subunit of protein kinase A and its role in learning and memory. Neuron 11, 197–208.

Sokal, R. R. and Rohlf, F. J. (1981). Biometry 2nd Ed. (New York: W. H. Freeman and Company). Spradling, A. C. and Rubin, G. M. (1982). Transposition of cloned P elements into Drosophila germ line chromosomes. Science 218, 341–7.

Stewart, M. G. (1991). Changes in dendritic and synaptic structure in chick forebrain consequent on passive avoidance learning. In Neural and Behavioural Plasticity: The use of the domestic chick as a model, R. J. Andrew, ed. (Oxford Oxford), pp. 305–328.

Tully, T. and Gold, D. (1993). Differential effects of dunce mutations on associative learning and memory in Drosophila. J. Neurogenet. 9, 55–71.

Tully, T. and Quinn, W. G. (1985). Classical conditioning and retention in normal and mutant Drosophila melanogaster. J. Comp. Physiol. 157,.263–277.

Tully, T., Preat, T., Boynton, S. C., and Del Vecchio, M. (1994). Genetic dissection of consolidated memory in Drosophila. Cell 79, 3547.

Yamamoto, K. K., Gonzalez, G. A., Biggs, W. H. I., and Montminy, M. R. (1988). Phosphorylation-induced binding and transcriptional efficacy of nuclear factor CREB. Nature 334, 494–8.

LIST 4

1. R. G. Knowels, S. Moncada, *Biochem. J.* 298, 249 (1994); C. Nathan, Q.-w. Xie, *J. Biol. Chem* 269, 13725 (1994); M. A. Marietta, *J. Biol. Chem.* 268, 12231 (1993).
2. D. S. Bredt, et al., *Nature* 351, 714–718 (1991).
3. S. Lamas, P. A. Marsden, G. K. Li, P. Tempst, T. Michel, *Proc. Natl. Acad. Sci. USA* 89, 6348–6352 (1992).
4. C. R. Lyons, G. J. Orloff, J. M. Cunningham, *J. Biol. Chem.* 267, 6370 (1992); C. J. Lowenstein, C. S. Glatt, D. S. Bredt, S. H. Snyder, *Proc. Natl. Acad. Sci. USA* 89, 6711 (1992); W. C. Sessa, et al., *J. Biol. Chem.* 267, 15274(1992); D. A. Geller, et al., *Proc. Natl. Acad. Sci. USA* 90, 3491 (1993).
5. Q. Xie, et al., *Science* 256, 225–228 (1992).
6. J. L. Dinerman, T. M. Dawson, M. J. Schell, A. Snowman, S. H. Snyder, *Proc. Natl. Acad. Sci. USA* 91, 4214–4218 (1994).
7. T. M. Dawson, V. L. Dawson, S. H. Snyder, *Ann. Neurol.* 32, 297 (1992); C. Nathan, *FASEB J.* 6, 3051 (1992); S. Moncada, E. A. Higgs, *N. Eng. J. Med.* 329, 2002–2012 (1993).T. Michel, T. W. Smith, *Amer. J. Cardiol.* 72, 33C (1993); E. M. Schuman, D. V. Madison, *Annu. Rev. Neurosci.* 17, 153–83 (1994).
8. R. M. J. Palmer, A. G. Ferridge, S. Moncada, *Nature* 327, 524 (1987); R. M. J. Palmer, D. S. Ashton, S. Moncada, *Nature* 333, 664 (1988); L. J. Ignarro, G. M. Buga, K. S. Wood, R. E. Byrns, G. Chaudhuri, *Proc. Natl. Acad. Sci. USA* 84, 9265 (1987).
9. M. A. Marletta, P. S. Yoon, R. Iyengar, C. D. Leaf, J. S. Wishnok, *Biochemistry* 21, 8706 (1988); J. B. Hibbs, R. R. Taintor, Z. Vavrin, E. M. Rachlin, *Biochem. Biophys. Res. Comm.* 157, 87 (1989); D. J. Steuhr, C. F. Nathan, *J. Exp. Med* 169, 1543 (1989).
10. M. Radomski, R. M. J. Palmer, S. Moncada, *Proc. Natl. Acad. Sci. USA* 87, 5193 (1990); J. E. Albina, J. A. Abate, W. L. Henry, *J. Immunol* 147, 144 (1991); R. Zatz, G. Nucci, *Am. J. Physiol.* 261, F360 (1992); A. Ialenti, A. Ianaro, S. Moncada, M. D. Rosa, *Eur. J. Pharmacol* 211, 177 (1992).
11. Y. Uemura, N. W. Kowall, M. F. Beal, *Ann. Neurol.* 27, 620–625 (1990).
12. Y. Uemura, N. W. Kowall, M. F. Beal, *Ann. Neurol.* 27, 620 (1990); V. L. Dawson, T. M. Dawson, E. D. London, D. S. Bredt, S. H. Snyder, *Proc. Natl. Acad. Sci.* 88, 6368 (1991); S. Z. Lei, Z.-H. Pan, S. K. Aggarwal, *Neuron* 8, 1087 (1992); H. Prast, A. Phillipu, *Eur. J. Pharmacol.* 216, 139 (1992); N. Peunova, G. Enikolopov, *Nature* 364, 450 (1993).
13. D. S. Bredt, S. H. Snyder, *Neuron* 13, 301 (1994); A. J. Roskams, D. S. Bredi, T. M. Dawson, G. V. Ronnett, *Neuron* 13, 289 (1994).
14. G. M. Edelman, J. A. Gally, *Proc. Nati. Acad. Sci. USA* 89, 11651–11652 (1992).
15. G. A. Bohme, C. Bon, J.-M. Stutzman, A. Doble, J.-C. Blanchard, *Eur. J. Pharmacol.* 199, 379 (1991); E. M. Schuman, D. V. Madison, *Science* 254, 1503 (1991); T. J. O'Dell, R. D. Hawkins, E. R. Kandel, O. Arancio, *Proc. Natl. Acad. Sci. USA* 88, 11285 (1991); K. Shibuki, D. Okada, *Nature* 349, 326 (1991); J. E. Haley, G. L. Wilcox, P. F. Chapman, *Neuron* 8, 211 (1992); M. Zhuo, S. A. Small, E. R. Kandel, R. D. Hawkins, *Science* 260, 1946 (1993); M. Zhuo, E. R. Kandel, R. D. Hawkins, *NeuroReport* 5, 1033 (1994).
16. P. F. Chapman, C. M. Atkins, M. T. Allen, J. E. Haley, J. E. Steinmetz, *NeuroReport* 3, 567 (1992); C. Holscher, S. P. R. Rose, *Neurosci. Lett.* 145, 165 (1992); G. A. Bohme, et al., *Proc. Natl. Acad. Sci. USA* 90, 9191 (1993); N. S. Rickard, K. T. Ng, M. E. Gibbs, *Behav. Neurosci.* 108, 640–644 (1994).
17. P. L. Huang, T. M. Dawson, D. S. Bredt, S. H. Snyder, M. C. Fishman, *Cell* 75, 1273–1286 (1993).

18. T. J. O'Dell, et al., *Science* 265, 542–546 (1994).
19. We have screened 6×10⁴ plaques of a genomic Drosophila λDASH library with the 1.3 kb Bgl 11 fragment of rat neuronal NOS cDNA (residues 3282–4573) under low stringency conditions of 40% formamide as described in W. M. McGinnis et al., *Nature* 308, 428 (1984). Fifty positive phage were purified and grouped based on inter se hybridization. The contig containing the 2.4R fragment of dNOS was comprised of 15 phage clones. Regions of cross-hybridization to the rat probe were identified, subcloned and three of them were sequenced. The other two did not contain sequences homologous to any protein in the database. A Drosophila head cDNA library (a gift from P. Salvaterra) was screened with the 2.4R fragment isolated from phage clone λ8.11 in standard conditions. All phage purification and cloning steps were done with standard methods (J. Sambrook, E. F. Fritsch, T. Maniatis, Molecular cloning: A Laboratory Manual (Cold Spring Harbor Laboratory, Cold Spring Harbor, N.Y., 1989). cDNA fragments were subcloned into Bluescript (Stratagene) and sequenced on both strands with Sequenase 2.0 (USB). Single-letter abbreviations for the amino acid residues are as follows: A, Ala;C, Cys; D, Asp; E, Glu; F, Phe; G, Gly; H, His; I, Ile; K, Lys; L, Leu; M, Met; N, Asn; P, Pro; Q, Gin; R, Arg; S, Ser; T, Thr; V, Val; W, Trp; Y, Tyr.
20. D. R. Cavener, *Nucleic Acids Res* 15, 1353–1361 (1987).
21. K. T. O'Neil, W. F. DeGrado, *Trends Biochem. Sci.* 15, 59–64 (1990).
22. R. B. Pearson, B. E. Kemp, *Meth. Enzymol.* 200, 62–81 (1991).
23. R. G. Franks, S. T. Crews, *Mech. Dev.* 45, 269 (1994); H.-P. Gerber, et al., *Science* 263, 808 (1994); M. Reguiski, N. McGinnis, R. Chadwick, W. McGinnis, *EMBO J.* 6, 767(1987).
24. The expression construct for activity assays contained dNOS cDNA (with an XbaI site engineered immediately upstream of the ATG codon) cloned into the XbaI and SmaI sites of the pCGN expression vector [M. Tanaka and W. Herr, *Cell* 60, 375 (1990)]. 293 human kidney cells were transfected with 15 μg of the dNOS construct, or vector DNA, and precipitated with calcium phosphate as described in [M. J. Imperiale, L. T. Feldman and J. R. Nevins, *Cell* 35, 127 (1983)]. Cells were collected 2 days later and protein extracts were prepared as described in [J. Sambrook, E. F. Fritsch, T. Maniatis, Molecular cloning: A Laboratory Manual (Cold Spring Harbor Laboratory, Cold Spring Harbor, N.Y., 1989)].
25. The fusion protein for raising anti-DNOS antibodies was made by cloning a 0.29 kb Eam1105I-SacI fragment of dNOS cDNA (this fragment codes for 97 N-terminal amino acids of dNOS ORF) into EcoRI site of pGEX-KG [K. Guan and J. E. Dixon *Anal. Biochem.* 192, 262 (1991)]. The fusion protein was expressed in BL21 *E. coli* strain and purified over Glutathione-Sepharose columns (Pharmacia) as described in [G. J. Hannon, D. Demetrick, D. Beach, *Genes & Dev.*, 7, 2378 (1993)]. Immunization of rabbits, and serum preparation, was done by Hazleton Research Products, Inc. (Denver). The DNOS protein was detected on Western blots using a 1:500 dilution of rabbit serum, and cross-reacting bands were visualized with anti-rabbit alkaline phosphatase conjugate (Promega) according to the protocol provided.
26. The enzymatic assay was done essentially as described previously (D. Bredt and S. Snyder, Proc. Natl. Acad. Sci. USA, 87, 682 (1990)]. A 100 ml reaction mixture containing 25 μl (50–100 μg) of soluble protein extract, 50 mM Hepes pH 7.4, 3 μM FAD, 3 μM FMN, 10 μM tetrahydrobiopterin (ICN), 1 mM DTT, 0.8 mM CaCl$_2$, 1 mM NADPH, 10 μg/ml calmodulin, 2 μl of [³H]L-arginine (35.7 Ci/mmol, NEN) and 50 mM L-valine in was incubated for 60 min. at 37° C. The reaction was stopped with 0.5 ml 20 mM Hepes pH 5.5, 2 mM EDTA, 2 mM EGTA, loaded on 0.5 ml Dowex AG 50WX-8 (Na⁺ form) column and eluted with 3×0.5 ml of the stop buffer. Radioactivity present in the eluent was quantified in a scintillation counter.
27. R. Iyengar, D. J. Steuhr, M. A. Marletta, *Proc. Natl Acad. Sci. USA* 84, 6369–6373 (1987).
28. D. S. Bredt, S. H. Snyder, *Proc. Natl. Acad. Sci. USA* 87, 682–685 (1990).
29. D. D. Rees, R. M. J. Palmer, R. Schulz, H. F. Hodson, S. Moncada, *Br. J. Pharmacol.* 101, 746–752 (1990).
30. Heads and bodies of adult flies were separated on sieves. Total RNA was isolated by the guanidinium isothiocyanate method [P. Chomczynski and N. Sacchi, *Anal. Biochem.* 162, 156 (1987)]. Poly(A)⁺ RNA selection, Northern blot and hybridization were done with standard methods (J. Sambrook, E. F. Fritsch, T. Maniatis, Molecular cloning: A Laboratory Manual (Cold Spring Harbor Laboratory, Cold Spring Harbor, N.Y., 1989). The blot was hybridized with random-primed dNOS cDNA (10⁶cpm/ml), washed in 0.1×SSC and 0.1% SDS at 65° C. and exposed to X-ray film for 72 hrs. We have used two 25-mer primers [corresponding to residues 1374–1399 (the top primer) and 1793–1817 (the bottom primer) in the dNOS sequence] to amplify fragments of two dNOS splice products. Each RT-PCR reaction contained 30 ng of poly(A)⁺ head RNA [J. C. P. Yin et al., *Mol. Cell Biol.*, submitted]. In the first stage (RT), 90 ng of the bottom primer and 5 U of rTth polymerase (Perkin-Elmers) were added and the mixture was incubated in the MJ Research Minicycler™ in the following sequence of conditions: 95°/1 min., 67°/45sec, 70°/13 min. The second stage (PCR) was carried out as follows: 94°/45 sec., 63°/45 sec., 70°/90 sec. and was repeated for 35 cycles. Products of the reaction were analyzed on a denaturing polyacrylamide (8%) gel. Bands of interest were isolated, re-amplified, cloned into pCR1000 (InVitrogen) and sequenced with Sequenase kit (USB).
31. T. Ogura, T. Yokoyama, H. Fujisawa, Y. Kurashima, H. Esumi, *Biochem. Biophys. Res. Commun.* 193, 1014–1022 (1993).
32. M. W. Radomski, J. F. Martin, S. Moncada, *Philos. Trans. R. Soc. Lond. B Biol. Sci.* 334, 129–133 (1992).
33. M. R. Elphick, I. C. Green, M. O'Shea, *Brain Res.* 619, 344–346 (1993).
34. J. M. C. Ribeiro, R. H. Nussenzweig, *FEBS Let.* 330, 165–168 (1993).
35. R. Elofsson, M. Carlberg, L. Moroz, L. Nezlin, D. Sakharov, *NeuroReport* 4, 279–282 (1993).
36. A. Gelperin, *Nature* 369, 61–63 (1994).
37. T. M. Dawson, D. S. Bredt, M. Fotuhi, P. M. Hwang, S. H. Snyder, *Proc. Natl. Acad. Sci. USA* 88, 7797 (1991); B. T. Hope, G. J. Michael, K. M. Knigge, S. R. Vincent, *Proc. Natl. Acad. Sci. USA* 88, 2811 (1991).
38. U. Muller, E. Buchner, *Naturwissenschaft* 80, 524–526 (1993).
39. J. C. P. Yin, et al., *Cell, in press* (1994); P. Drain, E. Folkers, W. G. Quinn, *Neuron* 6, 71(1991).
40. P. A. Karplus, M. J. Daniels, J. R. Herriott, *Science* 251, 60–66 (1991).
41. V. P. Parker, S. Falkenthal, N. Davidson, *Mol. Cell Biol.* 5, 3058 (1985).

What is claimed is:

1. A method of potentiating long term memory in an animal comprising treating said animal to increase the level of a homodimer of an endogenous activator relative to the level of said homodimer present in said animal prior to said treatment, wherein said activator is a CREB/CREM/ATF-1 subfamily member.

2. The method of claim 1 wherein said animal is Drosophila and the activator homodimer is a dCREB2a homodimer.

3. The method of claim 1 wherein said animal is a mammal.

4. A method of potentiating long term memory in an animal comprising treating said animal to decrease the level of a heterodimer of an endogenous activator and an endogenous repressor relative to the level of said heterodimer present in said animal prior to said treatment, wherein said activator is a CREB/CREM/ATF-1 subfamily member and said repressor is an antagonist of said activator.

5. The method of claim 4 wherein said animal is Drosophila and the activator-repressor heterodimer is a dCREB2a-dCRB2b heterodimer.

6. The method of claim 3 wherein said animal is a mammal.

7. A method of potentiating long term memory in an animal comprising treating said animal to decrease the level of a homodimer of an endogenous repressor relative to the level of said homodimer present in said animal prior to said treatment, wherein said repressor is an antagonist of a CREB/CREM/ATF-1 subfamily member.

8. The method of claim 7 wherein said animal is Drosophila and the repressor homodimer is a dCREB2b homodimer.

9. The method of claim 5 wherein the animal is a mammal.

10. A method of modulating long term memory in an animal comprising treating said animal to modulate the expression of an endogenous gene, said gene selected from the group consisting of a gene encoding an activator and a gene encoding an antagonist of said activator, wherein said activator is a CREB/CREM/ATF-1 subfamily member.

11. The method of claim 10 wherein said animal is a mammal and the gene is selected from the group consisting of mammalian CREB and mammalian CREM genes.

12. The method of claim 10 wherein the gene encodes said activator and inducing said gene results in the potentiation of long term memory.

13. The method of claim 10 wherein the gene encodes said antagonist and inducing said gene results in the blocking of long term memory.

14. The method of claim 10 wherein said animal is Drosophila and the gene is selected from the group consisting of dCREB2 and dCREB1 genes.

15. A method of modulating long term memory in an animal comprising treating said animal to modulate the level of an endogenous activator and the level of an endogenous antagonist of said activator, wherein said activator is a CREB/CREM/ATF-1 subfamily member, and wherein long term memory is potentiated in the animal when the net amount of functional activator (ΔC) is greater than zero.

16. The method of claim 12 wherein the animal is a mammal.

17. The method of claim 12 wherein the animal is Drosophila.

* * * * *

UNITED STATES PATENT AND TRADEMARK OFFICE
CERTIFICATE OF CORRECTION

PATENT NO. : 6,051,559
DATED : April 18, 2000
INVENTOR(S) : Timothy P. Tully and Jerry Chi-Ping Yin It is certified that error appears in the above-identified patent and that said Letters Patent is hereby corrected as shown below:

Claim 6, column 99,
Line 36, delete "3" and insert --4--.

Claim 9, column 100,
Line 15, delete "5" and insert --7--.

Claim 16, column 100,
Line 42, delete "12" and insert --15--.

Claim 17, column 100,
Line 44, delete "12" and insert --15--.

Signed and Sealed this

Twenty-sixth Day of June, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 1083 base pairs
       (B) TYPE: nucleic acid
       (C) STRANDEDNESS: double
       (D) TOPOLOGY: linear (ii) MOLECULE TYPE: other nucleic acid
       (A) DESCRIPTION: /desc = "cDNA and PCR analysis"

(ix) FEATURE:
       (A) NAME/KEY: CDS
       (B) LOCATION: 1..1080

(xi) SEQUENCE DESCRIPTION: SEQ ID NO:1:

```
ATG GAC AAC AGC ATC GTC GAG GAG AAC GGC AAC TCG TCG GCG GCA TCG      48
Met Asp Asn Ser Ile Val Glu Glu Asn Gly Asn Ser Ser Ala Ala Ser
 1               5                  10                  15

GGC TCC AAT GAC GTG GTC GAT GTC GTT GCC CAA CAG GCG GCG GCA GCG      96
Gly Ser Asn Asp Val Val Asp Val Val Ala Gln Gln Ala Ala Ala Ala
             20                  25                  30

GTG GGC GGC GGC GGT GGA GGA GGA GGC GGC GGC GGT GGT AAC              144
Val Gly Gly Gly Gly Gly Gly Gly Gly Gly Gly Gly Gly Asn
         35                  40                  45

CCC CAG CAG CAG CAA CAG AAC CCA CAA AGT ACA ACG GCC GGC GGT CCA      192
Pro Gln Gln Gln Gln Gln Asn Pro Gln Ser Thr Thr Ala Gly Gly Pro
 50                  55                  60

ACG GGT GCG ACG AAC AAC GCC CAG GGA GGC GGA GTG TCC TCC GTG CTG      240
Thr Gly Ala Thr Asn Asn Ala Gln Gly Gly Gly Val Ser Ser Val Leu
 65                  70                  75                  80

ACC ACC ACC GCC AAC TGC AAC ATA CAA TAC CCC ATC CAG ACG CTG GCG      288
Thr Thr Thr Ala Asn Cys Asn Ile Gln Tyr Pro Ile Gln Thr Leu Ala
                 85                  90                  95

CAG CAC GGA CTG CAG GTG AGC ATT TGG GGA CCG GGT GCT TGG TGT CAA      336
Gln His Gly Leu Gln Val Ser Ile Trp Gly Pro Gly Ala Trp Cys Gln
            100                 105                 110

CTG TCG AGT GTC AGG TGT TAC GGA TCC CAG CCA GAA GTG GCT ACC AAG      384
Leu Ser Ser Val Arg Cys Tyr Gly Ser Gln Pro Glu Val Ala Thr Lys
            115                 120                 125

GAT GTG CAG TCC GTG ATA CAG GCC AAT CCC TCG GGA GTC ATA CAG ACA      432
Asp Val Gln Ser Val Ile Gln Ala Asn Pro Ser Gly Val Ile Gln Thr
130                 135                 140

GCA GCT GGA ACC CAG CAG CAG CAA CAG GCG CTG GCC GCC GCC ACA GCG      480
Ala Ala Gly Thr Gln Gln Gln Gln Gln Ala Leu Ala Ala Ala Thr Ala
145                 150                 155                 160

ATG CAG AAG GTG GTC TAC GTG GCC AAG CCG CCG AAC TCG ACG GTC ATC      528
Met Gln Lys Val Val Tyr Val Ala Lys Pro Pro Asn Ser Thr Val Ile
                165                 170                 175

CAC ACG ACG CCT GGC AAT GCA GTG CAA GTG CGT AAC AAA ATC CCT CCA      576
His Thr Thr Pro Gly Asn Ala Val Gln Val Arg Asn Lys Ile Pro Pro
            180                 185                 190

ACC TTT CCA TGT AAG ATC AAG CCC GAA CCG AAC ACG CAG CAC CCG GAG      624
Thr Phe Pro Cys Lys Ile Lys Pro Glu Pro Asn Thr Gln His Pro Glu
            195                 200                 205

GAC AGC GAC GAG AGT CTG TCG GAC GAC GAT TCC CAG CAC CAC CGC AGC      672
Asp Ser Asp Glu Ser Leu Ser Asp Asp Asp Ser Gln His His Arg Ser
```

```
                210                 215                 220
GAG CTG ACG CGA CGG CCG TCG TAC AAT AAG ATC TTC ACC GAG ATC AGC       720
Glu Leu Thr Arg Arg Pro Ser Tyr Asn Lys Ile Phe Thr Glu Ile Ser
225                 230                 235                 240

GGT CCG GAC ATG AGC GGC GCA TCG CTT CCC ATG TCC GAC GGC GTG CTC       768
Gly Pro Asp Met Ser Gly Ala Ser Leu Pro Met Ser Asp Gly Val Leu
                245                 250                 255

AAT TCC CAG CTG GTG GGG ACC GGA GCG GGG GGC AAT GCG GCG AAC AGC       816
Asn Ser Gln Leu Val Gly Thr Gly Ala Gly Gly Asn Ala Ala Asn Ser
            260                 265                 270

TCC CTG ATG CAA TTG GAT CCC ACG TAC TAC CTG TCC AAT CGG ATG TCC       864
Ser Leu Met Gln Leu Asp Pro Thr Tyr Tyr Leu Ser Asn Arg Met Ser
        275                 280                 285

TAC AAC ACC AAC AAC AGC GGG ATA GCG GAG GAT CAG ACC CGT AAG CGC       912
Tyr Asn Thr Asn Asn Ser Gly Ile Ala Glu Asp Gln Thr Arg Lys Arg
    290                 295                 300

GAG ATC CGG CTG CAG AAG AAC AGG GAG GCG GCG CGT GAG TGC CGG CGC       960
Glu Ile Arg Leu Gln Lys Asn Arg Glu Ala Ala Arg Glu Cys Arg Arg
305                 310                 315                 320

AAG AAG AAG GAG TAC ATC AAG TGC CTG GAG AAT CGA GTG GCG GTG CTA      1008
Lys Lys Lys Glu Tyr Ile Lys Cys Leu Glu Asn Arg Val Ala Val Leu
                325                 330                 335

GAG AAC CAA AAC AAA GCG CTC ATC GAG GAG CTG AAG TCG CTC AAG GAG      1056
Glu Asn Gln Asn Lys Ala Leu Ile Glu Glu Leu Lys Ser Leu Lys Glu
            340                 345                 350

CTC TAT TGT CAG ACC AAG AAC GAT TGA                                  1083
Leu Tyr Cys Gln Thr Lys Asn Asp
        355                 360

(2) INFORMATION FOR SEQ ID NO:2:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Asn Ser Ile Val Glu Glu Asn Gly Asn Ser Ser Ala Ala Ser
1               5                   10                  15

Gly Ser Asn Asp Val Val Asp Val Val Ala Gln Gln Ala Ala Ala
            20                  25                  30

Val Gly Gly Gly Gly Gly Gly Gly Gly Gly Gly Gly Gly Gly Asn
        35                  40                  45

Pro Gln Gln Gln Gln Asn Pro Gln Ser Thr Thr Ala Gly Gly Pro
    50                  55                  60

Thr Gly Ala Thr Asn Asn Ala Gln Gly Gly Val Ser Ser Val Leu
65                  70                  75                  80

Thr Thr Thr Ala Asn Cys Asn Ile Gln Tyr Pro Ile Gln Thr Leu Ala
                85                  90                  95

Gln His Gly Leu Gln Val Ser Ile Trp Gly Pro Gly Ala Trp Cys Gln
            100                 105                 110

Leu Ser Ser Val Arg Cys Tyr Gly Ser Gln Pro Glu Val Ala Thr Lys
        115                 120                 125

Asp Val Gln Ser Val Ile Gln Ala Asn Pro Ser Gly Val Ile Gln Thr
    130                 135                 140

Ala Ala Gly Thr Gln Gln Gln Gln Ala Leu Ala Ala Ala Thr Ala
145                 150                 155                 160
```

```
Met Gln Lys Val Val Tyr Val Ala Lys Pro Pro Asn Ser Thr Val Ile
                165                 170                 175

His Thr Thr Pro Gly Asn Ala Val Gln Val Arg Asn Lys Ile Pro Pro
                180                 185                 190

Thr Phe Pro Cys Lys Ile Lys Pro Glu Pro Asn Thr Gln His Pro Glu
                195                 200                 205

Asp Ser Asp Glu Ser Leu Ser Asp Asp Ser Gln His His Arg Ser
                210                 215             220

Glu Leu Thr Arg Arg Pro Ser Tyr Asn Lys Ile Phe Thr Glu Ile Ser
225                 230                 235                 240

Gly Pro Asp Met Ser Gly Ala Ser Leu Pro Met Ser Asp Gly Val Leu
                245                 250                 255

Asn Ser Gln Leu Val Gly Thr Gly Ala Gly Gly Asn Ala Ala Asn Ser
                260                 265                 270

Ser Leu Met Gln Leu Asp Pro Thr Tyr Tyr Leu Ser Asn Arg Met Ser
                275                 280                 285

Tyr Asn Thr Asn Asn Ser Gly Ile Ala Glu Asp Gln Thr Arg Lys Arg
                290                 295                 300

Glu Ile Arg Leu Gln Lys Asn Arg Glu Ala Ala Arg Glu Cys Arg Arg
305                 310                 315                 320

Lys Lys Lys Glu Tyr Ile Lys Cys Leu Glu Asn Arg Val Ala Val Leu
                325                 330                 335

Glu Asn Gln Asn Lys Ala Leu Ile Glu Glu Leu Lys Ser Leu Lys Glu
                340                 345                 350

Leu Tyr Cys Gln Thr Lys Asn Asp
                355                 360

(2) INFORMATION FOR SEQ ID NO:3:

(i) SEQUENCE CHARACTERISTICS:
        (A) LENGTH: 54 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Arg Lys Arg Glu Ile Arg Leu Gln Lys Asn Arg Glu Ala Ala Arg Glu
1               5                   10                  15

Cys Arg Arg Lys Lys Lys Glu Tyr Ile Lys Cys Leu Glu Asn Arg Val
                20                  25                  30

Ala Val Leu Glu Asn Gln Asn Lys Ala Leu Ile Glu Glu Leu Lys Ser
                35                  40                  45

Leu Lys Glu Leu Tyr Cys
   50

(2) INFORMATION FOR SEQ ID NO:4:

(i) SEQUENCE CHARACTERISTICS:
        (A) LENGTH: 54 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Arg Lys Arg Glu Val Arg Leu Met Lys Asn Arg Glu Ala Ala Arg Glu
```

```
            1               5                   10                  15
Cys Arg Arg Lys Lys Glu Tyr Lys Cys Leu Glu Asn Arg Val
                20                  25                  30
Ala Val Leu Glu Asn Gln Asn Lys Thr Leu Ile Glu Glu Leu Lys Ala
                35                  40                  45
Leu Lys Asp Leu Tyr Cys
    50
```

(2) INFORMATION FOR SEQ ID NO:5:

(i) SEQUENCE CHARACTERISTICS:
        (A) LENGTH: 54 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Arg Lys Arg Glu Leu Arg Leu Met Lys Asn Arg Glu Ala Ala Arg Glu
1               5                   10                  15
Cys Arg Arg Lys Lys Glu Tyr Val Lys Cys Leu Glu Asn Arg Val
                20                  25                  30
Ala Val Leu Glu Asn Gln Asn Lys Thr Leu Ile Glu Glu Leu Lys Ala
                35                  40                  45
Leu Lys Asp Leu Tyr Cys
    50
```

(2) INFORMATION FOR SEQ ID NO:6:

(i) SEQUENCE CHARACTERISTICS:
        (A) LENGTH: 54 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Leu Lys Arg Glu Ile Arg Leu Met Lys Asn Arg Glu Ala Ala Arg Glu
1               5                   10                  15
Cys Arg Arg Lys Lys Glu Tyr Val Lys Cys Leu Glu Asn Arg Val
                20                  25                  30
Ala Val Leu Glu Asn Gln Asn Lys Thr Leu Ile Glu Glu Leu Lys Thr
                35                  40                  45
Leu Lys Asp Leu Tyr Ser
    50
```

(2) INFORMATION FOR SEQ ID NO:7:

(i) SEQUENCE CHARACTERISTICS:
        (A) LENGTH: 798 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..798

(xi) SEQUENCE DESCRIPTION: SEQ ID NO:7:

```
ATG TTA CTC GGA GAA AAT ATG TTT TCT ACT TTC ACA TCG TTA GAT GCT         48
```

```
Met Leu Leu Gly Glu Asn Met Phe Ser Thr Phe Thr Ser Leu Asp Ala
 1               5                  10                  15

GCT ACC GCT ACA ACC AAC ACC GGT GAA TTC TTA ATG AAT GAA TCT CCA         96
Ala Thr Ala Thr Thr Asn Thr Gly Glu Phe Leu Met Asn Glu Ser Pro
                 20                  25                  30

AGG CAA GAA GCC GGT GAC TTA ATG TTG GAT AGT CTG GAT TTC AAC ATT        144
Arg Gln Glu Ala Gly Asp Leu Met Leu Asp Ser Leu Asp Phe Asn Ile
             35                  40                  45

ATG GGC GAA AAC CTG GCA GAT GAT TTC CAG ACC TCG GCT TCA CCA GCT        192
Met Gly Glu Asn Leu Ala Asp Asp Phe Gln Thr Ser Ala Ser Pro Ala
         50                  55                  60

TCG GAG GAC AAG ATG ACT CCT TTC GTT GTT GAT ACC AAT GTT TTT GAA        240
Ser Glu Asp Lys Met Thr Pro Phe Val Val Asp Thr Asn Val Phe Glu
 65                  70                  75                  80

TCC GTC TTC AAG AAC ACC GAA GAT ACC CTT CTA GGA GAT ATC GAC AAT        288
Ser Val Phe Lys Asn Thr Glu Asp Thr Leu Leu Gly Asp Ile Asp Asn
                 85                  90                  95

GTT GGT ATT GTT GAC ACG GAG TTG AAG GAG ATG TTC GAT TTG GTT GAC        336
Val Gly Ile Val Asp Thr Glu Leu Lys Glu Met Phe Asp Leu Val Asp
            100                 105                 110

TCG GAA ATC AAT AAC GGC ACT CCT ATC AAG CAG GAA GAA AAG GAT GAT        384
Ser Glu Ile Asn Asn Gly Thr Pro Ile Lys Gln Glu Glu Lys Asp Asp
        115                 120                 125

TTG GAA TTT ACT TCA AGA TCC CAG TCC ACC TCA GCT CTC TTG TCG TCG        432
Leu Glu Phe Thr Ser Arg Ser Gln Ser Thr Ser Ala Leu Leu Ser Ser
    130                 135                 140

AAA TCG ACT TCT GCT TCT CCA GCT GAT GCT GCC GCT GCA TGT GCA AGT        480
Lys Ser Thr Ser Ala Ser Pro Ala Asp Ala Ala Ala Ala Cys Ala Ser
145                 150                 155                 160

CCT TCG TCA TCG TCT TGT AAA AGA TCC TAT TCT TCT GCT CAG CTA GAA        528
Pro Ser Ser Ser Ser Cys Lys Arg Ser Tyr Ser Ser Ala Gln Leu Glu
                165                 170                 175

ACT ACG GGT TCG GAT GCT CCA AAG AAA GAT AAG CTG GGC TGC ACC CCT        576
Thr Thr Gly Ser Asp Ala Pro Lys Lys Asp Lys Leu Gly Cys Thr Pro
            180                 185                 190

TAC ACT AGA AAA CAG AGA AAC AAT CCA TTA CCT CCG GTC ATT CCA AAG        624
Tyr Thr Arg Lys Gln Arg Asn Asn Pro Leu Pro Pro Val Ile Pro Lys
        195                 200                 205

GGT CAG GAT GTT GCT TCT ATG AAA AGG GCA AGA AAC ACT GAG GCC GCA        672
Gly Gln Asp Val Ala Ser Met Lys Arg Ala Arg Asn Thr Glu Ala Ala
    210                 215                 220

AGA AGA TCA AGA GCC AGA AAA ATG GAA AGA ATG TCC CAA CTT GAA GAA        720
Arg Arg Ser Arg Ala Arg Lys Met Glu Arg Met Ser Gln Leu Glu Glu
225                 230                 235                 240

AAG TGT CAA AGC TTG TTG AAG GAA AAC GAC GAC TTG AAA GCT CAA GTT        768
Lys Cys Gln Ser Leu Leu Lys Glu Asn Asp Asp Leu Lys Ala Gln Val
                245                 250                 255

CAA GCT TTG AAG AAA TTA CTT GGA CAA CAA                                798
Gln Ala Leu Lys Lys Leu Leu Gly Gln Gln
            260                 265

(2) INFORMATION FOR SEQ ID NO:8:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO:8:
```

-continued

```
Met Leu Leu Gly Glu Asn Met Phe Ser Thr Phe Thr Ser Leu Asp Ala
 1               5                  10                  15

Ala Thr Ala Thr Thr Asn Thr Gly Glu Phe Leu Met Asn Glu Ser Pro
             20                  25                  30

Arg Gln Glu Ala Gly Asp Leu Met Leu Asp Ser Leu Asp Phe Asn Ile
         35                  40                  45

Met Gly Glu Asn Leu Ala Asp Asp Phe Gln Thr Ser Ala Ser Pro Ala
     50                  55                  60

Ser Glu Asp Lys Met Thr Pro Phe Val Val Asp Thr Asn Val Phe Glu
 65                  70                  75                  80

Ser Val Phe Lys Asn Thr Glu Asp Thr Leu Leu Gly Asp Ile Asp Asn
                 85                  90                  95

Val Gly Ile Val Asp Thr Glu Leu Lys Glu Met Phe Asp Leu Val Asp
             100                 105                 110

Ser Glu Ile Asn Asn Gly Thr Pro Ile Lys Gln Glu Glu Lys Asp Asp
         115                 120                 125

Leu Glu Phe Thr Ser Arg Ser Gln Ser Thr Ser Ala Leu Leu Ser Ser
     130                 135                 140

Lys Ser Thr Ser Ala Ser Pro Ala Asp Ala Ala Ala Cys Ala Ser
145                 150                 155                 160

Pro Ser Ser Ser Cys Lys Arg Ser Tyr Ser Ser Ala Gln Leu Glu
                 165                 170                 175

Thr Thr Gly Ser Asp Ala Pro Lys Lys Asp Lys Leu Gly Cys Thr Pro
             180                 185                 190

Tyr Thr Arg Lys Gln Arg Asn Asn Pro Leu Pro Val Ile Pro Lys
             195                 200                 205

Gly Gln Asp Val Ala Ser Met Lys Arg Ala Arg Asn Thr Glu Ala Ala
    210                 215                 220

Arg Arg Ser Arg Ala Arg Lys Met Glu Arg Met Ser Gln Leu Glu Glu
225                 230                 235                 240

Lys Cys Gln Ser Leu Leu Lys Glu Asn Asp Asp Leu Lys Ala Gln Val
                245                 250                 255

Gln Ala Leu Lys Lys Leu Leu Gly Gln Gln
                260                 265
```

(2) INFORMATION FOR SEQ ID NO:9:

(i) SEQUENCE CHARACTERISTICS:
        (A) LENGTH: 1350 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
Met Ser Gln His Phe Thr Ser Ile Phe Glu Asn Leu Arg Phe Val Thr
 1               5                  10                  15

Ile Lys Arg Ala Thr Asn Ala Gln Gln Gln Gln Gln Gln Gln Gln Gln
             20                  25                  30

Gln Gln Leu Gln Gln Gln Gln Gln Leu Gln Gln Lys Ala Gln
         35                  40                  45

Thr Gln Gln Gln Asn Ser Arg Lys Ile Lys Thr Gln Ala Thr Pro Thr
     50                  55                  60

Leu Asn Gly Asn Gly Leu Leu Ser Gly Asn Pro Asn Gly Gly Gly Gly
 65                  70                  75                  80
```

-continued

```
Asp Ser Ser Pro Ser His Glu Val Asp His Pro Gly Gly Ala Gln Gly
                 85                  90                  95
Ala Gln Ala Ala Gly Gly Leu Pro Ser Leu Ser Gly Thr Pro Leu Arg
            100                 105                 110
His His Lys Arg Ala Ser Ile Ser Thr Ala Ser Pro Pro Ile Arg Glu
        115                 120                 125
Arg Arg Gly Thr Asn Thr Ser Ile Val Val Glu Leu Asp Gly Ser Gly
    130                 135                 140
Ser Gly Ser Gly Ser Gly Gly Gly Val Gly Val Gly Gln Gly Ala
145                 150                 155                 160
Gly Cys Pro Pro Ser Gly Ser Cys Thr Ala Ser Gly Lys Ser Ser Arg
                165                 170                 175
Glu Leu Ser Pro Ser Pro Lys Asn Gln Gln Pro Arg Lys Met Ser
            180                 185                 190
Gln Asp Tyr Arg Ser Arg Ala Gly Ser Phe Met His Leu Asp Asp Glu
        195                 200                 205
Gly Arg Ser Leu Leu Met Arg Lys Pro Met Arg Leu Lys Asn Ile Glu
    210                 215                 220
Gly Arg Pro Glu Val Tyr Asp Thr Leu His Cys Lys Gly Arg Glu Ile
225                 230                 235                 240
Leu Ser Cys Ser Lys Ala Thr Cys Thr Ser Ser Ile Met Asn Ile Gly
                245                 250                 255
Asn Ala Ala Val Glu Ala Arg Lys Ser Asp Leu Ile Leu Glu His Ala
            260                 265                 270
Lys Asp Phe Leu Glu Gln Tyr Phe Thr Ser Ile Lys Arg Thr Ser Cys
        275                 280                 285
Thr Ala His Glu Thr Arg Trp Lys Gln Val Arg Gln Ser Ile Glu Thr
    290                 295                 300
Thr Gly His Tyr Gln Leu Thr Glu Thr Glu Leu Ile Tyr Gly Ala Lys
305                 310                 315                 320
Leu Ala Trp Arg Asn Ser Ser Arg Cys Ile Gly Arg Ile Gln Trp Ser
                325                 330                 335
Lys Leu Gln Val Phe Asp Cys Arg Tyr Val Thr Thr Thr Ser Gly Met
            340                 345                 350
Phe Glu Ala Ile Cys Asn His Ile Lys Tyr Ala Thr Asn Lys Gly Asn
        355                 360                 365
Leu Arg Ser Ala Ile Thr Ile Phe Pro Gln Arg Thr Asp Ala Lys His
    370                 375                 380
Asp Tyr Arg Ile Trp Asn Asn Gln Leu Ile Ser Tyr Ala Gly Tyr Lys
385                 390                 395                 400
Gln Ala Asp Gly Lys Ile Ile Gly Asp Pro Met Asn Val Glu Phe Thr
                405                 410                 415
Glu Val Cys Thr Lys Leu Gly Trp Lys Ser Lys Gly Ser Glu Trp Asp
            420                 425                 430
Ile Leu Pro Leu Val Val Ser Ala Asn Gly His Asp Pro Asp Tyr Phe
        435                 440                 445
Asp Tyr Pro Pro Glu Leu Ile Leu Glu Val Pro Leu Thr His Pro Lys
    450                 455                 460
Phe Glu Trp Phe Ser Asp Leu Gly Leu Arg Trp Tyr Ala Leu Pro Ala
465                 470                 475                 480
Val Ser Ser Met Leu Phe Asp Val Gly Gly Ile Gln Phe Thr Ala Thr
                485                 490                 495
Thr Phe Ser Gly Trp Tyr Met Ser Thr Glu Ile Gly Ser Arg Asn Leu
```

```
                500             505             510
Cys Asp Thr Asn Arg Arg Asn Met Leu Glu Thr Val Ala Leu Lys Met
            515             520             525

Gln Leu Asp Thr Arg Thr Pro Thr Ser Leu Trp Lys Asp Lys Ala Val
530             535             540

Val Glu Met Asn Ile Ala Val Leu His Ser Tyr Gln Ser Arg Asn Val
545             550             555             560

Thr Ile Val Asp His His Thr Ala Ser Glu Ser Phe Met Lys His Phe
            565             570             575

Glu Asn Glu Ser Lys Leu Arg Asn Gly Cys Pro Ala Asp Trp Ile Trp
            580             585             590

Ile Val Pro Pro Leu Ser Gly Ser Ile Thr Pro Val Phe His Gln Glu
            595             600             605

Met Ala Leu Tyr Tyr Leu Lys Pro Ser Phe Glu Tyr Gln Asp Pro Ala
            610             615             620

Trp Arg Thr His Val Trp Lys Lys Gly Arg Gly Glu Ser Lys Gly Lys
625             630             635             640

Lys Pro Arg Arg Lys Phe Asn Phe Lys Gln Ile Ala Arg Ala Val Lys
            645             650             655

Phe Thr Ser Lys Leu Phe Gly Arg Ala Leu Ser Lys Arg Ile Lys Ala
            660             665             670

Thr Val Leu Tyr Ala Thr Glu Thr Gly Lys Ser Glu Gln Tyr Ala Lys
            675             680             685

Gln Leu Cys Glu Leu Leu Gly His Ala Phe Asn Ala Gln Ile Tyr Cys
            690             695             700

Met Ser Asp Tyr Asp Ile Ser Ser Ile Glu His Glu Ala Leu Leu Ile
705             710             715             720

Val Val Ala Ser Thr Phe Gly Asn Gly Asp Pro Pro Glu Asn Gly Glu
            725             730             735

Leu Phe Ser Gln Glu Leu Tyr Ala Met Arg Val Gln Glu Ser Ser Glu
            740             745             750

His Gly Leu Gln Asp Ser Ser Ile Gly Ser Ser Lys Ser Phe Met Lys
            755             760             765

Ala Ser Ser Arg Gln Glu Phe Met Lys Leu Pro Leu Gln Gln Val Lys
            770             775             780

Arg Ile Asp Arg Trp Asp Ser Leu Arg Gly Ser Thr Ser Asp Thr Phe
785             790             795             800

Thr Glu Glu Thr Phe Gly Pro Leu Ser Asn Val Arg Phe Ala Val Phe
            805             810             815

Ala Leu Gly Ser Ser Ala Tyr Pro Asn Phe Cys Ala Phe Gly Gln Tyr
            820             825             830

Val Asp Asn Ile Leu Gly Glu Leu Gly Gly Glu Arg Leu Leu Arg Val
            835             840             845

Ala Tyr Gly Asp Glu Met Cys Gly Gln Glu Gln Ser Phe Arg Lys Trp
850             855             860

Ala Pro Glu Val Phe Lys Leu Ala Cys Glu Thr Phe Cys Leu Asp Pro
865             870             875             880

Glu Glu Ser Leu Ser Asp Ala Ser Leu Ala Leu Gln Asn Asp Ser Leu
            885             890             895

Thr Val Asn Thr Val Arg Leu Val Pro Ser Ala Asn Lys Gly Ser Leu
            900             905             910

Asp Ser Ser Leu Ser Lys Tyr His Asn Lys Lys Val His Cys Cys Lys
            915             920             925
```

-continued

```
Ala Lys Ala Lys Pro His Asn Leu Thr Arg Leu Ser Glu Gly Ala Lys
    930                 935                 940

Thr Thr Met Leu Leu Glu Ile Cys Ala Pro Gly Leu Glu Tyr Glu Pro
945                 950                 955                 960

Gly Asp His Val Gly Ile Phe Pro Ala Asn Arg Thr Glu Leu Val Asp
                965                 970                 975

Gly Leu Leu Asn Arg Leu Val Gly Val Asp Asn Pro Asp Glu Val Leu
            980                 985                 990

Gln Leu Gln Leu Lys Glu Lys Gln Thr Ser Asn Gly Ile Phe Lys
    995                 1000                1005

Cys Trp Glu Pro His Asp Lys Ile Pro Pro Asp Thr Leu Arg Asn Leu
    1010                1015                1020

Leu Ala Arg Phe Phe Asp Leu Thr Thr Pro Pro Ser Arg Gln Leu Leu
1025                1030                1035                1040

Thr Leu Leu Ala Gly Phe Cys Glu Asp Thr Ala Asp Lys Glu Arg Leu
                1045                1050                1055

Glu Leu Leu Val Asn Asp Ser Ser Ala Tyr Glu Asp Trp Arg His Trp
            1060                1065                1070

Arg Leu Pro His Leu Leu Asp Val Leu Glu Glu Phe Pro Ser Cys Arg
        1075                1080                1085

Pro Pro Ala Pro Leu Leu Leu Ala Gln Leu Thr Pro Leu Gln Pro Arg
    1090                1095                1100

Phe Tyr Ser Ile Ser Ser Ser Pro Arg Arg Val Ser Asp Glu Ile His
1105                1110                1115                1120

Leu Thr Val Ala Ile Val Lys Tyr Arg Cys Glu Asp Gly Gln Gly Asp
                1125                1130                1135

Glu Arg Tyr Gly Val Cys Ser Asn Tyr Leu Ser Gly Leu Arg Ala Asp
            1140                1145                1150

Asp Glu Leu Phe Met Phe Val Arg Ser Ala Leu Gly Phe His Leu Pro
        1155                1160                1165

Ser Asp Arg Ser Arg Pro Ile Ile Leu Ile Gly Pro Gly Thr Gly Ile
    1170                1175                1180

Ala Pro Phe Arg Ser Phe Trp Gln Glu Phe Gln Val Leu Arg Asp Leu
1185                1190                1195                1200

Asp Pro Thr Ala Lys Leu Pro Lys Met Trp Leu Phe Gly Cys Arg
                1205                1210                1215

Asn Arg Asp Val Asp Leu Tyr Ala Glu Glu Lys Ala Glu Leu Gln Lys
            1220                1225                1230

Asp Gln Ile Leu Asp Arg Val Phe Leu Ala Leu Ser Arg Glu Gln Ala
        1235                1240                1245

Ile Pro Lys Thr Tyr Val Gln Asp Leu Ile Glu Gln Glu Phe Asp Ser
    1250                1255                1260

Leu Tyr Gln Leu Ile Val Gln Glu Arg Gly His Ile Tyr Val Cys Gly
1265                1270                1275                1280

Asp Val Thr Met Ala Glu His Val Tyr Gln Thr Ile Arg Lys Cys Ile
                1285                1290                1295

Ala Gly Lys Glu Gln Lys Ser Glu Ala Glu Val Glu Thr Phe Leu Leu
            1300                1305                1310

Thr Leu Arg Asp Glu Ser Arg Tyr His Glu Asp Ile Phe Gly Ile Thr
        1315                1320                1325

Leu Arg Thr Ala Glu Ile His Thr Lys Ser Arg Ala Thr Ala Arg Ile
    1330                1335                1340
```

```
Arg Met Ala Ser Gln Pro
1345            1350
```

(2) INFORMATION FOR SEQ ID NO:10:

(i) SEQUENCE CHARACTERISTICS:
        (A) LENGTH: 1205 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Met Gly Asn Leu Lys Ser Val Gly Gln Glu Pro Gly Pro Pro Cys Gly
1               5                   10                  15

Leu Gly Leu Gly Leu Gly Leu Gly Leu Cys Gly Lys Gln Gly Pro Ala
            20                  25                  30

Ser Pro Ala Pro Glu Pro Ser Arg Ala Pro Ala Pro Thr Pro His
        35                  40                  45

Ala Pro Asp His Ser Pro Ala Pro Asn Ser Pro Thr Leu Thr Arg Pro
        50                  55                  60

Pro Glu Gly Pro Lys Phe Pro Arg Val Lys Asn Trp Glu Leu Gly Ser
65                  70                  75                  80

Ile Thr Tyr Asp Thr Leu Cys Ala Gln Ser Gln Gln Asp Gly Pro Cys
                85                  90                  95

Thr Pro Arg Arg Cys Leu Gly Ser Leu Val Leu Pro Arg Lys Leu Gln
            100                 105                 110

Thr Arg Pro Ser Pro Gly Pro Pro Ala Glu Gln Leu Leu Ser Gln
            115                 120                 125

Ala Arg Asp Phe Ile Asn Gln Tyr Tyr Ser Ser Ile Lys Arg Ser Gly
        130                 135                 140

Ser Gln Ala His Glu Glu Arg Leu Gln Glu Val Glu Ala Glu Val Ala
145                 150                 155                 160

Ser Thr Gly Thr Ile His Leu Arg Glu Ser Glu Leu Val Phe Gly Ala
                165                 170                 175

Lys Gln Ala Trp Arg Asn Ala Pro Arg Cys Val Gly Arg Ile Gln Trp
            180                 185                 190

Gly Lys Leu Gln Val Phe Asp Ala Arg Asp Cys Ser Ser Ala Gln Glu
        195                 200                 205

Met Phe Thr Tyr Ile Cys Asn His Ile Lys Tyr Ala Thr Asn Arg Gly
        210                 215                 220

Asn Leu Arg Ser Ala Ile Thr Val Phe Pro Gln Arg Ala Pro Gly Arg
225                 230                 235                 240

Gly Asp Phe Arg Ile Trp Asn Ser Gln Leu Val Arg Tyr Ala Gly Tyr
                245                 250                 255

Arg Gln Gln Asp Gly Ser Val Arg Gly Asp Pro Ala Asn Val Glu Ile
            260                 265                 270

Thr Glu Leu Cys Ile Gln His Gly Trp Thr Pro Gly Asn Gly Arg Phe
        275                 280                 285

Asp Val Leu Pro Leu Leu Leu Gln Ala Pro Asp Glu Ala Pro Glu Leu
        290                 295                 300

Phe Val Leu Pro Pro Glu Leu Val Leu Glu Val Pro Leu Gly Ala Pro
305                 310                 315                 320

His Thr Gly Val Val Arg Gly Pro Gly Leu Arg Trp Tyr Ala Leu Pro
                325                 330                 335
```

-continued

```
Ala Val Ser Asn Met Leu Leu Glu Ile Gly Gly Leu Glu Phe Ser Ala
            340                 345                 350
Ala Pro Phe Ser Gly Trp Tyr Met Ser Thr Glu Ile Gly Thr Arg Asn
            355                 360             365
Leu Cys Asp Pro His Arg Tyr Asn Ile Leu Glu Asp Val Ala Val Cys
            370             375                 380
Met Asp Leu Asp Thr Arg Thr Thr Ser Ser Leu Trp Lys Asp Lys Ala
385                 390                 395                 400
Ala Val Glu Ile Asn Leu Ala Val Leu His Ser Phe Gln Leu Ala Lys
                405                 410                 415
Val Thr Ile Val Asp His His Ala Ala Thr Val Ser Phe Met Lys His
                420                 425             430
Leu Asp Asn Glu Gln Lys Ala Arg Gly Gly Cys Pro Ala Asp Trp Ala
            435                 440             445
Trp Ile Val Pro Pro Ile Tyr Gly Ser Leu Pro Pro Val Phe His Gln
        450                 455                 460
Glu Met Val Asn Tyr Ile Leu Ser Pro Ala Phe Arg Tyr Gln Pro Asp
465                 470                 475                 480
Pro Trp Lys Gly Ser Ala Thr Lys Gly Ala Gly Ile Thr Arg Lys Lys
                485                 490                 495
Thr Phe Lys Glu Val Ala Asn Ala Val Lys Ile Ser Ala Ser Leu Met
            500                 505             510
Gly Thr Leu Met Ala Lys Arg Val Lys Ala Thr Ile Leu Tyr Ala Ser
        515                 520             525
Glu Thr Gly Arg Ala Gln Ser Tyr Ala Gln Gln Leu Gly Arg Leu Phe
        530                 535             540
Arg Lys Ala Phe Asp Pro Arg Val Leu Cys Met Asp Glu Tyr Asp Val
545                 550                 555                 560
Val Ser Leu Glu His Glu Ala Leu Val Leu Val Val Thr Ser Thr Phe
                565                 570                 575
Gly Asn Gly Asp Pro Pro Glu Asn Gly Glu Ser Phe Ala Ala Ala Leu
            580                 585                 590
Met Glu Met Ser Gly Pro Tyr Asn Ser Ser Pro Arg Pro Glu Gln His
            595                 600             605
Lys Ser Tyr Lys Ile Arg Phe Asn Ser Val Ser Cys Ser Asp Pro Leu
        610                 615             620
Val Ser Ser Trp Arg Arg Lys Arg Lys Glu Ser Ser Asn Thr Asp Ser
625                 630                 635                 640
Ala Gly Ala Leu Gly Thr Leu Arg Phe Cys Val Phe Gly Leu Gly Ser
                645                 650                 655
Arg Ala Tyr Pro His Phe Cys Ala Phe Ala Arg Ala Val Asp Thr Arg
                660                 665                 670
Leu Glu Glu Leu Gly Gly Glu Arg Leu Leu Gln Leu Gly Gln Gly Asp
            675                 680                 685
Glu Leu Cys Gly Gln Glu Glu Ala Phe Arg Gly Trp Ala Lys Ala Ala
        690                 695                 700
Phe Gln Ala Ser Cys Glu Thr Phe Cys Val Gly Glu Ala Lys Ala
705                 710                 715                 720
Ala Ala Gln Asp Ile Phe Ser Pro Lys Arg Ser Trp Lys Arg Gln Arg
                725                 730                 735
Tyr Arg Leu Ser Ala Gln Ala Glu Gly Leu Gln Leu Leu Pro Gly Leu
            740                 745                 750
Ile His Val His Arg Arg Lys Met Phe Gln Ala Thr Val Leu Ser Val
```

-continued

```
            755                 760                 765
Glu Asn Leu Gln Ser Ser Lys Ser Thr Arg Ala Thr Ile Leu Val Arg
    770                 775                 780

Leu Asp Thr Ala Gly Gln Glu Gly Leu Gln Tyr Gln Pro Gly Asp His
785                 790                 795                 800

Ile Gly Ile Ser Ala Pro Asn Arg Pro Gly Leu Val Glu Ala Leu Leu
                    805                 810                 815

Ser Arg Val Glu Asp Pro Pro Pro Thr Glu Ser Val Ala Val Glu
            820                 825                 830

Gln Leu Glu Lys Gly Ser Pro Gly Gly Pro Pro Ser Trp Val Arg
            835                 840                 845

Asp Pro Arg Leu Pro Pro Cys Thr Val Arg Gln Ala Leu Thr Phe Phe
850                 855                 860

Leu Asp Ile Thr Ser Pro Pro Ser Pro Arg Leu Leu Arg Leu Leu Ser
865                 870                 875                 880

Thr Leu Ala Glu Glu Pro Ser Glu Gln Gln Glu Leu Glu Thr Leu Ser
                    885                 890                 895

Gln Asp Pro Arg Arg Tyr Glu Glu Trp Lys Leu Val Arg Cys Pro Thr
            900                 905                 910

Leu Leu Glu Val Leu Glu Gln Phe Pro Ser Val Ala Leu Pro Ala Pro
            915                 920                 925

Leu Leu Leu Thr Gln Leu Pro Leu Leu Gln Pro Arg Tyr Tyr Ser Val
            930                 935                 940

Ser Ser Ala Pro Asn Ala His Pro Gly Glu Val His Leu Thr Val Ala
945                 950                 955                 960

Val Leu Ala Tyr Arg Thr Gln Asp Gly Leu Gly Pro Leu His Tyr Gly
                    965                 970                 975

Val Cys Ser Thr Trp Leu Ser Gln Leu Lys Thr Gly Asp Pro Val Pro
                    980                 985                 990

Cys Phe Ile Arg Gly Ala Pro Ser Phe Arg Leu Pro Pro Asp Pro Tyr
            995                 1000                1005

Val Pro Cys Ile Leu Val Gly Pro Gly Thr Gly Ile Ala Pro Phe Arg
            1010                1015                1020

Gly Phe Trp Gln Glu Arg Leu His Asp Ile Glu Ser Lys Gly Leu Gln
1025                1030                1035                1040

Pro His Pro Met Thr Leu Val Phe Gly Cys Arg Cys Ser Gln Leu Asp
                    1045                1050                1055

His Leu Tyr Arg Asp Glu Val Gln Asp Ala Gln Glu Arg Gly Val Phe
                    1060                1065                1070

Gly Arg Val Leu Thr Ala Phe Ser Arg Glu Pro Asp Ser Pro Lys Thr
            1075                1080                1085

Tyr Val Gln Asp Ile Leu Arg Thr Glu Leu Ala Ala Glu Val His Arg
            1090                1095                1100

Val Leu Cys Leu Glu Arg Gly His Met Phe Val Cys Gly Asp Val Thr
1105                1110                1115                1120

Met Ala Thr Ser Val Leu Gln Thr Val Gln Arg Ile Leu Ala Thr Glu
                    1125                1130                1135

Gly Asp Met Glu Leu Asp Glu Ala Gly Asp Val Ile Gly Val Leu Arg
            1140                1145                1150

Asp Gln Gln Arg Tyr His Glu Asp Ile Phe Gly Leu Thr Leu Arg Thr
            1155                1160                1165

Gln Glu Val Thr Ser Arg Ile Arg Thr Gln Ser Phe Ser Leu Gln Glu
            1170                1175                1180
```

-continued

Arg His Leu Arg Gly Ala Val Pro Trp Ala Phe Asp Pro Pro Gly Pro
1185                1190                1195                1200

Asp Thr Pro Gly Pro
              1205

(2) INFORMATION FOR SEQ ID NO:11:

(i) SEQUENCE CHARACTERISTICS:
        (A) LENGTH: 1429 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

Met Glu Glu Asn Thr Phe Gly Val Gln Gln Ile Gln Pro Asn Val Ile
1               5                   10                  15

Ser Val Arg Leu Phe Lys Arg Val Gly Leu Gly Phe Leu Val
                20                  25                  30

Lys Glu Arg Val Ser Lys Pro Val Ile Ile Ser Asp Leu Ile Arg
                35                  40                  45

Gly Gly Ala Ala Glu Gln Ser Gly Leu Ile Gln Ala Gly Asp Ile Ile
50                  55                  60

Leu Ala Val Asn Asp Arg Pro Leu Val Asp Leu Ser Tyr Asp Ser Ala
65                  70                  75                  80

Leu Glu Val Leu Arg Gly Ile Ala Ser Glu Thr His Val Val Leu Ile
                85                  90                  95

Leu Arg Gly Pro Glu Gly Phe Thr Thr His Leu Glu Thr Thr Phe Thr
                100                 105                 110

Gly Asp Gly Thr Pro Lys Thr Ile Arg Val Thr Gln Pro Leu Gly Pro
                115                 120                 125

Pro Thr Lys Ala Val Asp Leu Ser His Gln Pro Ser Ala Ser Lys Asp
130                 135                 140

Gln Ser Leu Ala Val Asp Arg Val Thr Gly Leu Gly Asn Gly Pro Gln
145                 150                 155                 160

His Ala Gln Gly His Gly Gln Gly Ala Gly Ser Val Ser Gln Ala Asn
                165                 170                 175

Gly Val Ala Ile Asp Pro Thr Met Lys Ser Thr Lys Ala Asn Leu Gln
                180                 185                 190

Asp Ile Gly Glu His Asp Glu Leu Leu Lys Glu Ile Glu Pro Val Leu
                195                 200                 205

Ser Ile Leu Asn Ser Gly Ser Lys Ala Thr Asn Arg Gly Gly Pro Ala
                210                 215                 220

Lys Ala Glu Met Lys Asp Thr Gly Ile Gln Val Asp Arg Asp Leu Asp
225                 230                 235                 240

Gly Lys Ser His Lys Ala Pro Pro Leu Gly Gly Asp Asn Asp Arg Val
                245                 250                 255

Phe Asn Asp Leu Trp Gly Lys Asp Asn Val Pro Val Ile Leu Asn Asn
                260                 265                 270

Pro Tyr Ser Glu Lys Glu Gln Ser Pro Thr Ser Gly Lys Gln Ser Pro
                275                 280                 285

Thr Lys Asn Gly Ser Pro Ser Arg Cys Pro Arg Phe Leu Lys Val Lys
                290                 295                 300

Asn Trp Glu Thr Asp Val Val Leu Thr Asp Thr Leu His Leu Lys Ser
305                 310                 315                 320

-continued

```
Thr Leu Glu Thr Gly Cys Thr Glu His Ile Cys Met Gly Ser Ile Met
                325                 330                 335
Leu Pro Ser Gln His Thr Arg Lys Pro Glu Asp Val Arg Thr Lys Asp
            340                 345                 350
Gln Leu Phe Pro Leu Ala Lys Glu Phe Leu Asp Gln Tyr Tyr Ser Ser
        355                 360                 365
Ile Lys Arg Phe Gly Ser Lys Ala His Met Asp Arg Leu Glu Glu Val
    370                 375                 380
Asn Lys Glu Ile Glu Ser Thr Ser Thr Tyr Gln Leu Lys Asp Thr Glu
385                 390                 395                 400
Leu Ile Tyr Gly Ala Lys His Ala Trp Arg Asn Ala Ser Arg Cys Val
                405                 410                 415
Gly Arg Ile Gln Trp Ser Lys Leu Gln Val Phe Asp Ala Arg Asp Cys
            420                 425                 430
Thr Thr Ala His Gly Met Phe Asn Tyr Ile Cys Asn His Val Lys Tyr
        435                 440                 445
Ala Thr Asn Lys Gly Asn Leu Arg Ser Ala Ile Thr Ile Phe Pro Gln
    450                 455                 460
Arg Thr Asp Gly Lys His Asp Phe Arg Val Trp Asn Ser Gln Leu Ile
465                 470                 475                 480
Arg Tyr Ala Gly Tyr Lys Gln Pro Asp Gly Ser Thr Leu Gly Asp Pro
                485                 490                 495
Ala Asn Val Gln Phe Thr Glu Ile Cys Ile Gln Gln Gly Trp Lys Ala
            500                 505                 510
Pro Arg Gly Arg Phe Asp Val Leu Pro Leu Leu Leu Gln Ala Asn Gly
        515                 520                 525
Asn Asp Pro Glu Leu Phe Gln Ile Pro Pro Glu Leu Val Leu Glu Val
    530                 535                 540
Pro Ile Arg His Pro Lys Phe Asp Trp Phe Lys Asp Leu Gly Leu Lys
545                 550                 555                 560
Trp Tyr Gly Leu Pro Ala Val Ser Asn Met Leu Leu Glu Ile Gly Gly
                565                 570                 575
Leu Glu Phe Ser Ala Cys Pro Phe Ser Gly Trp Tyr Met Gly Thr Glu
            580                 585                 590
Ile Gly Val Arg Asp Tyr Cys Asp Asn Ser Arg Tyr Asn Ile Leu Glu
        595                 600                 605
Glu Val Ala Lys Lys Met Asp Leu Asp Met Arg Lys Thr Ser Ser Leu
    610                 615                 620
Trp Lys Asp Gln Ala Leu Val Glu Ile Asn Ile Ala Val Leu Tyr Ser
625                 630                 635                 640
Phe Gln Ser Asp Lys Val Thr Ile Val Asp His His Ser Ala Thr Glu
                645                 650                 655
Ser Phe Ile Lys His Met Glu Asn Glu Tyr Arg Cys Arg Gly Gly Cys
            660                 665                 670
Pro Ala Asp Trp Val Trp Ile Val Pro Pro Met Ser Gly Ser Ile Thr
        675                 680                 685
Pro Val Phe His Gln Glu Met Leu Asn Tyr Arg Leu Thr Pro Ser Phe
    690                 695                 700
Glu Tyr Gln Pro Asp Pro Trp Asn Thr His Val Trp Lys Gly Thr Asn
705                 710                 715                 720
Gly Thr Pro Thr Lys Arg Arg Ala Ile Gly Phe Lys Lys Leu Ala Glu
                725                 730                 735
```

-continued

```
Ala Val Lys Phe Ser Ala Lys Leu Met Gly Gln Ala Met Ala Lys Arg
            740                 745                 750

Val Lys Ala Thr Ile Leu Tyr Ala Thr Glu Thr Gly Lys Ser Gln Ala
            755                 760                 765

Tyr Ala Lys Thr Leu Cys Glu Ile Phe Lys His Ala Phe Asp Ala Lys
            770                 775                 780

Ala Met Ser Met Glu Glu Tyr Asp Ile Val His Leu Glu His Glu Ala
785                 790                 795                 800

Leu Val Leu Val Val Thr Ser Thr Phe Gly Asn Gly Asp Pro Pro Glu
                805                 810                 815

Asn Gly Glu Lys Phe Gly Cys Ala Leu Met Glu Met Arg His Pro Asn
                820                 825                 830

Ser Val Gln Glu Glu Arg Lys Ser Tyr Lys Val Arg Phe Asn Ser Val
                835                 840                 845

Ser Ser Tyr Ser Asp Ser Arg Lys Ser Ser Gly Asp Gly Pro Asp Leu
                850                 855                 860

Arg Asp Asn Phe Glu Ser Thr Gly Pro Leu Ala Asn Val Arg Phe Ser
865                 870                 875                 880

Val Phe Gly Leu Gly Ser Arg Ala Tyr Pro His Phe Cys Ala Phe Gly
                885                 890                 895

His Ala Val Asp Thr Leu Leu Glu Glu Leu Gly Gly Glu Arg Ile Leu
                900                 905                 910

Lys Met Arg Glu Gly Asp Glu Leu Cys Gly Gln Glu Glu Ala Phe Arg
                915                 920                 925

Thr Trp Ala Lys Lys Val Phe Lys Ala Ala Cys Asp Val Phe Cys Val
                930                 935                 940

Gly Asp Asp Val Asn Ile Glu Lys Pro Asn Asn Ser Leu Ile Ser Asn
945                 950                 955                 960

Asp Arg Ser Trp Lys Arg Asn Lys Phe Arg Leu Thr Tyr Val Ala Glu
                965                 970                 975

Ala Pro Asp Leu Thr Gln Gly Leu Ser Asn Val His Lys Lys Arg Val
                980                 985                 990

Ser Ala Ala Arg Leu Leu Ser Arg Gln Asn Leu Gln Ser Pro Lys Phe
                995                 1000                1005

Ser Arg Ser Thr Ile Phe Val Arg Leu His Thr Asn Gly Asn Gln Glu
            1010                1015                1020

Leu Gln Tyr Gln Pro Gly Asp His Leu Gly Val Phe Pro Gly Asn His
1025                1030                1035                1040

Glu Asp Leu Val Asn Ala Leu Ile Glu Arg Leu Glu Asp Ala Pro Pro
                1045                1050                1055

Ala Asn His Val Val Lys Val Glu Met Leu Glu Glu Arg Asn Thr Ala
                1060                1065                1070

Leu Gly Val Ile Ser Asn Trp Lys Asp Glu Ser Arg Leu Pro Pro Cys
                1075                1080                1085

Thr Ile Phe Gln Ala Phe Lys Tyr Tyr Leu Asp Ile Thr Thr Pro Pro
                1090                1095                1100

Thr Pro Leu Gln Leu Gln Gln Phe Ala Ser Leu Ala Thr Asn Glu Lys
1105                1110                1115                1120

Glu Lys Gln Arg Leu Leu Val Leu Ser Lys Gly Leu Gln Glu Tyr Glu
                1125                1130                1135

Glu Trp Lys Trp Gly Lys Asn Pro Thr Met Val Glu Val Leu Glu Glu
                1140                1145                1150

Phe Pro Ser Ile Gln Met Pro Ala Thr Leu Leu Leu Thr Gln Leu Ser
```

-continued

```
                  1155                1160                     1165
Leu Leu Gln Pro Arg Tyr Tyr Ser Ile Ser Ser Ser Pro Asp Met Tyr
    1170                1175                1180

Pro Asp Glu Val His Leu Thr Val Ala Ile Val Ser Tyr His Thr Arg
1185                1190                1195                1200

Asp Gly Glu Gly Pro Val His His Gly Val Cys Ser Ser Trp Leu Asn
                1205                1210                1215

Arg Ile Gln Ala Asp Asp Val Val Pro Cys Phe Val Arg Gly Ala Pro
                1220                1225                1230

Ser Phe His Leu Pro Arg Asn Pro Gln Val Pro Cys Ile Leu Val Gly
            1235                1240                1245

Pro Gly Thr Gly Ile Ala Pro Phe Arg Ser Phe Trp Gln Gln Arg Gln
    1250                1255                1260

Phe Asp Ile Gln His Lys Gly Met Asn Pro Cys Pro Met Val Leu Val
1265                1270                1275                1280

Phe Gly Cys Arg Gln Ser Lys Ile Asp His Ile Tyr Arg Glu Glu Thr
                1285                1290                1295

Leu Gln Ala Lys Asn Lys Gly Val Phe Arg Glu Leu Tyr Thr Ala Tyr
                1300                1305                1310

Ser Arg Glu Pro Asp Arg Pro Lys Lys Tyr Val Gln Asp Val Leu Gln
            1315                1320                1325

Glu Gln Leu Ala Glu Ser Val Tyr Arg Ala Leu Lys Glu Gln Gly Gly
    1330                1335                1340

His Ile Tyr Val Cys Gly Asp Val Thr Met Ala Ala Asp Val Leu Lys
1345                1350                1355                1360

Ala Ile Gln Arg Ile Met Thr Gln Gln Gly Lys Leu Ser Glu Glu Asp
                1365                1370                1375

Ala Gly Val Phe Ile Ser Arg Leu Arg Asp Asp Asn Arg Tyr His Glu
                1380                1385                1390

Asp Ile Phe Gly Val Thr Leu Arg Thr Tyr Glu Val Thr Asn Arg Leu
            1395                1400                1405

Arg Ser Glu Ser Ile Ala Phe Ile Glu Glu Ser Lys Lys Asp Ala Asp
    1410                1415                1420

Glu Val Phe Ser Ser
1425
```

(2) INFORMATION FOR SEQ ID NO:12:

(i) SEQUENCE CHARACTERISTICS:
        (A) LENGTH: 1144 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Met Ala Cys Pro Trp Lys Phe Leu Phe Lys Val Lys Ser Tyr Gln Ser
1               5                   10                  15

Asp Leu Lys Glu Glu Lys Asp Ile Asn Asn Asn Val Lys Lys Thr Pro
            20                  25                  30

Cys Ala Val Leu Ser Pro Thr Ile Gln Asp Asp Pro Lys Ser His Gln
        35                  40                  45

Asn Gly Ser Pro Gln Leu Leu Thr Gly Thr Ala Gln Asn Val Pro Glu
    50                  55                  60

Ser Leu Asp Lys Leu His Val Thr Ser Thr Arg Pro Gln Tyr Val Arg
```

```
65                  70                  75                  80
Ile Lys Asn Trp Gly Ser Gly Glu Ile Leu His Asp Thr Leu His His
                85                  90                  95

Lys Ala Thr Ser Asp Phe Thr Cys Lys Ser Lys Ser Cys Leu Gly Ser
                100                 105                 110

Ile Met Asn Pro Lys Ser Leu Thr Arg Gly Pro Arg Asp Lys Pro Thr
                115                 120                 125

Pro Leu Glu Glu Leu Leu Pro His Ala Ile Glu Phe Ile Asn Gln Tyr
            130                 135                 140

Tyr Gly Ser Phe Lys Glu Ala Lys Ile Glu Glu His Leu Ala Arg Leu
145                 150                 155                 160

Glu Ala Val Thr Lys Glu Ile Glu Thr Thr Gly Thr Tyr Gln Leu Thr
                165                 170                 175

Leu Asp Glu Leu Ile Phe Ala Thr Lys Met Ala Trp Arg Asn Ala Pro
            180                 185                 190

Arg Cys Ile Gly Arg Ile Gln Trp Ser Asn Leu Gln Val Phe Asp Ala
            195                 200                 205

Arg Asn Cys Ser Thr Ala Gln Glu Met Phe Gln His Ile Cys Arg His
            210                 215                 220

Ile Leu Tyr Ala Thr Asn Asn Gly Asn Ile Arg Ser Ala Ile Thr Val
225                 230                 235                 240

Phe Pro Gln Arg Ser Asp Gly Lys His Asp Phe Arg Leu Trp Asn Ser
                245                 250                 255

Gln Leu Ile Arg Tyr Ala Gly Tyr Gln Met Pro Asp Gly Thr Ile Arg
                260                 265                 270

Gly Asp Ala Ala Thr Leu Glu Phe Thr Gln Leu Cys Ile Asp Leu Gly
            275                 280                 285

Trp Lys Pro Arg Tyr Gly Arg Phe Asp Val Leu Pro Leu Val Leu Gln
            290                 295                 300

Ala Asp Gly Gln Asp Pro Glu Val Phe Glu Ile Pro Pro Asp Leu Val
305                 310                 315                 320

Leu Glu Val Thr Met Glu His Pro Lys Tyr Glu Trp Phe Gln Glu Leu
                325                 330                 335

Gly Leu Lys Trp Tyr Ala Leu Pro Ala Val Ala Asn Met Leu Leu Glu
                340                 345                 350

Val Gly Gly Leu Glu Phe Pro Ala Cys Pro Phe Asn Gly Trp Tyr Met
            355                 360                 365

Gly Thr Glu Ile Gly Val Arg Asp Phe Cys Asp Thr Gln Arg Tyr Asn
            370                 375                 380

Ile Leu Glu Glu Val Gly Arg Arg Met Gly Leu Glu Thr His Thr Leu
385                 390                 395                 400

Ala Ser Leu Trp Lys Asp Arg Ala Val Thr Glu Ile Asn Val Ala Val
                405                 410                 415

Leu His Ser Phe Gln Lys Gln Asn Val Thr Ile Met Asp His His Thr
            420                 425                 430

Ala Ser Glu Ser Phe Met Lys His Met Gln Asn Glu Tyr Arg Ala Arg
            435                 440                 445

Gly Gly Cys Pro Ala Asp Trp Ile Trp Leu Val Pro Pro Val Ser Gly
            450                 455                 460

Ser Ile Thr Pro Val Phe His Gln Glu Met Leu Asn Tyr Val Leu Ser
465                 470                 475                 480

Pro Phe Tyr Tyr Tyr Gln Ile Glu Pro Trp Lys Thr His Ile Trp Gln
                485                 490                 495
```

-continued

```
Asn Glu Lys Leu Arg Pro Arg Arg Glu Ile Arg Phe Arg Val Leu
            500                 505                 510
Val Lys Val Phe Phe Ala Ser Met Leu Met Arg Lys Val Met Ala
            515                 520                 525
Ser Arg Val Arg Ala Thr Val Leu Phe Ala Thr Glu Thr Gly Lys Ser
            530                 535                 540
Glu Ala Leu Ala Arg Asp Leu Ala Thr Leu Phe Ser Tyr Ala Phe Asn
545                 550                 555                 560
Thr Lys Val Val Cys Met Asp Gln Tyr Lys Ala Ser Thr Leu Glu Glu
                    565                 570                 575
Glu Gln Leu Leu Leu Val Val Thr Ser Thr Phe Gly Asn Gly Asp Cys
            580                 585                 590
Pro Ser Asn Gly Gln Thr Leu Lys Lys Ser Leu Phe Met Leu Arg Glu
            595                 600                 605
Leu Asn His Thr Phe Arg Tyr Ala Val Phe Gly Leu Gly Ser Ser Met
            610                 615                 620
Tyr Pro Gln Phe Cys Ala Phe Ala His Asp Ile Asp Gln Lys Leu Ser
625                 630                 635                 640
His Leu Gly Ala Ser Gln Leu Ala Pro Thr Gly Glu Gly Asp Glu Leu
                    645                 650                 655
Ser Gly Gln Glu Asp Ala Phe Arg Ser Trp Ala Val Gln Thr Phe Arg
                    660                 665                 670
Ala Ala Cys Glu Thr Phe Asp Val Arg Ser Lys His His Ile Gln Ile
                    675                 680                 685
Pro Lys Arg Phe Thr Ser Asn Ala Thr Trp Glu Pro Gln Gln Tyr Arg
            690                 695                 700
Leu Ile Gln Ser Pro Glu Pro Leu Asp Leu Asn Arg Ala Leu Ser Ser
705                 710                 715                 720
Ile His Ala Lys Asn Val Phe Thr Met Arg Leu Lys Ser Gln Gln Asn
                    725                 730                 735
Leu Gln Ser Glu Lys Ser Ser Arg Thr Thr Leu Leu Val Gln Leu Thr
            740                 745                 750
Phe Glu Gly Ser Arg Gly Pro Ser Tyr Leu Pro Gly Glu His Leu Gly
            755                 760                 765
Ile Phe Pro Gly Asn Gln Thr Ala Leu Val Gln Gly Ile Leu Glu Arg
            770                 775                 780
Val Val Asp Cys Pro Thr Pro His Gln Thr Val Cys Leu Glu Val Leu
785                 790                 795                 800
Asp Glu Ser Gly Ser Tyr Trp Val Lys Asp Lys Arg Leu Pro Pro Cys
                    805                 810                 815
Ser Leu Ser Gln Ala Leu Thr Tyr Phe Leu Asp Ile Thr Thr Pro Pro
                    820                 825                 830
Thr Gln Leu Gln Leu His Lys Leu Ala Arg Phe Ala Thr Asp Glu Thr
            835                 840                 845
Asp Arg Gln Arg Leu Glu Ala Leu Cys Gln Pro Ser Glu Tyr Asn Asp
            850                 855                 860
Trp Lys Phe Ser Asn Asn Pro Thr Phe Leu Glu Val Leu Glu Glu Phe
865                 870                 875                 880
Pro Ser Leu His Val Pro Ala Ala Phe Leu Leu Ser Gln Leu Pro Ile
                    885                 890                 895
Leu Lys Pro Arg Tyr Tyr Ser Ile Ser Ser Ser Gln Asp His Thr Pro
            900                 905                 910
```

-continued

```
Ser Glu Val His Leu Thr Val Ala Val Thr Tyr Arg Thr Arg Asp
            915                 920                 925

Gly Gln Gly Pro Leu His His Gly Val Cys Ser Thr Trp Ile Arg Asn
        930                 935                 940

Leu Lys Pro Gln Asp Pro Val Pro Cys Phe Arg Ser Val Ser Gly
945                 950                 955                 960

Phe Gln Leu Pro Glu Asp Pro Ser Gln Pro Cys Ile Leu Ile Gly Pro
                965                 970                 975

Gly Thr Gly Ile Ala Pro Phe Arg Ser Phe Trp Gln Gln Arg Leu His
            980                 985                 990

Asp Ser Gln His Lys Gly Leu Lys Gly Gly Arg Met Ser Leu Val Phe
        995                 1000                1005

Gly Cys Arg His Pro Glu Glu Asp His Leu Tyr Gln Glu Glu Met Gln
    1010                1015                1020

Glu Met Val Arg Lys Arg Val Leu Phe Gln Val His Thr Gly Tyr Ser
1025                1030                1035                1040

Arg Leu Pro Gly Lys Pro Lys Val Tyr Val Gln Asp Ile Leu Gln Lys
                1045                1050                1055

Gln Leu Ala Asn Glu Val Leu Ser Val Leu His Gly Glu Gln Gly His
            1060                1065                1070

Leu Tyr Ile Cys Gly Asp Val Arg Met Ala Arg Asp Val Ala Thr Thr
        1075                1080                1085

Leu Lys Lys Leu Val Ala Thr Lys Leu Asn Leu Ser Glu Glu Gln Val
    1090                1095                1100

Glu Asp Tyr Phe Phe Gln Leu Lys Ser Gln Arg Tyr His Glu Asp
1105                1110                1115                1120

Ile Phe Gly Ala Val Phe Ser Tyr Gly Ala Lys Lys Gly Ser Ala Leu
                1125                1130                1135

Glu Glu Pro Lys Ala Thr Arg Leu
            1140

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Gly Asp Pro Ala Asn Val Glu Phe Thr Glu Ile Cys Ile Gln Gln Gly
1               5                   10                  15

Trp Lys Pro Arg
            20

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Gly Asp Pro Met Asn Val Glu Phe Thr Glu Thr Val Ala Leu Lys Met
1               5                   10                  15
```

```
Gln Leu Asp Thr
            20

(2) INFORMATION FOR SEQ ID NO:15:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Cys Asp Asn Ser Arg Tyr Asn Ile Leu Glu Glu Val Ala Lys Lys Met
1               5                  10                  15

Asp Leu Asp Met
            20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Gly Asp Pro Ala Asn Val Glu Phe Thr Glu Glu Val Ala Lys Lys Met
1               5                  10                  15

Asp Leu Asp Met
            20

(2) INFORMATION FOR SEQ ID NO:17:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

CGTCTAGATC TATGACTGAA TATGACGTAA TATGACGTAA TGGTACCAGA TCTGGCC          57

(2) INFORMATION FOR SEQ ID NO:18:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

AAATGACGTA ACGGAAATGA CGTAACGGAA ATGACGTAAC G                           41

(2) INFORMATION FOR SEQ ID NO:19:

(i) SEQUENCE CHARACTERISTICS:
        (A) LENGTH: 42 base pairs
        (B) TYPE: nucleic acid
        (C) STRANDEDNESS: double
```

(D) TOPOLOGY: linear (ii) MOLECULE TYPE: DNA (genomic)

(xi) SEQUENCE DESCRIPTION: SEQ ID NO:19:

AAATGAATTA ACGGAAATGA ATTAACGGAA ATGAATTAAC GG                          42

(2) INFORMATION FOR SEQ ID NO:20:

(i) SEQUENCE CHARACTERISTICS:
            (A) LENGTH: 81 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:20:

TGCACGGGTT TTCGACGTTC ACTGGTAGTG TCTGATGAGG CCGAAAGGCC GAAACGCGAT        60

GCCCATAACC ACCACGCTCA G                                                 81

(2) INFORMATION FOR SEQ ID NO:21:

(i) SEQUENCE CHARACTERISTICS:
            (A) LENGTH: 100 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:21:

TCGACCCACA GTTTCGGGTT TTCGAGCAAG TCTGCTAGTG TCTGATGAGG CCGAAAGGCC        60

GAAACGCGAA GCCGTATTGC ACCACGCTCA TCGAGAAGGC                            100

(2) INFORMATION FOR SEQ ID NO:22:

(i) SEQUENCE CHARACTERISTICS:
            (A) LENGTH: 55 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:22:

CTAGAGCTTG CAAGCATGCT TGCAAGCAAG CATGCTTGCA AGCATGCTTG CAAGC            55

(2) INFORMATION FOR SEQ ID NO:23:

(i) SEQUENCE CHARACTERISTICS:
            (A) LENGTH: 34 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:23:

CTCTAGAGCG TACGCAAGCG TACGCAAGCG TACG                                   34

(2) INFORMATION FOR SEQ ID NO:24:

(i) SEQUENCE CHARACTERISTICS:
            (A) LENGTH: 17 amino acids
            (B) TYPE: amino acid
            (C) STRANDEDNESS:

-continued

```
        (D) TOPOLOGY: linear (ii) MOLECULE TYPE: peptide (xi) SEQUENCE DESCRIPTION: SEQ ID NO:24:

Arg Lys Arg Glu Ile Arg Leu Gln Lys Asn Arg Glu Ala Ala Arg Glu
1               5                   10                  15
Cys
```